(12) United States Patent
Brugiere

(10) Patent No.: US 7,893,236 B2
(45) Date of Patent: Feb. 22, 2011

(54) SOYBEAN ISOPENTENYL TRANSFERASE GENES AND METHODS OF USE

(75) Inventor: Norbert Brugiere, Johnston, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 78 days.

(21) Appl. No.: 12/469,732

(22) Filed: May 21, 2009

(65) Prior Publication Data

US 2009/0229018 A1 Sep. 10, 2009

Related U.S. Application Data

(62) Division of application No. 11/669,281, filed on Jan. 31, 2007, now Pat. No. 7,553,951.

(60) Provisional application No. 60/764,303, filed on Feb. 1, 2006.

(51) Int. Cl.
C07H 21/04 (2006.01)
C12N 15/82 (2006.01)
A01H 5/00 (2006.01)

(52) U.S. Cl. .............. 536/23.6; 800/298; 800/295; 435/419; 435/320.1

(58) Field of Classification Search ................ None
See application file for complete search history.

(56) References Cited

U.S. PATENT DOCUMENTS

2006/0010515 A1 1/2006 He

FOREIGN PATENT DOCUMENTS

EP 1 384 776 A1 1/2004
EP 1 522 586 A1 4/2005

OTHER PUBLICATIONS

Totoki et al. *Arabidopsis thaliana* mRNA for tRNA isopentenyl transferase, complete cds, clone: RAFL09-26-L15. (2005) GenBank Accession AK221649; pp. 1-2.*

Genbank Accession No. AY550884; Glycine max isopentenyl transferas (Ipt) mRNA; Feb. 2005.
Genbank Accession No. BM523542; Glycine max cDNA clone soybean clone ID: Gm-c1087-875 5' similar to TR: Q9ZUX7 Q9ZUX7 Putative TRNA Isopentenylpyrophosphate Transferase. mRNA sequence; Feb. 2002.
Genbank Accession No. BM091675; Glycine max cDNA clone Genome Systems Clone ID: Gm-c1086-66 5' similar to TR:Q9ZUX7 Q9ZUX7 Putative TRNA Isopentenylpyrophosphate Transferase. mRNA sequence; Nov. 2001.
Kakimoto, T.; "Identification of Play Cytokinin Biosynthetic Enzymes as Dimethylallyl Diphosphate: ATP/ADP Isopentenyltransferases"; Plant Cell Physiol (2001) 42(7):677-685; Oxford University Press; Oxford, UK.
Kakimoto, T.; "Biosynthesis of cytokinins"; J Plant Res (2003) 116:233-239; The Botanical Society of Japan and Springer-Verlag, Tokyo, JP.
Takei, K., et al.; "Identification of Genes Encoding Adenylate Isopentenyltranserase, a Cytokinin Biosynthesis Enzyme, in *Arabidopsis thaliana*"; The Journal of Biological Chemistry (Jul. 13, 2001) 276(28):26405-26410; The American Society for Biochemistry and Molecular Biology, Inc.; Bethesda, MD, US.
Genbank Accession No. CA784528; Glycine max cDNA clone Soybean Clone ID: Gm-c1062-5400 5' similar to TR:Q9ZUX7 Q9ZUX7 Putative TRNA Isopentenylpyrophosphate Transferase. mRNA sequence; Dec. 2002.
Ye, C., et al.; "Identification and characterization of an isopentenyltransferase (IPT) gene in soybean (*Glycine max* L.)"; Plant Science (2006) 170:542-550; Elsevier Ireland Ltd; IE.
Zubko, E., et al.; "Actvation tagging identifies a gene from *Petunia hybrida* responsible for the production of active cytokinins in plants" The Plant Journal (2002) 29(6):797-808; Blackwell Publishing Ltd; Oxford, UK.

* cited by examiner

*Primary Examiner*—Cathy Kingdon Worley

(57) ABSTRACT

Methods and compositions for modulating plant development are provided. Polynucleotide sequences encoding isopentenyl transferase (IPT) polypeptides are provided, as are the amino acid sequences of the encoded polypeptides. The sequences can be used in a variety of methods including modulating root development, modulating floral development, modulating leaf and/or shoot development, modulating senescence, modulating seed size and/or weight and modulating tolerance of plants to abiotic stress. Transformed plants, plant cells, tissues and seed are also provided.

7 Claims, 5 Drawing Sheets

Figure 1. Alignment of GmIPT protein sequences with ZmIPT2. Corresponding SEQ ID Numbers are shown at left.

```
ZmIPT2  8  ~~~~~~~~~~~~~~~~~~~~~~~~~~~~~~~~~~MEHGAVAGKPKVVFVLGATATGKSKLAIALAERFN.GEVINADK
GmIPT1  2  MNISTSACACACKQELPLVSFQKGSLMMESLFHHRNNSNKDKVVIMGATGAGKTKLAIDVAKHFQPAEIVNSDK
GmIPT2  4  MNMVSVSAAVCKPVVASFNPASLRNMDSLSLFRHHRN.NKEKVVVIMGATGTGKSKLAIDLATQFPPAEIVNSDK
GmIPT3  7  ~~~~~~~~~~~MAATESTVTSNPSNRERPKPKPKLLVITGPTASGKSKLAVDLASHFP.VELINADS
                                                *  * ***          *    ** *

ZmIPT2  8  IQVHDGVPIITNKVTEEEQGGVPHLLLSVRHPDADFTAEEFREAASAVARVLSAGRLPVVAGGSNTYIEALVEG.......
GmIPT1  2  MQVYKGLDITTNKVTEEECGGVPHLLLGTVDPYINFSANDFCRYATLAIDSIVEKNGLPIIAGGSNSYLDALVN.......
GmIPT2  4  MQVYEGLDITTNKVTEEERGRLHELLGTVNPTNFTAQDFCHATLAVGSILGRDGLPIIAGGSNSFLDALVN.......
GmIPT3  7  MQVYRGLDVLTNKLPLSHQNGVPHLLLGTVSPNVEFTAKAFRDSAIPIIDDILARNHLPVIVGGTNYYIQALVSPFLLDD
           *                                                              *

ZmIPT2  8  ................
GmIPT1  2  ................
GmIPT2  4  ................
GmIPT3  7  SAEDMDESCLGDPTGSGNNFTGENDCSNNSYDLLKDIDPVAANRIHPNNHRKINQYINLYNRTGVLPSNIFQGKAAEGQK

ZmIPT2  8  DGAAFRAAHDLLFVWVDAEQELLEWYAALRVDEMVARGLIVSEARAAFGGAGVDYNHGVRRAIGLPEMHAYLVAERRGVAG
GmIPT1  2  HYPEFRLRYQCCFLWVDVALPVLHSSLQARVDRMIEAGQVNEVRDFFDPSVTDYTKGIRRAIGVPEFDDFLRAEANGRLD
GmIPT2  4  HHTEFRLRYECCFLWVDVSLPVLHSSLSARVDRMIHAGQVHEVRKSFQYHNDDYTVGLRKAIGVPEFHDFFRAEADG.AD
GmIPT3  7  WGQVDNLRYDCCFICVDASLPVLDRYVEQRVDCMMHEGLLNEVYDIYN.LNAVYTRGLRQAIGVREFEPLLRTCVVKDMH

ZmIPT2  8  EAELAAM...................LERAVREIKDNTFRLARTQAEKIRRLSTLDGWDVRRIDVTPV
GmIPT1  2  ERTKQRL....................LQAAIARLKINNCTLANRQIQKIHRLHAFWKRNMHRLDATEV
GmIPT2  4  ERTKQRL....................LEAAIASLKTNNCSLANRQVQKIHRLYGMWKRNMHRLDATEV
GmIPT3  7  ERERELTEGSSIEKGETLFNHNLMELVRSSNTESTILLEEAIEKVKLNTRRLIRRQKRMLSRLQTLFGWNIHYDSTES

ZmIPT2  8  FARKADGTECHELITWKKQVWEPCEEMVRAFLEPSLTAVPGVAVTEEGNAGVVATAAPAGDVVVPTGDVVTAVADA~~~~
GmIPT1  2  FRG.......SHDAWRDHVLAKTLIILHKFLYGEKKTP......HVVPAGIVSAKDVIAAAAVLSSPPVAMAATR~~~~~
GmIPT2  4  FLKNATRQEEAEEAWEDHVLSKSRRILNKFLY.EDT.......HVAPAGIAASVVIASSPPAMAAAAAATH~~~~~~~~
GmIPT3  7  ISSK......SEDVWTRQVVESAVKIVKSFLSENGTIFG...TSNDTGMKIIQRDLWTQYICKACGDRVLRGFHEWEQHR
                                                                                        ◆

ZmIPT2  8  ~~~~~~~~~~~~~~~~~~~~~~~~~~~~~~~~~~~~
GmIPT1  2  ~~~~~~~~~~~~~~~~~~~~~~~~~~~~~~~~~~~~
GmIPT2  4  ~~~~~~~~~~~~~~~~~~~~~~~~~~~~~~~~~~~~
GmIPT3  7  QGRGHRKRISRLKRKAQVPGFVEEVKYSASEQLDI
           ◆
```

\* Consensus sequence IPT: GxTxxGK[ST]xxxxx[VLI]xxxxxxx[VLI][VLI]xxDxxQx{57,60}[VLI][VLI]xGG[ST]
◆ tRNA binding site found in tRNA IPT proteins: CxxCx{12,18}HxxxxxH

|  | GmIPT1 | GmIPT2 | GmIPT3 |
|---|---|---|---|
| GmIPT1 (I) | 100 | | |
| GmIPT1 (S) | 100 | | |
| GmIPT2 (I) | 61.8 | 100 | |
| GmIPT2 (S) | 71.6 | 100 | |
| GmIPT3 (I) | 24.2 | 24.1 | 100 |
| GmIPT3 (S) | 33.3 | 32.6 | 100 |
| ZmIPT2 (I) | 32.8 | 30.4 | 22.2 |
| ZmIPT2 (S) | 44.6 | 46.7 | 32.7 |
| AtIPT1 (I) | 30.9 | 33.7 | 30.9 |
| AtIPT1 (S) | 46.5 | 45.8 | 46.5 |
| AtIPT2 (I) | 23.5 | 22.8 | 50.9 |
| AtIPT2 (S) | 35.1 | 32.9 | 63.3 |
| AtIPT3 (I) | 42.4 | 43.1 | 22.1 |
| AtIPT3 (S) | 54.6 | 57.4 | 33.5 |
| AtIPT4 (I) | 29.7 | 30.7 | 21.0 |
| AtIPT4 (S) | 42.2 | 42.7 | 30.3 |
| AtIPT5 (I) | 49.6 | 51.8 | 25.6 |
| AtIPT5 (S) | 62.8 | 61.7 | 35.4 |
| AtIPT6 (I) | 30.9 | 31.6 | 21.5 |
| AtIPT6 (S) | 43.2 | 43.2 | 32.1 |
| AtIPT7 (I) | 43.0 | 45.0 | 24.1 |
| AtIPT7 (S) | 57.0 | 59.6 | 33.4 |
| AtIPT8 (I) | 32.2 | 32.5 | 22.1 |
| AtIPT8 (S) | 45.9 | 46.4 | 32.1 |
| AtIPT9 (I) | 15.0 | 16.5 | 18.1 |
| AtIPT9 (S) | 29.1 | 28.6 | 31.5 |

Figure 2. Percent identity (I) and similarity (S) of IPT polypeptide sequences determined by GAP analysis as described in specification.

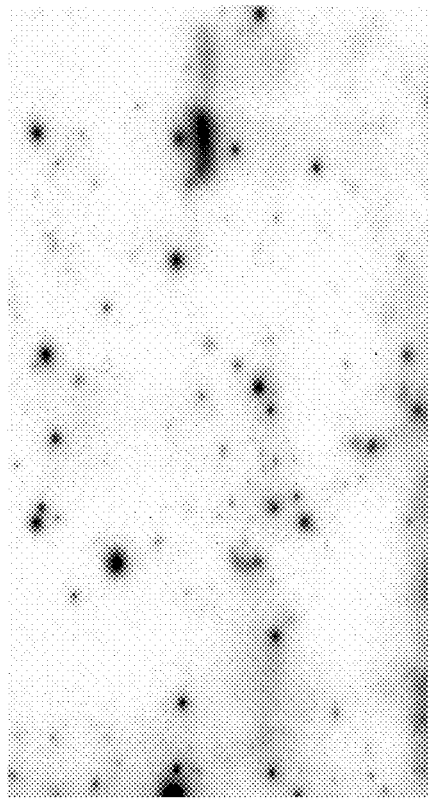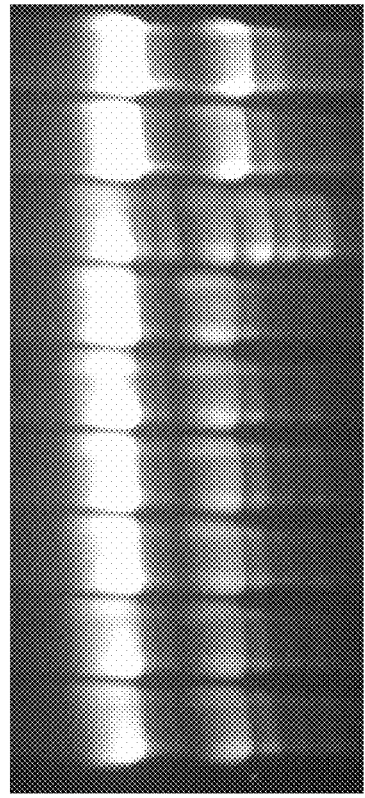
Figure 3A. Northern blot using GmIPT1 (AY550884) as a probe with 30µg total RNA extracted from soybean cultivar Jack at R4 and R5 ▲
Ethidium bromide stained gel ▲

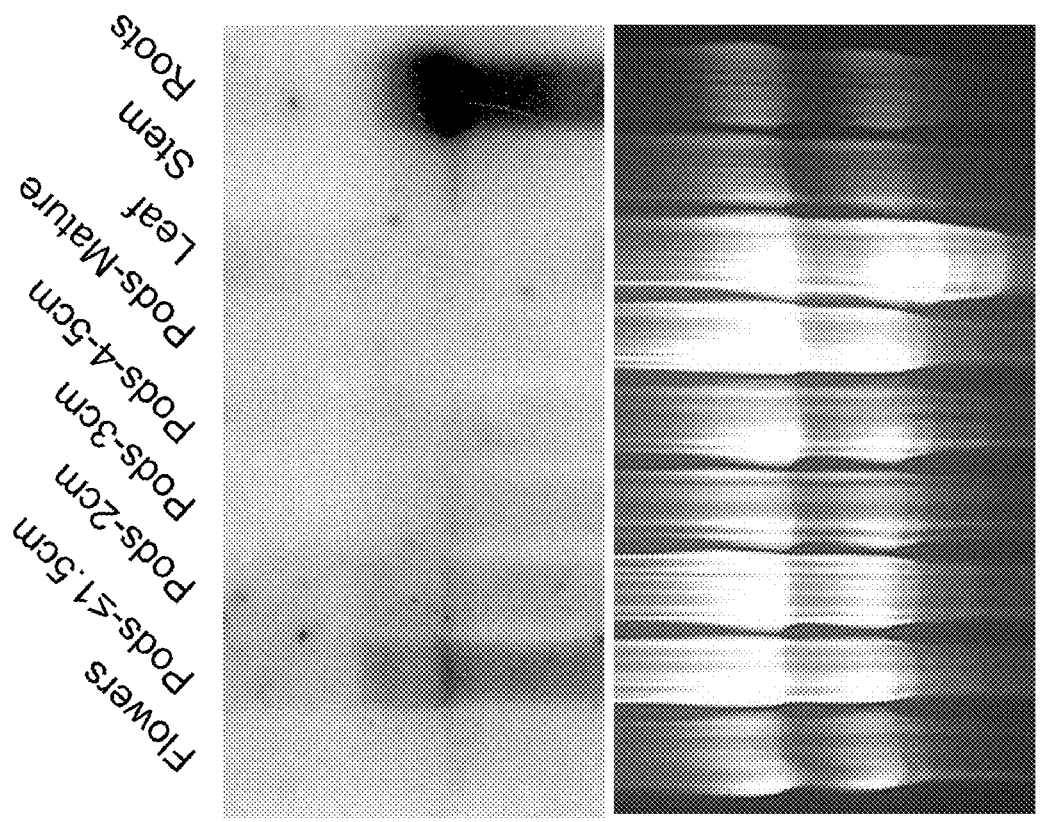
Figure 3B. Northern blot using GmIPT2 as a probe with 30μg total RNA extracted from soybean cultivar Jack at R4 and R5 ▲
Ethidium bromide stained gel ▲

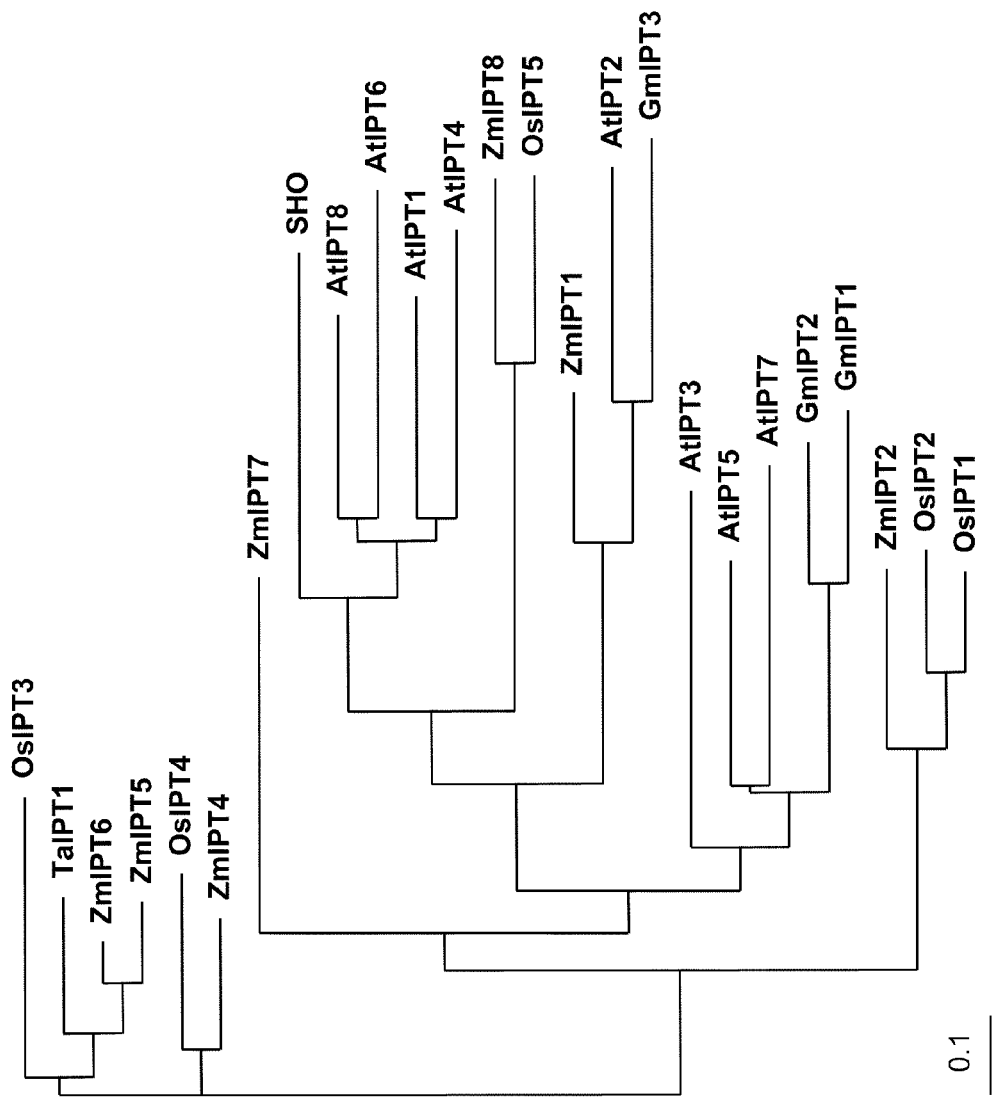
Figure 4. Un-rooted phylogenetic tree using the neighbor-joining method. Os, *Oryza sativa*; Ta, *Triticum aestivum*; Zm, *Zea mays*; SHO, petunia; At, *Arabidopsis thaliana*; Gm, *Glycine max.*

SEQUENCE LISTING

<160> NUMBER OF SEQ ID NOS: 34

<210> SEQ ID NO 1
<211> LENGTH: 1023
<212> TYPE: DNA
<213> ORGANISM: Glycine max
<220> FEATURE:
<221> NAME/KEY: CDS
<222> LOCATION: (1)...(1023)
<223> OTHER INFORMATION: GmIPT1

<400> SEQUENCE: 1

```
atg aac atc tca aca tca gcc tgc gcc tgc gcc tgc aaa cag gag ctg     48
Met Asn Ile Ser Thr Ser Ala Cys Ala Cys Ala Cys Lys Gln Glu Leu
 1               5                  10                  15
```

```
ccc cta gta agc ttc caa aag gga tca ctt atg atg gag tcg ttg ttt      96
Pro Leu Val Ser Phe Gln Lys Gly Ser Leu Met Met Glu Ser Leu Phe
         20                  25                  30 cat cat cgg aat aac agc aac aag gat aag gta gtg gtg ata atg ggg     144
His His Arg Asn Asn Ser Asn Lys Asp Lys Val Val Val Ile Met Gly
         35                  40                  45 gcc act ggt gcc ggc aag acg aag ttg gct ata gac gtg gcc aaa cac     192
Ala Thr Gly Ala Gly Lys Thr Lys Leu Ala Ile Asp Val Ala Lys His
 50                  55                  60 ttc caa cca gcg gag ata gtg aac tca gac aaa atg caa gtg tac aag     240
Phe Gln Pro Ala Glu Ile Val Asn Ser Asp Lys Met Gln Val Tyr Lys
 65                  70                  75                  80 ggc cta gac atc acc acc aat aag gtc act gaa gaa gag tgt ggc ggg     288
Gly Leu Asp Ile Thr Thr Asn Lys Val Thr Glu Glu Glu Cys Gly Gly
                 85                  90                  95 gtc cca cat cat ctg ctt ggc act gtt gac cca tat ata aat ttc agc     336
Val Pro His His Leu Leu Gly Thr Val Asp Pro Tyr Ile Asn Phe Ser
             100                 105                 110 gcc aac gac ttc tgt cgc tac gcc act ttg gcc atc gac tcc att gta     384
Ala Asn Asp Phe Cys Arg Tyr Ala Thr Leu Ala Ile Asp Ser Ile Val
         115                 120                 125 gaa aaa aat ggc tta ccc atc atc gct gga ggc tct aat tct tat tta     432
Glu Lys Asn Gly Leu Pro Ile Ile Ala Gly Gly Ser Asn Ser Tyr Leu
 130                 135                 140 gac gcg ttg gtc aat cat tat cct gag ttt agg tta agg tac cag tgc     480
Asp Ala Leu Val Asn His Tyr Pro Glu Phe Arg Leu Arg Tyr Gln Cys
145                 150                 155                 160 tgt ttc ctc tgg gtc gac gtg gca ctc ccc gtt ctc cat tcc tcc ctc     528
Cys Phe Leu Trp Val Asp Val Ala Leu Pro Val Leu His Ser Ser Leu
                 165                 170                 175 cag gca cgt gtg gac cgc atg atc gaa gcc ggt caa gtc aac gag gtt     576
Gln Ala Arg Val Asp Arg Met Ile Glu Ala Gly Gln Val Asn Glu Val
             180                 185                 190 cgt gac ttc ttc gac ccg agc gta acc gat tac acc aaa ggg ata cga     624
Arg Asp Phe Phe Asp Pro Ser Val Thr Asp Tyr Thr Lys Gly Ile Arg
         195                 200                 205 agg gct att ggg gtg ccc gaa ttc gac gat ttt ctt cgc gca gag gcg     672
Arg Ala Ile Gly Val Pro Glu Phe Asp Asp Phe Leu Arg Ala Glu Ala
 210                 215                 220 aat ggg cgg cta gat gag aga aca aaa cag agg ctt ctt cag gct gcc     720
Asn Gly Arg Leu Asp Glu Arg Thr Lys Gln Arg Leu Leu Gln Ala Ala
225                 230                 235                 240 att gca agg ttg aag atc aac aac tgc acg ctc gcc aac cgc cag att     768
Ile Ala Arg Leu Lys Ile Asn Asn Cys Thr Leu Ala Asn Arg Gln Ile
                 245                 250                 255 cag aag atc cac cgc ctg cac gcc ttc tgg aaa cgg aac atg cac cgc     816
Gln Lys Ile His Arg Leu His Ala Phe Trp Lys Arg Asn Met His Arg
             260                 265                 270 ctc gac gcc acc gag gtt ttc cgc ggc tca cat gac gcc tgg cgc gat     864
Leu Asp Ala Thr Glu Val Phe Arg Gly Ser His Asp Ala Trp Arg Asp
         275                 280                 285 cac gtg ctc gcc aag acc ttg atc atc ctc cac aag ttt ctc tac gga     912
His Val Leu Ala Lys Thr Leu Ile Ile Leu His Lys Phe Leu Tyr Gly
 290                 295                 300 gag aag aaa acg ccg cac gtt gtc ccc gcc gga atc gtc tcc gcc aaa     960
Glu Lys Lys Thr Pro His Val Val Pro Ala Gly Ile Val Ser Ala Lys
305                 310                 315                 320 gac gta att gcg gcg gcg gcg gtg ctt tct tcg ccg ccg gta gca atg    1008
Asp Val Ile Ala Ala Ala Ala Val Leu Ser Ser Pro Pro Val Ala Met
```

```
                    325              330              335
gca gca acg cgg tag                                                    1023
Ala Ala Thr Arg  *
        340
```

<210> SEQ ID NO 2
<211> LENGTH: 340
<212> TYPE: PRT
<213> ORGANISM: Glycine max

<400> SEQUENCE: 2

```
Met Asn Ile Ser Thr Ser Ala Cys Ala Cys Ala Lys Gln Glu Leu
 1               5                  10                  15

Pro Leu Val Ser Phe Gln Lys Gly Ser Leu Met Met Glu Ser Leu Phe
                20                  25                  30

His His Arg Asn Asn Ser Asn Lys Asp Lys Val Val Val Ile Met Gly
             35                  40                  45

Ala Thr Gly Ala Gly Lys Thr Lys Leu Ala Ile Asp Val Ala Lys His
         50                  55                  60

Phe Gln Pro Ala Glu Ile Val Asn Ser Asp Lys Met Gln Val Tyr Lys
 65                  70                  75                  80

Gly Leu Asp Ile Thr Thr Asn Lys Val Thr Glu Glu Cys Gly Gly
                 85                  90                  95

Val Pro His His Leu Leu Gly Thr Val Asp Pro Tyr Ile Asn Phe Ser
                100                 105                 110

Ala Asn Asp Phe Cys Arg Tyr Ala Thr Leu Ala Ile Asp Ser Ile Val
            115                 120                 125

Glu Lys Asn Gly Leu Pro Ile Ile Ala Gly Gly Ser Asn Ser Tyr Leu
        130                 135                 140

Asp Ala Leu Val Asn His Tyr Pro Glu Phe Arg Leu Arg Tyr Gln Cys
145                 150                 155                 160

Cys Phe Leu Trp Val Asp Val Ala Leu Pro Val Leu His Ser Ser Leu
                165                 170                 175

Gln Ala Arg Val Asp Arg Met Ile Glu Ala Gly Gln Val Asn Glu Val
            180                 185                 190

Arg Asp Phe Phe Asp Pro Ser Val Thr Asp Tyr Thr Lys Gly Ile Arg
        195                 200                 205

Arg Ala Ile Gly Val Pro Glu Phe Asp Asp Phe Leu Arg Ala Glu Ala
    210                 215                 220

Asn Gly Arg Leu Asp Glu Arg Thr Lys Gln Arg Leu Leu Gln Ala Ala
225                 230                 235                 240

Ile Ala Arg Leu Lys Ile Asn Asn Cys Thr Leu Ala Asn Arg Gln Ile
                245                 250                 255

Gln Lys Ile His Arg Leu His Ala Phe Trp Lys Arg Asn Met His Arg
            260                 265                 270

Leu Asp Ala Thr Glu Val Phe Arg Gly Ser His Asp Ala Trp Arg Asp
        275                 280                 285

His Val Leu Ala Lys Thr Leu Ile Ile Leu His Lys Phe Leu Tyr Gly
    290                 295                 300

Glu Lys Lys Thr Pro His Val Val Pro Ala Gly Ile Val Ser Ala Lys
305                 310                 315                 320

Asp Val Ile Ala Ala Ala Val Leu Ser Ser Pro Val Ala Met
                325                 330                 335

Ala Ala Thr Arg
        340
```

<210> SEQ ID NO 3
<211> LENGTH: 1409
<212> TYPE: DNA
<213> ORGANISM: Glycine max
<220> FEATURE:
<221> NAME/KEY: CDS
<222> LOCATION: (60)...(1079)
<223> OTHER INFORMATION: GmIPT2

<400> SEQUENCE: 3

| | |
|---|---|
| aggaattcgg cacgagaact tgcaggttt gagagaagag agaaaaaaca aaaagagac | 59 |
| atg aac atg gtt tcg gtg tca gca gcg gtg tgc aag ccc gta gta gcg<br>Met Asn Met Val Ser Val Ser Ala Ala Val Cys Lys Pro Val Val Ala<br>1                    5                    10                 15 | 107 |
| agt ttc aac ccg gca tca ctg agg aat atg gac tcg ctg tcc ctt ttt<br>Ser Phe Asn Pro Ala Ser Leu Arg Asn Met Asp Ser Leu Ser Leu Phe<br>                    20                    25                    30 | 155 |
| cgt cac cac cgc aac aac aag gag aaa gta gtg gta atc atg ggc gca<br>Arg His His Arg Asn Asn Lys Glu Lys Val Val Val Ile Met Gly Ala<br>         35                    40                    45 | 203 |
| acg ggg aca gga aag tca aaa ctg gca ata gac ctc gcc acg caa ttc<br>Thr Gly Thr Gly Lys Ser Lys Leu Ala Ile Asp Leu Ala Thr Gln Phe<br>50                    55                    60 | 251 |
| cca cca gcg gag ata gtc aac tcc gac aaa atg caa gtg tac gaa ggc<br>Pro Pro Ala Glu Ile Val Asn Ser Asp Lys Met Gln Val Tyr Glu Gly<br>65                    70                    75                    80 | 299 |
| cta gac atc acc acg aac aaa gtc acc gag gaa gag cgt cgc ggg gtc<br>Leu Asp Ile Thr Thr Asn Lys Val Thr Glu Glu Glu Arg Arg Gly Val<br>                    85                    90                    95 | 347 |
| cta cac cat ctc cta ggc acg gtc aac ccc aac acc aac ttc acc gcc<br>Leu His His Leu Leu Gly Thr Val Asn Pro Asn Thr Asn Phe Thr Ala<br>                100                 105               110 | 395 |
| caa gac ttt tgc gac cac gcc aca ctc gcc gtt ggc tcc att ttg ggc<br>Gln Asp Phe Cys Asp His Ala Thr Leu Ala Val Gly Ser Ile Leu Gly<br>115                  120                 125 | 443 |
| cgt gac ggt tta ccc atc att gcg ggt ggg tcc aat tcc ttc ctc gac<br>Arg Asp Gly Leu Pro Ile Ile Ala Gly Gly Ser Asn Ser Phe Leu Asp<br>130                  135                 140 | 491 |
| gcg ttg gtc aac cat cac acc gag ttt cgg tta cgc tac gag tgc tgc<br>Ala Leu Val Asn His His Thr Glu Phe Arg Leu Arg Tyr Glu Cys Cys<br>145                  150                 155               160 | 539 |
| ttc ctc tgg gtc gat gtt tca ctc ccc gtc ctt cat tcc tct ctc tcc<br>Phe Leu Trp Val Asp Val Ser Leu Pro Val Leu His Ser Ser Leu Ser<br>                    165                 170               175 | 587 |
| gca cgt gtg gat cgc atg atc cac gct ggc cag gtc cac gag gtt cga<br>Ala Arg Val Asp Arg Met Ile His Ala Gly Gln Val His Glu Val Arg<br>                180                 185               190 | 635 |
| aaa agc ttt cag tac cat aac gac gat tat acc gta ggt tta cga aag<br>Lys Ser Phe Gln Tyr His Asn Asp Asp Tyr Thr Val Gly Leu Arg Lys<br>195                200                 205 | 683 |
| gcc ata ggc gtc cct gag ttt cat gat ttt ttc aga gcc gaa gcc gac<br>Ala Ile Gly Val Pro Glu Phe His Asp Phe Phe Arg Ala Glu Ala Asp<br>210                  215                 220 | 731 |
| gga gcc gat gag agg acc aaa cag cgg ctc ctc gag gct gcc att gct<br>Gly Ala Asp Glu Arg Thr Lys Gln Arg Leu Leu Glu Ala Ala Ile Ala<br>225                  230                 235               240 | 779 |
| tcc ctc aaa acc aac aac tgc agc ctc gcc aac cga cag gtc cag aag<br>Ser Leu Lys Thr Asn Asn Cys Ser Leu Ala Asn Arg Gln Val Gln Lys<br>                    245                 250               255 | 827 |

```
att cat cgt ctt tac ggc atg tgg aaa agg aac atg cac cgc ctc gac      875
Ile His Arg Leu Tyr Gly Met Trp Lys Arg Asn Met His Arg Leu Asp
        260                 265                 270 gcc acc gag gtt ttt ctc aag aac gct act cgc cag gag gag gca gag      923
Ala Thr Glu Val Phe Leu Lys Asn Ala Thr Arg Gln Glu Glu Ala Glu
    275                 280                 285 gag gcg tgg gag gat cac gtg ttg tcc aag agc aga agg att ctc aat      971
Glu Ala Trp Glu Asp His Val Leu Ser Lys Ser Arg Arg Ile Leu Asn
290                 295                 300 aag ttt ctg tat gag gat acg cat gtc gct ccc gca ggt att gct gcg     1019
Lys Phe Leu Tyr Glu Asp Thr His Val Ala Pro Ala Gly Ile Ala Ala
305                 310                 315                 320 tca gtt gtt att gct tct tcg ccg cca gcc atg gct gcc gcc gcc gcc     1067
Ser Val Val Ile Ala Ser Ser Pro Pro Ala Met Ala Ala Ala Ala Ala
            325                 330                 335 gcc gca act cac tagagatata tactatatag ggccagagaa tctaatatag          1119
Ala Ala Thr His
        340 agaaaagttc cccactgaca tgcctccgat gacactacta catgccattt cacatacttt    1179 atttttact tttggtatcg taaaaaaaaa ggtttactag ctatatgtat aatcttttgt     1239 tacttactag tactatatat gtaatgtgtt acaatcatat caccgaaata cttaacagta    1299 atccatgagt taattatagt attaatcaag cttccttcag cttatgccta gctagctaca    1359 ttattgttcg ctaatattat tatggccggg gtaactgttg caacttgaac               1409

<210> SEQ ID NO 4
<211> LENGTH: 340
<212> TYPE: PRT
<213> ORGANISM: Glycine max

<400> SEQUENCE: 4

Met Asn Met Val Ser Val Ser Ala Ala Val Cys Lys Pro Val Val Ala
1               5                   10                  15

Ser Phe Asn Pro Ala Ser Leu Arg Asn Met Asp Ser Leu Ser Leu Phe
            20                  25                  30

Arg His His Arg Asn Asn Lys Glu Lys Val Val Val Ile Met Gly Ala
        35                  40                  45

Thr Gly Thr Gly Lys Ser Lys Leu Ala Ile Asp Leu Ala Thr Gln Phe
    50                  55                  60

Pro Pro Ala Glu Ile Val Asn Ser Asp Lys Met Gln Val Tyr Glu Gly
65                  70                  75                  80

Leu Asp Ile Thr Thr Asn Lys Val Thr Glu Glu Arg Arg Gly Val
            85                  90                  95

Leu His His Leu Leu Gly Thr Val Asn Pro Asn Thr Asn Phe Thr Ala
        100                 105                 110

Gln Asp Phe Cys Asp His Ala Thr Leu Ala Val Gly Ser Ile Leu Gly
    115                 120                 125

Arg Asp Gly Leu Pro Ile Ile Ala Gly Gly Ser Asn Ser Phe Leu Asp
130                 135                 140

Ala Leu Val Asn His His Thr Glu Phe Arg Leu Arg Tyr Glu Cys Cys
145                 150                 155                 160

Phe Leu Trp Val Asp Val Ser Leu Pro Val Leu His Ser Ser Leu Ser
            165                 170                 175

Ala Arg Val Asp Arg Met Ile His Ala Gly Gln Val His Glu Val Arg
        180                 185                 190

Lys Ser Phe Gln Tyr His Asn Asp Asp Tyr Thr Val Gly Leu Arg Lys
```

```
                195                 200                 205
Ala Ile Gly Val Pro Glu Phe His Asp Phe Phe Arg Ala Glu Ala Asp
            210                 215                 220

Gly Ala Asp Glu Arg Thr Lys Gln Arg Leu Leu Glu Ala Ala Ile Ala
225                 230                 235                 240

Ser Leu Lys Thr Asn Asn Cys Ser Leu Ala Asn Arg Gln Val Gln Lys
                245                 250                 255

Ile His Arg Leu Tyr Gly Met Trp Lys Arg Asn Met His Arg Leu Asp
            260                 265                 270

Ala Thr Glu Val Phe Leu Lys Asn Ala Thr Arg Gln Glu Glu Ala Glu
        275                 280                 285

Glu Ala Trp Glu Asp His Val Leu Ser Lys Ser Arg Arg Ile Leu Asn
    290                 295                 300

Lys Phe Leu Tyr Glu Asp Thr His Val Ala Pro Ala Gly Ile Ala Ala
305                 310                 315                 320

Ser Val Val Ile Ala Ser Ser Pro Ala Met Ala Ala Ala Ala Ala
                325                 330                 335

Ala Ala Thr His
            340

<210> SEQ ID NO 5
<211> LENGTH: 768
<212> TYPE: DNA
<213> ORGANISM: Glycine max

<400> SEQUENCE: 5
aggaattcgg cacgagaact tggcaggttt gagagaagag agaaaaaaca aaaagagaca      60
tgaacatggt ttcggtgtca gcagcggtgt gcaagcccgt agtagcgagt ttcaacccgg     120
catcactgag gaatatggac tcgctgtccc ttttcgtca ccaccgcaac aacaaggaga      180
aagtagtggt aatcatgggc gcaacgggga caggaaagtc aaaactggca atagacctcg     240
ccacgcaatt cccaccagcg gagatagtca actccgacaa aatgcaagtg tacgaaggcc     300
tagacatcac cacgaacaaa gtcaccgagg aagagcgtcg cggggtccta ccatctcc       360
taggcacggt caaccccaac accaacttca ccgcccaaga cttttgcgac cacgccacac     420
tcgccgttgg ctccattttg ggccgtgacg gtttacccat cattgcgggt gggtccaatt     480
ccttcctcga cgcgttggtc aaccatcaca ccgagtttcg gttacgctac gagtgctgct     540
tcctctgggt cgatgtttca ctccccgtcc ttcattcctc tctctccgca cgtgtggatc     600
gcatgatcca cgctggccag gtccacgagg ttcgaaaaag ctttcagtac ataacgacg      660
attataccgt aggtttacga aaggccatag gcgtccctga gtttcatgat tttttcagag     720
ccgaagccga cggagccgat gagaggacca aacagcggct cctcgagg                 768

<210> SEQ ID NO 6
<211> LENGTH: 1592
<212> TYPE: DNA
<213> ORGANISM: Glycine max
<220> FEATURE:
<221> NAME/KEY: CDS
<222> LOCATION: (37)...(1476)
<223> OTHER INFORMATION: GmIPT3
<220> FEATURE:
<221> NAME/KEY: misc_feature
<222> LOCATION: 675
<223> OTHER INFORMATION: n = A,T,C or G

<400> SEQUENCE: 6
```

-continued

| | |
|---|---|
| ggagaacgta gagtgaaaga gaggttaaca ataaca atg gcg gcg aca gag agc<br>Met Ala Ala Thr Glu Ser<br>1                 5 | 54 |
| aca gta act tca aac cct agc aac aga gaa cga cca aag cca aag cca<br>Thr Val Thr Ser Asn Pro Ser Asn Arg Glu Arg Pro Lys Pro Lys Pro<br>      10                15               20 | 102 |
| aag cta cta gtc ata acg ggc ccc acc gct tcc ggg aag tcg aag cta<br>Lys Leu Leu Val Ile Thr Gly Pro Thr Ala Ser Gly Lys Ser Lys Leu<br>         25                30               35 | 150 |
| gcc gtt gat ttg gcc tcc cac ttc ccc gtc gaa ctc atc aac gcc gat<br>Ala Val Asp Leu Ala Ser His Phe Pro Val Glu Leu Ile Asn Ala Asp<br>40               45               50 | 198 |
| tcc atg cag gtc tac cgc ggc ctc gat gtt ctc acc aac aaa ctc cct<br>Ser Met Gln Val Tyr Arg Gly Leu Asp Val Leu Thr Asn Lys Leu Pro<br>55               60               65               70 | 246 |
| ctc tct cac cag aac gga gtt ccg cat cat ctc ttg ggt acc gta agc<br>Leu Ser His Gln Asn Gly Val Pro His His Leu Leu Gly Thr Val Ser<br>            75                80              85 | 294 |
| ccc aac gtg gaa ttc act gcc aaa gcg ttt cgg gat tcc gct att ccc<br>Pro Asn Val Glu Phe Thr Ala Lys Ala Phe Arg Asp Ser Ala Ile Pro<br>            90                95              100 | 342 |
| att att gat gat ata ttg gct cgt aat cac ttg cct gtt ata gtt ggg<br>Ile Ile Asp Asp Ile Leu Ala Arg Asn His Leu Pro Val Ile Val Gly<br>         105              110             115 | 390 |
| ggc act aat tac tat atc cag gct ctt gtg agt ccg ttt ctt tta gat<br>Gly Thr Asn Tyr Tyr Ile Gln Ala Leu Val Ser Pro Phe Leu Leu Asp<br>120             125              130 | 438 |
| gat tct gca gaa gat atg gat gaa agc tgt ttg ggt gat cca act ggg<br>Asp Ser Ala Glu Asp Met Asp Glu Ser Cys Leu Gly Asp Pro Thr Gly<br>135             140              145             150 | 486 |
| tct ggt aac aat ttc att ggt gaa aat gac tgt tca aac aat agt tat<br>Ser Gly Asn Asn Phe Ile Gly Glu Asn Asp Cys Ser Asn Asn Ser Tyr<br>            155              160             165 | 534 |
| gac ctg ctt aaa gat att gat cca gtt gca gca aat aga atc cat cca<br>Asp Leu Leu Lys Asp Ile Asp Pro Val Ala Ala Asn Arg Ile His Pro<br>            170              175             180 | 582 |
| aat aac cat aga aag ata aat caa tat att aat ttg tac aat cgc act<br>Asn Asn His Arg Lys Ile Asn Gln Tyr Ile Asn Leu Tyr Asn Arg Thr<br>         185              190              195 | 630 |
| ggt gtt ctt cct agc aat att ttt caa gga aag gca gca gag ggn cag<br>Gly Val Leu Pro Ser Asn Ile Phe Gln Gly Lys Ala Ala Glu Gly Gln<br>200             205              210 | 678 |
| aag tgg ggt caa gtt gat aac tta aga tat gat tgt tgt ttt ata tgt<br>Lys Trp Gly Gln Val Asp Asn Leu Arg Tyr Asp Cys Cys Phe Ile Cys<br>215             220              225             230 | 726 |
| gtg gat gca tct ctc cct gta ctg gac aga tat gta gag cag agg gta<br>Val Asp Ala Ser Leu Pro Val Leu Asp Arg Tyr Val Glu Gln Arg Val<br>            235              240             245 | 774 |
| gat tgc atg atg cat gag gga tta ctc aat gaa gtc tat gac att tat<br>Asp Cys Met Met His Glu Gly Leu Leu Asn Glu Val Tyr Asp Ile Tyr<br>            250              255             260 | 822 |
| aac ttg aat gca gtt tat act aga ggt ttg cgg caa gcc att ggt gtc<br>Asn Leu Asn Ala Val Tyr Thr Arg Gly Leu Arg Gln Ala Ile Gly Val<br>         265              270              275 | 870 |
| cgt gaa ttt gag cct ctt ctt aga act tgt gtt gtc aaa gac atg cat<br>Arg Glu Phe Glu Pro Leu Leu Arg Thr Cys Val Val Lys Asp Met His<br>280             285              290 | 918 |
| gaa aga gag agg gaa ttg act gaa gga tcc agc ata gaa aag gga gag<br>Glu Arg Glu Arg Glu Leu Thr Glu Gly Ser Ser Ile Glu Lys Gly Glu<br>295             300              305             310 | 966 |

```
aca tta ttt aat cat aat ttg atg gag ttg gtg aga tct tcc tct aat    1014
Thr Leu Phe Asn His Asn Leu Met Glu Leu Val Arg Ser Ser Ser Asn
                315                 320                 325 act gaa tcc aca att ctt ttg gaa gaa gca att gaa aaa gta aag ctt    1062
Thr Glu Ser Thr Ile Leu Leu Glu Glu Ala Ile Glu Lys Val Lys Leu
            330                 335                 340 aat acc cga aga ctt att cgc cgt cag aag agg atg ctc agt cga ctg    1110
Asn Thr Arg Arg Leu Ile Arg Arg Gln Lys Arg Met Leu Ser Arg Leu
        345                 350                 355 caa act ctg ttt ggt tgg aac ata cac tat gtt gat tcc aca gaa tca    1158
Gln Thr Leu Phe Gly Trp Asn Ile His Tyr Val Asp Ser Thr Glu Ser
    360                 365                 370 ata tca agc aaa tca gaa gat gta tgg acc cgg caa gtg gtt gaa tct    1206
Ile Ser Ser Lys Ser Glu Asp Val Trp Thr Arg Gln Val Val Glu Ser
375                 380                 385                 390 gct gtg aag ata gtc aaa tct ttc ctg agt gag aat gga acc atc ttt    1254
Ala Val Lys Ile Val Lys Ser Phe Leu Ser Glu Asn Gly Thr Ile Phe
                395                 400                 405 ggg acg tca aat gac acg ggg atg aaa ata atc caa agg gac ctc tgg    1302
Gly Thr Ser Asn Asp Thr Gly Met Lys Ile Ile Gln Arg Asp Leu Trp
            410                 415                 420 act caa tac ata tgc aag gcc tgc gga gat cgt gtg ctt aga gga ttt    1350
Thr Gln Tyr Ile Cys Lys Ala Cys Gly Asp Arg Val Leu Arg Gly Phe
        425                 430                 435 cat gaa tgg gag caa cac aga caa ggt cga ggg cac cga aaa cgt ata    1398
His Glu Trp Glu Gln His Arg Gln Gly Arg Gly His Arg Lys Arg Ile
    440                 445                 450 tct cgt ctt aag aga aag gca caa gtt cct ggt ttc gtg gaa gag gtg    1446
Ser Arg Leu Lys Arg Lys Ala Gln Val Pro Gly Phe Val Glu Glu Val
455                 460                 465                 470 aag tat tct gcg tct gaa cag tta gat att taaagtaaga aagaatttta    1496
Lys Tyr Ser Ala Ser Glu Gln Leu Asp Ile
                475                 480 agattaaatg ttttcattc ctaagattat gaatttgttt taatctttaa aaaaaaaaa    1556 aaaaaaaaaa aaaaaaaaaa aaaaaaaaaa aaaaaa                            1592

<210> SEQ ID NO 7
<211> LENGTH: 480
<212> TYPE: PRT
<213> ORGANISM: Glycine max

<400> SEQUENCE: 7

Met Ala Ala Thr Glu Ser Thr Val Thr Ser Asn Pro Ser Asn Arg Glu
1               5                   10                  15

Arg Pro Lys Pro Lys Pro Lys Leu Leu Val Ile Thr Gly Pro Thr Ala
            20                  25                  30

Ser Gly Lys Ser Lys Leu Ala Val Asp Leu Ala Ser His Phe Pro Val
        35                  40                  45

Glu Leu Ile Asn Ala Asp Ser Met Gln Val Tyr Arg Gly Leu Asp Val
    50                  55                  60

Leu Thr Asn Lys Leu Pro Leu Ser His Gln Asn Gly Val Pro His His
65                  70                  75                  80

Leu Leu Gly Thr Val Ser Pro Asn Val Glu Phe Thr Ala Lys Ala Phe
                85                  90                  95

Arg Asp Ser Ala Ile Pro Ile Ile Asp Asp Ile Leu Ala Arg Asn His
            100                 105                 110

Leu Pro Val Ile Val Gly Gly Thr Asn Tyr Tyr Ile Gln Ala Leu Val
```

```
                115                 120                 125
Ser Pro Phe Leu Leu Asp Asp Ser Ala Glu Asp Met Asp Glu Ser Cys
            130                 135                 140

Leu Gly Asp Pro Thr Gly Ser Gly Asn Asn Phe Ile Gly Glu Asn Asp
145                 150                 155                 160

Cys Ser Asn Asn Ser Tyr Asp Leu Leu Lys Asp Ile Asp Pro Val Ala
                165                 170                 175

Ala Asn Arg Ile His Pro Asn Asn His Arg Lys Ile Asn Gln Tyr Ile
            180                 185                 190

Asn Leu Tyr Asn Arg Thr Gly Val Leu Pro Ser Asn Ile Phe Gln Gly
        195                 200                 205

Lys Ala Ala Glu Gly Gln Lys Trp Gly Gln Val Asp Asn Leu Arg Tyr
    210                 215                 220

Asp Cys Cys Phe Ile Cys Val Asp Ala Ser Leu Pro Val Leu Asp Arg
225                 230                 235                 240

Tyr Val Glu Gln Arg Val Asp Cys Met Met His Glu Gly Leu Leu Asn
                245                 250                 255

Glu Val Tyr Asp Ile Tyr Asn Leu Asn Ala Val Tyr Thr Arg Gly Leu
            260                 265                 270

Arg Gln Ala Ile Gly Val Arg Glu Phe Glu Pro Leu Leu Arg Thr Cys
        275                 280                 285

Val Val Lys Asp Met His Glu Arg Glu Arg Glu Leu Thr Glu Gly Ser
    290                 295                 300

Ser Ile Glu Lys Gly Glu Thr Leu Phe Asn His Asn Leu Met Glu Leu
305                 310                 315                 320

Val Arg Ser Ser Asn Thr Glu Ser Thr Ile Leu Glu Glu Ala
                325                 330                 335

Ile Glu Lys Val Lys Leu Asn Thr Arg Arg Leu Ile Arg Arg Gln Lys
            340                 345                 350

Arg Met Leu Ser Arg Leu Gln Thr Leu Phe Gly Trp Asn Ile His Tyr
        355                 360                 365

Val Asp Ser Thr Glu Ser Ile Ser Ser Lys Ser Glu Asp Val Trp Thr
    370                 375                 380

Arg Gln Val Val Glu Ser Ala Val Lys Ile Val Lys Ser Phe Leu Ser
385                 390                 395                 400

Glu Asn Gly Thr Ile Phe Gly Thr Ser Asn Asp Thr Gly Met Lys Ile
                405                 410                 415

Ile Gln Arg Asp Leu Trp Thr Gln Tyr Ile Cys Lys Ala Cys Gly Asp
            420                 425                 430

Arg Val Leu Arg Gly Phe His Glu Trp Glu Gln His Arg Gln Gly Arg
        435                 440                 445

Gly His Arg Lys Arg Ile Ser Arg Leu Lys Arg Lys Ala Gln Val Pro
    450                 455                 460

Gly Phe Val Glu Glu Val Lys Tyr Ser Ala Ser Glu Gln Leu Asp Ile
465                 470                 475                 480

<210> SEQ ID NO 8
<211> LENGTH: 322
<212> TYPE: PRT
<213> ORGANISM: Zea mays
<220> FEATURE:
<221> NAME/KEY: PEPTIDE
<222> LOCATION: (1)...(322)
<223> OTHER INFORMATION: ZmIPT2

<400> SEQUENCE: 8
```

```
Met Glu His Gly Ala Val Ala Gly Lys Pro Lys Val Val Phe Val Leu
1               5                   10                  15

Gly Ala Thr Ala Thr Gly Lys Ser Lys Leu Ala Ile Ala Leu Ala Glu
                20                  25                  30

Arg Phe Asn Gly Glu Val Ile Asn Ala Asp Lys Ile Gln Val His Asp
            35                  40                  45

Gly Val Pro Ile Ile Thr Asn Lys Val Thr Glu Glu Gln Gly Gly
    50                  55                  60

Val Pro His His Leu Leu Ser Val Arg His Pro Asp Ala Asp Phe Thr
65              70                  75                  80

Ala Glu Glu Phe Arg Arg Glu Ala Ala Ser Ala Val Ala Arg Val Leu
                85                  90                  95

Ser Ala Gly Arg Leu Pro Val Val Ala Gly Ser Asn Thr Tyr Ile
            100                 105                 110

Glu Ala Leu Val Glu Gly Asp Gly Ala Ala Phe Arg Ala Ala His Asp
            115                 120                 125

Leu Leu Phe Val Trp Val Asp Ala Glu Gln Glu Leu Leu Glu Trp Tyr
    130                 135                 140

Ala Ala Leu Arg Val Asp Glu Met Val Ala Arg Gly Leu Val Ser Glu
145                 150                 155                 160

Ala Arg Ala Ala Phe Gly Gly Ala Gly Val Asp Tyr Asn His Gly Val
                165                 170                 175

Arg Arg Ala Ile Gly Leu Pro Glu Met His Ala Tyr Leu Val Ala Glu
            180                 185                 190

Arg Glu Gly Val Ala Gly Glu Ala Glu Leu Ala Ala Met Leu Glu Arg
            195                 200                 205

Ala Val Arg Glu Ile Lys Asp Asn Thr Phe Arg Leu Ala Arg Thr Gln
210                 215                 220

Ala Glu Lys Ile Arg Arg Leu Ser Thr Leu Asp Gly Trp Asp Val Arg
225                 230                 235                 240

Arg Ile Asp Val Thr Pro Val Phe Ala Arg Lys Ala Asp Gly Thr Glu
                245                 250                 255

Cys His Glu Leu Thr Trp Lys Lys Gln Val Trp Glu Pro Cys Glu Glu
            260                 265                 270

Met Val Arg Ala Phe Leu Glu Pro Ser Leu Thr Ala Val Pro Gly Val
            275                 280                 285

Ala Val Thr Glu Glu Gly Asn Ala Gly Val Val Ala Thr Ala Ala Pro
290                 295                 300

Ala Gly Asp Val Val Val Pro Thr Gly Asp Val Val Thr Ala Val Ala
305                 310                 315                 320

Asp Ala

<210> SEQ ID NO 9
<211> LENGTH: 92
<212> TYPE: PRT
<213> ORGANISM: Artificial Sequence
<220> FEATURE:
<223> OTHER INFORMATION: cytokinin biosynthetic enzyme consensus
      sequence
<220> FEATURE:
<221> NAME/KEY: VARIANT
<222> LOCATION: (8)...(8)
<223> OTHER INFORMATION: The amino acid at position 8 can also be T.
<220> FEATURE:
<221> NAME/KEY: VARIANT
<222> LOCATION: (14)...(14)
<223> OTHER INFORMATION: The amino acid at position 14 can also be L or
```

```
            I.
<220> FEATURE:
<221> NAME/KEY: VARIANT
<222> LOCATION: (22)...(23)
<223> OTHER INFORMATION: The amino acid at position 22 or 23 can also be
      L or I.
<220> FEATURE:
<221> NAME/KEY: VARIANT
<222> LOCATION: (87)...(88)
<223> OTHER INFORMATION: The amino acid at position 87 or 88 can also be
      L or I.
<220> FEATURE:
<221> NAME/KEY: VARIANT
<222> LOCATION: (92)...(92)
<223> OTHER INFORMATION: The amino acid at position 92 can also be T.
<220> FEATURE:
<221> NAME/KEY: VARIANT
<222> LOCATION: (2)...(89)
<223> OTHER INFORMATION: Xaa = any amino acid

<400> SEQUENCE: 9

Gly Xaa Thr Xaa Xaa Gly Lys Ser Xaa Xaa Xaa Xaa Xaa Val Xaa Xaa
 1               5                  10                  15

Xaa Xaa Xaa Xaa Xaa Val Val Xaa Xaa Asp Xaa Xaa Gln Xaa Xaa Xaa
             20                  25                  30

Xaa Xaa Xaa Xaa Xaa Xaa Xaa Xaa Xaa Xaa Xaa Xaa Xaa Xaa Xaa Xaa
         35                  40                  45

Xaa Xaa Xaa Xaa Xaa Xaa Xaa Xaa Xaa Xaa Xaa Xaa Xaa Xaa Xaa Xaa
     50                  55                  60

Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Val Val Xaa Gly Gly Ser
             85                  90

<210> SEQ ID NO 10
<211> LENGTH: 20
<212> TYPE: DNA
<213> ORGANISM: Artificial Sequence
<220> FEATURE:
<223> OTHER INFORMATION: primer 100066

<400> SEQUENCE: 10
agcgctgtgc aagcccgtag                                               20

<210> SEQ ID NO 11
<211> LENGTH: 21
<212> TYPE: DNA
<213> ORGANISM: Artificial Sequence
<220> FEATURE:
<223> OTHER INFORMATION: primer 100067

<400> SEQUENCE: 11
gatcatgcga tccacacgtg c                                             21

<210> SEQ ID NO 12
<211> LENGTH: 22
<212> TYPE: DNA
<213> ORGANISM: Artificial Sequence
<220> FEATURE:
<223> OTHER INFORMATION: primer 100068

<400> SEQUENCE: 12
gcggtgtgca agcccgtagt ag                                            22

<210> SEQ ID NO 13
<211> LENGTH: 20
```

```
<212> TYPE: DNA
<213> ORGANISM: Artificial Sequence
<220> FEATURE:
<223> OTHER INFORMATION: primer 100069

<400> SEQUENCE: 13
agggacgcct atggcctttc                                              20

<210> SEQ ID NO 14
<211> LENGTH: 17
<212> TYPE: DNA
<213> ORGANISM: Artificial Sequence
<220> FEATURE:
<223> OTHER INFORMATION: expression profiling tag

<400> SEQUENCE: 14
gatcatcctc cacaagt                                                 17

<210> SEQ ID NO 15
<211> LENGTH: 17
<212> TYPE: DNA
<213> ORGANISM: Artificial Sequence
<220> FEATURE:
<223> OTHER INFORMATION: expression profiling tag

<400> SEQUENCE: 15
gatcacgtgt tgtccaa                                                 17

<210> SEQ ID NO 16
<211> LENGTH: 17
<212> TYPE: DNA
<213> ORGANISM: Artificial Sequence
<220> FEATURE:
<223> OTHER INFORMATION: Lynx tag for GmIPT3

<400> SEQUENCE: 16
gatcgtgtgc ttagagg                                                 17

<210> SEQ ID NO 17
<211> LENGTH: 9
<212> TYPE: PRT
<213> ORGANISM: Artificial Sequence
<220> FEATURE:
<223> OTHER INFORMATION: motif
<220> FEATURE:
<221> NAME/KEY: VARIANT
<222> LOCATION: (8)...(8)
<223> OTHER INFORMATION: may be M

<400> SEQUENCE: 17

Glu Ile Ile Asn Ser Asp Lys Ile Gln
 1               5

<210> SEQ ID NO 18
<211> LENGTH: 26
<212> TYPE: DNA
<213> ORGANISM: Artificial Sequence
<220> FEATURE:
<223> OTHER INFORMATION: sense degenerate primer
<220> FEATURE:
<221> NAME/KEY: misc_feature
<222> LOCATION: 15, 24
<223> OTHER INFORMATION: n = Inosine

<400> SEQUENCE: 18
garathatha aywsngayaa ratnca                                       26
```

```
<210> SEQ ID NO 19
<211> LENGTH: 26
<212> TYPE: DNA
<213> ORGANISM: Artificial Sequence
<220> FEATURE:
<223> OTHER INFORMATION: antisense degenerate primer for SEQ 17
<220> FEATURE:
<221> NAME/KEY: misc_feature
<222> LOCATION: 3, 12
<223> OTHER INFORMATION: n = Inosine

<400> SEQUENCE: 19
tgnatyttrt cnswrttdat datytc                                          26

<210> SEQ ID NO 20
<211> LENGTH: 8
<212> TYPE: PRT
<213> ORGANISM: Artificial Sequence
<220> FEATURE:
<223> OTHER INFORMATION: motif

<400> SEQUENCE: 20

Gly Val Pro His His Leu Leu Gly
 1               5

<210> SEQ ID NO 21
<211> LENGTH: 23
<212> TYPE: DNA
<213> ORGANISM: Artificial Sequence
<220> FEATURE:
<223> OTHER INFORMATION: sense degenerate primer for SEQ ID 20
<220> FEATURE:
<221> NAME/KEY: misc_feature
<222> LOCATION: 3, 6, 9, 18, 21
<223> OTHER INFORMATION: n = inosine

<400> SEQUENCE: 21
ggngtnccnc aycayytnyt ngg                                             23

<210> SEQ ID NO 22
<211> LENGTH: 23
<212> TYPE: DNA
<213> ORGANISM: Artificial Sequence
<220> FEATURE:
<223> OTHER INFORMATION: antisense degenerate primer for SEQ ID 20
<220> FEATURE:
<221> NAME/KEY: misc_feature
<222> LOCATION: 3, 6, 15, 18, 21
<223> OTHER INFORMATION: n = inosine

<400> SEQUENCE: 22
ccnarnarrt grtgnggnac ncc                                             23

<210> SEQ ID NO 23
<211> LENGTH: 7
<212> TYPE: PRT
<213> ORGANISM: Artificial Sequence
<220> FEATURE:
<223> OTHER INFORMATION: motif

<400> SEQUENCE: 23

Gly Val Pro His His Leu Leu
 1               5

<210> SEQ ID NO 24
<211> LENGTH: 20
<212> TYPE: DNA
<213> ORGANISM: Artificial Sequence
<220> FEATURE:
```

<223> OTHER INFORMATION: sense degenerate primer for SEQ ID NO: 23
<220> FEATURE:
<221> NAME/KEY: misc_feature
<222> LOCATION: 3, 6, 9, 18
<223> OTHER INFORMATION: n = inosine

<400> SEQUENCE: 24
ggngtnccnc aycayytnyt                                                   20

<210> SEQ ID NO 25
<211> LENGTH: 21
<212> TYPE: DNA
<213> ORGANISM: Artificial Sequence
<220> FEATURE:
<223> OTHER INFORMATION: antisense degenerate primer for SEQ ID NO: 23
<220> FEATURE:
<221> NAME/KEY: misc_feature
<222> LOCATION: 1, 4, 13, 16, 19
<223> OTHER INFORMATION: n = inosine

<400> SEQUENCE: 25
narnarrtgr tgnggnacnc c                                                 21

<210> SEQ ID NO 26
<211> LENGTH: 5
<212> TYPE: PRT
<213> ORGANISM: Artificial Sequence
<220> FEATURE:
<223> OTHER INFORMATION: motif

<400> SEQUENCE: 26

Ala Gly Gly Ser Asn
 1               5

<210> SEQ ID NO 27
<211> LENGTH: 15
<212> TYPE: DNA
<213> ORGANISM: Artificial Sequence
<220> FEATURE:
<223> OTHER INFORMATION: sense degenerate primer for SEQ ID NO: 26
<220> FEATURE:
<221> NAME/KEY: misc_feature
<222> LOCATION: 3, 6, 9, 12
<223> OTHER INFORMATION: n = inosine

<400> SEQUENCE: 27
gcnggnggnw snaay                                                        15

<210> SEQ ID NO 28
<211> LENGTH: 15
<212> TYPE: DNA
<213> ORGANISM: Artificial Sequence
<220> FEATURE:
<223> OTHER INFORMATION: antisense degenerate primer for SEQ ID NO: 26
<220> FEATURE:
<221> NAME/KEY: misc_feature
<222> LOCATION: 4, 7, 10, 13
<223> OTHER INFORMATION: n = inosine

<400> SEQUENCE: 28
rttnswnccn ccngc                                                        15

<210> SEQ ID NO 29
<211> LENGTH: 7
<212> TYPE: PRT
<213> ORGANISM: Artificial Sequence
<220> FEATURE:
<223> OTHER INFORMATION: motif
<220> FEATURE:

```
<221> NAME/KEY: VARIANT
<222> LOCATION: (1)...(1)
<223> OTHER INFORMATION: may be V
<220> FEATURE:
<221> NAME/KEY: VARIANT
<222> LOCATION: (7)...(7)
<223> OTHER INFORMATION: may be F

<400> SEQUENCE: 29

Ala Gly Gly Ser Asn Ser Tyr
 1               5

<210> SEQ ID NO 30
<211> LENGTH: 21
<212> TYPE: DNA
<213> ORGANISM: Artificial Sequence
<220> FEATURE:
<223> OTHER INFORMATION: sense degenerate primer for SEQ ID NO: 29
<220> FEATURE:
<221> NAME/KEY: misc_feature
<222> LOCATION: 3, 6, 9, 12, 18
<223> OTHER INFORMATION: n = inosine

<400> SEQUENCE: 30
gynggnggnw snaaywsntw y                                          21

<210> SEQ ID NO 31
<211> LENGTH: 21
<212> TYPE: DNA
<213> ORGANISM: Artificial Sequence
<220> FEATURE:
<223> OTHER INFORMATION: antisense degenerate primer for SEQ ID NO: 29
<220> FEATURE:
<221> NAME/KEY: misc_feature
<222> LOCATION: 4, 10, 13, 16, 19
<223> OTHER INFORMATION: n = inosine

<400> SEQUENCE: 31
rwanswrttn swnccnccnr c                                          21

<210> SEQ ID NO 32
<211> LENGTH: 8
<212> TYPE: PRT
<213> ORGANISM: Artificial Sequence
<220> FEATURE:
<223> OTHER INFORMATION: motif
<220> FEATURE:
<221> NAME/KEY: VARIANT
<222> LOCATION: (4)...(4)
<223> OTHER INFORMATION: may be L

<400> SEQUENCE: 32

Cys Cys Phe Ile Trp Val Asp Val
 1               5

<210> SEQ ID NO 33
<211> LENGTH: 23
<212> TYPE: DNA
<213> ORGANISM: Artificial Sequence
<220> FEATURE:
<223> OTHER INFORMATION: sense degenerate primer for SEQ ID NO: 32
<220> FEATURE:
<221> NAME/KEY: misc_feature
<222> LOCATION: 12, 18
<223> OTHER INFORMATION: n = inosine

<400> SEQUENCE: 33
tgytgyttyh tntgggtnga ygt                                        23
```

```
-continued
<210> SEQ ID NO 34
<211> LENGTH: 23
<212> TYPE: DNA
<213> ORGANISM: Artificial Sequence
<220> FEATURE:
<223> OTHER INFORMATION: antisense degenerate primer for SEQ ID NO: 32
<220> FEATURE:
<221> NAME/KEY: misc_feature
<222> LOCATION: 6, 12
<223> OTHER INFORMATION: n = inosine

<400> SEQUENCE: 34
acrtcnaccc anadraarca rca                                              23
```

SOYBEAN ISOPENTENYL TRANSFERASE GENES AND METHODS OF USE

CROSS REFERENCE

This application is a divisional of U.S. patent application Ser. No. 11/669,281 filed Jan. 31, 2007, now issued as U.S. Pat. No. 7,553,951, which claims the benefit of U.S. Provisional Patent Application Ser. No. 60/764,303, filed Feb. 1, 2006, both of which are incorporated herein by reference.

FIELD OF THE INVENTION

The invention relates to the field of genetic manipulation of plants, particularly the modulation of gene activity to affect plant development and growth.

BACKGROUND OF THE INVENTION

Cytokinins are a class of $N^6$ substituted purine derivative plant hormones that regulate cell division and influence a large number of developmental events, such as shoot development, sink strength, root branching, control of apical dominance in the shoot, leaf development, chloroplast development and leaf senescence (Mok, et al., (1994) *Cytokinins. Chemistry, Action and Function*. CRC Press, Boca Raton, Fla., pp 155-166; Horgan, (1984) *Advanced Plant Physiology* ed. MB., Pitman, London, UK, pp 53-75 and Letham, (1994) *Annual Review of Plant Physiol* 34:163-197). In maize, cytokinins (CK) play an important role in establishing seed size, decreasing tip kernel abortion and increasing seed set during unfavorable environmental conditions (Cheikh, et al., (1994) *Plant Physiol.* 106:45-51; Dietrich, et al., (1995) *Plant Physiol Biochem* 33:327-36). Active cytokinin pools are regulated by rates of synthesis and degradation.

Until recently, roots were believed to be the major site of cytokinin biosynthesis but evidence indicates that others tissues, such as shoot meristems and developing seeds, also have high cytokinin biosynthetic activity. It has been suggested that cytokinins are synthesized in restricted sites where cell proliferation is active. The presence of several AtIPT genes in *Arabidopsis* and their differential pattern of expression might serve this purpose.

The catabolic enzyme isopentenyl transferase (IPT) directs the synthesis of cytokinins and plays a major role in controlling cytokinin levels in plant tissues. Multiple routes have been proposed for cytokinin biosynthesis. Transfer RNA degradation has been suggested to be a source of cytokinin, because some tRNA molecules contain an isopentenyladenosine (iPA) residue at the site adjacent to the anticodon (Swaminathan, et al., (1977) *Biochemistry* 16:1355-1360). The modification is catalyzed by tRNA isopentenyl transferase (tRNA IPT; EC 2.5.1.8), which has been identified in various organisms such as *Escherichia coli, Saccharomyces cerevisiae, Lactobacillus acidophilus, Homo sapiens* and *Zea mays* (Bartz, et al., (1972) *Biochemie* 54:31-39; Kline, et al., (1969) *Biochemistry* 8:4361-4371; Holtz, et al., (1975) *Hoppe-Seyler's Z. Physiol. Chem.* 356:1459-1464; Golovko, et al., (2000) *Gene* 258:85-93 and Holtz, et al., (1979) *Hoppe-Seyler's Z. Physiol. Chem.* 359:89-101). However, this pathway is not considered to be the main route for cytokinin synthesis (Chen, et al., (1997) *Physiol. Plant* 101:665-673 and McGraw, et al., (1995) *Plant Hormones, Physiology, Biochemistry and Molecular Biology* Ed. Davies, 98-117, Kluwer Academic Publishers, Dordrecht).

Another possible route of cytokinin formation is de novo biosynthesis of iPMP by adenylate isopentenyl transferase (IPT; EC 2.5.1.27) with dimethylallyl-diphosphate (DMAPP), AMP, ATP and ADP as substrates. Our current knowledge of cytokinin biosynthesis in plants is largely deduced from studies on a possible analogous system in *Agrobacterium tumefaciens*. Cells of *A. tumefaciens* are able to infect certain plant species by inducing tumor formation in host plant tissues (Van Montagu, et al., (1982) *Curr Top Microbiol Immunol* 96:237-254; Hansen, et al., (1999). *Curr Top Microbiol Immunol* 240:21-57). To do so, the *A. tumefaciens* cells synthesize and secrete cytokinins which mediate the transformation of normal host plant tissues into tumors or calli. This process is facilitated by the *A. tumefaciens* tumor-inducing plasmid which contains genes encoding the necessary enzyme and regulators for cytokinin biosynthesis. Biochemical and genetic studies revealed that Gene 4 of the tumor-inducing plasmid encodes an isopentenyl transferase (IPT), which converts AMP and DMAPP into isopentenyladenosine-5'-monophosphate (iPMP), the active form of cytokinins (Akiyoshi, et al., (1984) *Proc. Natl. Acad. Sci. USA* 81:5994-5998). Overexpression of the *Agrobacterium* ipt gene in a variety of transgenic plants has been shown to cause an increased level of cytokinins and elicit typical cytokinin responses in the host plant (Hansen, et al., (1999) *Curr Top Microbiol Immunol* 240:21-57). Therefore, it has been postulated that plant cells use machinery similar to that of *A. tumefaciens* cells for cytokinin biosynthesis. *Arabidopsis* IPT homologs have recently been identified in *Arabidopsis* and *Petunia* (Takei, et al., (2001) *J. Biol. Chem.* 276:26405-26410 and Kakimoto, (2001) *Plant Cell Physiol.* 42:677-685). Overexpression of the *Arabidopsis* IPT homologs in plants elevated cytokinin levels and elicited typical cytokinin responses in planta and under tissue culture conditions (Kakimoto, (2001) *Plant Cell Physiol.* 42:677-685).

*Arabidopsis* ipt genes are members of a small multigene family of nine different genes, two of which code for tRNA isopentenyl transferases, and seven of which encode a gene product with a cytokinin biosynthetic function. Biochemical analysis of the recombinant AtIPT4 protein showed that, in contrast to the bacterial enzyme, the *Arabidopsis* enzyme uses ATP as a substrate instead of AMP. Another plant IPT gene (Sho) was identified in *Petunia hybrida* using an activation tagging strategy (Zubko, et al., (2002) *The Plant Journal* 29:797-808).

In view of the influence of cytokinins on a wide variety of plant developmental processes, including root architecture, shoot and leaf development, and seed set, the ability to manipulate cytokinin levels in higher plant cells, and thereby drastically effect plant growth and productivity, offers significant commercial value (Mok, et al., (1994) *Cytokinins. Chemistry, Action and Function*. CRC Press, Boca Raton, Fla., pp. 155-166).

BRIEF SUMMARY OF THE INVENTION

Compositions and methods of the invention comprise and employ isopentenyl transferase (IPT) polypeptides and polynucleotides that are involved in modulating plant development, morphology, and physiology.

Compositions further include expression cassettes, plants, plant cells and seeds having the IPT sequences of the invention. The plants, plant cells and seeds of the invention may exhibit phenotypic changes, such as modulated (increased or decreased) cytokinin levels; modulated floral development; modulated root development; altered shoot to root ratio; increased seed size or an increased seed weight; increased plant yield or plant vigor; maintained or improved stress tolerance (e.g., increased or maintained size of the plant, minimized seed or pod abortion, increased or maintained seed set); decreased shoot growth; delayed senescence or an enhanced vegetative growth, all relative to a plant, plant cell or seed not modified per the invention.

Methods are provided for reducing or eliminating the activity of an IPT polypeptide in a plant, comprising introducing into the plant a selected polynucleotide. In specific methods, providing the polynucleotide decreases the level of cytokinin in the plant and/or modulates root development of the plant.

Methods are also provided for increasing the level of an IPT polypeptide in a plant comprising introducing into the plant a selected polynucleotide. In specific methods, expression of the IPT polynucleotide increases the level of a cytokinin in the plant; maintains or improves the stress tolerance of the plant; maintains or increases the size of the plant; minimizes seed abortion; increases or maintains seed set; increases shoot growth; increases seed size or seed weight; increases plant yield or plant vigor; modulates floral development; delays senescence; or increases leaf growth.

BRIEF DESCRIPTION OF THE DRAWINGS

FIG. 1 provides an alignment of amino acid sequences of ZmIPT2 (SEQ ID NO: 8), GmIPT1 (SEQ ID NO: 2), GmIPT2 (SEQ ID NO: 4) and GmIPT3 (SEQ ID NO: 7). Asterisks indicate amino acids conserved in many IPT proteins, and the derived IPT consensus sequence is set out below the alignment. A motif characteristic of tRNA IPT was found in GmIPT3.

FIG. 2 provides percent identity and percent similarity values for GmIPT1, GmIPT2, GmIPT3, ZmIPT2, and *Arabidopsis* IPT1-IPT9.

FIG. 3 is a Northern blot showing relative levels of expression of GmIPT1 (Panel A) and GmIPT2 (Panel B) in various soybean tissues.

FIG. 4 is a phylogenetic tree of plant IPT sequences. GmIPT1 and GmIPT2 are clustered with other plant IPT proteins whereas GmIPT3 clusters with AtIPT2 which is a tRNA IPT.

BRIEF DESCRIPTION OF THE SEQUENCES

SEQ ID NO: 1 and 2 provide nucleotide and amino acid sequences for GmIPT1.

SEQ ID NO: 3 and 4 provide nucleotide and amino acid sequences for GmIPT2.

SEQ ID NO: 5 provides the full insert sequence for the GmIPT2 EST initially identified.

SEQ ID NO: 6 and 7 provide nucleotide and amino acid sequences for GmIPT3.

SEQ ID NO: 8 provides the ZmIPT2 amino acid sequence.

SEQ ID NO: 9 is a consensus IPT sequence.

SEQ ID NOS: 10-13 are primer sequences used in BAC screening.

SEQ ID NOS: 14-16 are tags used in expression profiling.

DETAILED DESCRIPTION OF THE INVENTION

The present invention now will be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the invention set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Compositions

Compositions of the invention include isopentenyl transferase (IPT) polypeptides and polynucleotides that are involved in modulating plant development, morphology, and physiology. In particular, the present invention provides for isolated polynucleotides comprising nucleotide sequences encoding the amino acid sequences shown in SEQ ID NO: 2, 4 and 7. Further provided are isolated polypeptides having an amino acid sequence encoded by a polynucleotide described herein, for example those set forth in SEQ ID NO: 1, 3 and 6.

The isopentenyl transferase polypeptides of the invention share sequence identity with members of the isopentenyl transferase family of proteins. Polypeptides in the IPT family have been identified in various bacteria and in *Arabidopsis* and *Petunia*. See, for example, Kakimoto, (2001) *Plant Cell Physio.* 42:677-658; Takei, et al., (2001) *The Journal of Biological Chemistry* 276:26405-26410 and Zubko, et al., (2002) *The Plant Journal* 29:797-808. Members of the IPT family are characterized by having the consensus sequence GxTxxGK[ST]xxxxx[VLI]xxxxxxx[VLI][VLI] xxDxxQx{57,60}[VLI][VLI]xGG[ST] (SEQ ID NO: 9) (where x denotes any amino acid residue, [ ] any one of the amino acids shown in [ ], and x{m,n} m to n amino acid residues in number). See, Kakimoto, et al., (2001) *Plant Cell Physiol.* 42:677-85 and Kakimoto, et al., (2003) *J. Plant Res.* 116:233-9, both of which are herein incorporated by reference. IPT family members may also have ATP/GTP binding sites. An amino acid alignment of the maize IPT2 protein along with soy (*Glycine max*) cytokinin biosynthetic enzymes of the invention is provided in FIG. 1. Asterisks indicate a consensus sequence found in many cytokinin biosynthetic enzymes. In addition to this consensus sequence, a tRNA binding site was identified in GmIPT3 which suggests that the gene encodes a tRNA IPT enzyme.

Isopentenyl transferase enzymes are involved in cytokinin biosynthesis, therefore the IPT polypeptides of the invention have "cytokinin synthesis activity." By "cytokinin synthesis activity" is intended enzymatic activity that generates cytokinins, derivatives thereof, or any intermediates in the cytokinin synthesis pathway. Cytokinin synthesis activity therefore includes, but is not limited to, DMAPP:AMP isopentenyltransferase activity (the conversion of AMP (adenosine-5'-monophosphate) and DMAPP into iPMP (isopentenyladenosine-5'-monophosphate)), DMAPP:ADP isopentenyltransferase activity (the conversion of ADP (adenosine-5'-diphosphate) and DMAPP into iPDP (isopentenyladenosine-5'-diphosphate)); DMAPP:ATP isopentenyltransferase activity (the conversion of ATP (adenosine-5'-triphosphate) and DMAPP into iPTP (isopentenyladenosine-5'-triphosphate)), and DMAPP:tRNA isopentenyltransferase activity (the modification of cytoplasmic, chloroplastic and/or mitochondrial tRNAs to give isopentenyl). Cytokinin synthesis activity can further include a substrate comprising a second side chain precursor, other than DMAPP. Examples of side chain donors include compounds of terpenoid origin. For example, the substrate could be hydroxymethylbutenyl diphosphate (HMBPP) which would allow trans-zeatin riboside monophosphate (ZMP) synthesis. See, for example, Åstot, et al., (2000) *Proc Natl Acad Sci* 97:14778-14783 and Takei, et al., (2003) *J Plant Res.* 116(3):265-9.

Cytokinin synthesis activity further includes the synthesis of intermediates involved in formation of ZMP. Methods to assay for the production of various cytokinins and their intermediates can be found, for example, in Takei, et al., (2001) *The Journal of Biological Chemistry* 276:26405-26410; Zubo, et al., (2002) *The Plant Journal* 29:797-808; Kakimoto, et al., (2001) *Plant Cell Physio.* 42:677-658 and Sun, et al., (2003) *Plant Physiology* 131:167-176, each of which is herein incorporated by reference. "Cytokinin synthesis activity" also includes any alteration in a plant or plant cell phenotype that is characteristic of an increase in cytokinin concentration. Such cytokinin specific effects are discussed elsewhere herein and include, but are not limited to, enhanced shoot formation, reduced apical dominance, delayed senescence, delayed flowering, increased leaf growth, increased cytokinin levels in the plant, increased tolerance under stress, minimization of pod and/or seed abortion, increased or maintained seed set under stress conditions and a decrease in root growth. Assays to measure or detect such phenotypes are known. See, for example, Miyawaki, et al., (2004) *The Plant Journal* 37:128-138, Takei, et al., (2001) *The Journal of Biological Chemistry* 276:26405-26410, Zubo, et al., (2002) *The Plant Journal* 29:797-808; Kakimoto, et al., (2001) *Plant Cell Physio.* 42:677-658, and Sun, et al., (2003) *Plant Physiology* 131:167-176, each of which is herein incorporated by reference. Additional phenotypes resulting from an increase in cytokinin synthesis activity in a plant are discussed herein.

Compositions of the invention include IPT sequences that are involved in cytokinin biosynthesis. In particular, the present invention provides for isolated polynucleotides comprising nucleotide sequences encoding the amino acid sequences shown in SEQ ID NO: 2, 4 and 7. Further provided are polypeptides having an amino acid sequence encoded by a polynucleotide described herein, for example those set forth in SEQ ID NOS: 1, 3 and 6, and fragments and variants thereof.

The invention encompasses isolated or substantially purified polynucleotide or protein compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material, or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5% or 1% (by dry weight) of contaminating protein. When the protein of the invention or biologically active portion thereof is recombinantly produced, optimally culture medium represents less than about 30%, 20%, 10%, 5% or 1% (by dry weight) of chemical precursors or non-protein-of-interest chemicals.

Fragments and variants of the disclosed polynucleotides and proteins encoded thereby are also encompassed by the present invention. By "fragment" is intended a portion of the polynucleotide or a portion of the amino acid sequence and hence protein encoded thereby. Fragments of a polynucleotide may encode protein fragments that retain the biological activity of the native protein and hence have cytokinin synthesis activity. Alternatively, fragments of a polynucleotide that are useful as hybridization probes generally do not encode fragment proteins retaining biological activity. Thus, fragments of a nucleotide sequence may range from at least about 20 nucleotides, about 50 nucleotides, about 100 nucleotides and up to the full-length polynucleotide encoding the proteins of the invention.

A fragment of an IPT polynucleotide that encodes a biologically active portion of an IPT protein of the invention will encode at least 15, 25, 30, 50, 100, 150, 200, 225, 250, 275, 300, 310, 315 or 320 contiguous amino acids, or up to the total number of amino acids present in a full-length IPT protein of the invention (for example, 340 amino acids for SEQ ID NO: 2 or 4; 480 amino acids for SEQ ID NO: 7). Fragments of an IPT polynucleotide that are useful as hybridization probes or PCR primers generally need not encode a biologically active portion of an IPT protein.

Thus, a fragment of an IPT polynucleotide may encode a biologically active portion of an IPT protein, or it may be a fragment that can be used as a hybridization probe or PCR primer using methods disclosed below. A biologically active portion of an IPT protein can be prepared by isolating a portion of one of the IPT polynucleotides of the invention, expressing the encoded portion of the IPT protein (e.g., by recombinant expression in vitro), and assessing the activity of the encoded portion of the IPT protein. Polynucleotides that are fragments of an IPT nucleotide sequence comprise at least 16, 20, 50, 75, 100, 150, 200, 250, 300, 350, 400, 450, 500, 550, 600, 650, 700, 800, 900, 950 or 965 contiguous nucleotides, or up to the number of nucleotides present in a full-length IPT polynucleotide disclosed herein (for example, 1023, 1409, and 1592 nucleotides for SEQ ID NO: 1, 3 and 6, respectively).

"Variants" is intended to mean substantially similar sequences. For polynucleotides, a variant comprises a deletion and/or addition of one or more nucleotides at one or more sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the IPT polypeptides of the invention. Naturally occurring variants such as these can be identified with the use of well-known molecular biology techniques, as, for example, with polymerase chain reaction (PCR) and hybridization techniques as outlined below. Variant polynucleotides also include synthetically derived polynucleotide, such as those generated, for example, by using site-directed mutagenesis but which still encode an IPT protein of the invention. Generally, variants of a particular polynucleotide of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Thus, for example, isolated polynucleotides that encode a polypeptide with a given percent sequence identity to the polypeptide of SEQ ID NO: 2, 4 or 7 are disclosed. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

"Variant" protein is intended to mean a protein derived from the native protein by deletion or addition of one or more amino acids at one or more sites in the native protein and/or substitution of one or more amino acids at one or more sites in the native protein. Certain variant proteins encompassed by the present invention are biologically active, that is they continue to possess the desired biological activity of the native protein, that is, cytokinin synthesis activity, as described herein. Such variants may result from, for example, genetic polymorphism or from human manipulation. Biologically active variants of a native IPT protein of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein of the invention may differ from that protein by as few as 1-15 amino acid residues, as few as 1-10, such as 6-10, as few as 5, as few as 4, 3, 2 or even 1 amino acid residue.

The proteins of the invention may be altered in various ways including amino acid substitutions, deletions, truncations and insertions. Methods for such manipulations are generally known in the art. For example, amino acid sequence variants and fragments of the IPT proteins can be prepared by mutations in the DNA. Methods for mutagenesis and polynucleotide alterations are well known in the art. See, for example, Kunkel, (1985) *Proc. Natl. Acad. Sci. USA* 82:488-492; Kunkel, et al., (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff, et al., (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Thus, the genes and polynucleotides of the invention include both the naturally occurring sequences as well as mutant forms. Likewise, the proteins of the invention encompass naturally occurring proteins as well as variations and modified forms thereof. Such variants will continue to possess the desired IPT activity. Obviously, the mutations that will be made in the DNA encoding the variant must not place the sequence out of reading frame and optimally will not create complementary regions that could produce secondary mRNA structure.

The deletions, insertions and substitutions of the protein sequences encompassed herein are not expected to produce radical changes in the characteristics of the protein. However, when it is difficult to predict the exact effect of the substitution, deletion or insertion in advance of doing so, one skilled in the art will appreciate that the effect will be evaluated by routine screening assays. That is, the activity can be evaluated by assaying for cytokinin synthesis activity. See, for example, Takei, et al., (2001) *The Journal of Biological Chemistry* 276:26405-26410; Zubo, et al., (2002) *The Plant Journal* 29:797-808; Kakimoto, et al., (2001) *Plant Cell Physio.* 42:677-658; Sun, et al., (2003) *Plant Physiology* 131:167-176 and Miyawaki, et al., (2004) *The Plant Journal* 37:128-138, all of which are herein incorporated by reference.

Variant polynucleotides and proteins also encompass sequences and proteins derived from a mutagenic and recombinogenic procedure such as DNA shuffling. With such a procedure, one or more different IPT coding sequences can be manipulated to create a new IPT polypeptide possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the IPT gene of the invention and other known IPT genes to obtain a new gene coding for a protein with an improved property of interest, such as an increased $K_m$ in the case of an enzyme. Strategies for such DNA shuffling are known in the art. See, for example, Stemmer, (1994) *Proc. Natl. Acad. Sci. USA* 91:10747-10751; Stemmer, (1994) *Nature* 370:389-391; Crameri, et al., (1997) *Nature Biotech.* 15:436-438; Moore, et al., (1997) *J. Mol. Biol.* 272:336-347; Zhang, et al., (1997) *Proc. Natl. Acad. Sci. USA* 94:4504-4509; Crameri, et al., (1998) *Nature* 391:288-291; PCT Publication Number WO97/20078 and U.S. Pat. Nos. 5,605,793 and 5,837,458.

By "promoter" is intended a regulatory region of DNA usually comprising a TATA box capable of directing RNA polymerase II to initiate RNA synthesis at the appropriate transcription initiation site for a particular polynucleotide sequence. A promoter may additionally comprise other recognition sequences generally positioned upstream or 5' to the TATA box, referred to as upstream promoter elements, which influence the transcription initiation rate. The promoter sequences of the present invention regulate (i.e., repress or activate) transcription.

The polynucleotides of the invention can be used to isolate corresponding sequences from other organisms, particularly other plants, more particularly other monocots. In this manner, methods such as PCR, hybridization, and the like can be used to identify such sequences based on their sequence homology to the sequences set forth herein. Sequences isolated based on their sequence identity to the entire IPT sequences set forth herein or to variants and fragments thereof are encompassed by the present invention. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least 60%, 70%, 75%, 80%, 85%, 90%, 91%, 92%, 93%, 94%, 95%, 96%, 97%, 98%, 99% or greater sequence identity. Functions of orthologs are often highly conserved among species. Thus, isolated polynucleotides that encode an IPT protein and which hybridize under stringent conditions to the IPT sequences disclosed herein or to variants or fragments or complements thereof, are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook, et al., (1989) *Molecular Cloning: A Laboratory Manual* (2d ed., Cold Spring Harbor Laboratory Press, Plainview, N.Y.). See also, Innis, et al., eds. (1990) *PCR Protocols: A Guide to Methods and Applications* (Academic Press, New York); Innis and Gelfand, eds. (1995) *PCR Strategies* (Academic Press, New York) and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers and the like.

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$P, or any other detectable marker. Thus, for example, probes for hybridization can be made by labeling synthetic oligonucleotides based on the IPT polynucleotides of the invention. Methods for preparation of probes for hybridization and for construction of cDNA and genomic libraries are generally known in the art and are disclosed in Sambrook, et al., (1989) *Molecular Cloning: A Laboratory Manual* (2d ed., Cold Spring Harbor Laboratory Press, Plainview, N.Y.).

For example, an entire IPT polynucleotide disclosed herein, or one or more portions thereof, may be used as a probe capable of specifically hybridizing to corresponding IPT polynucleotides. To achieve specific hybridization under a variety of conditions, such probes include sequences that are unique among IPT polynucleotide sequences and are optimally at least about 10 nucleotides in length, and most optimally at least about 20 nucleotides in length. Such probes may be used to amplify corresponding IPT polynucleotides from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook, et al., (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the $T_m$ can be approximated from the equation of Meinkoth and Wahl, (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel, et al., eds. (1995) *Current Protocols in Molecular Biology*, Chapter 2 (Greene Publishing and Wiley-Interscience, New York). See, Sambrook, et al., (1989) *Molecular Cloning: A Laboratory Manual* (2d ed., Cold Spring Harbor Laboratory Press, Plainview, N.Y.).

The following terms are used to describe the sequence relationships between two or more polynucleotides or polypeptides: (a) "reference sequence", (b) "comparison window", (c) "sequence identity" and (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100 or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller, (1988) *CABIOS* 4:11-17; the local alignment algorithm of Smith, et al., (1981) *Adv. Appl. Math.* 2:482; the global alignment algorithm of Needleman and Wunsch, (1970) *J. Mol. Biol.* 48:443-453; the search-for-local alignment method of Pearson and Lipman, (1988) *Proc. Natl. Acad. Sci.* 85:2444-2448; the algorithm of Karlin and Altschul, (1990) *Proc. Natl. Acad. Sci. USA* 872264, modified as in Karlin and Altschul, (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins, et al., (1988) *Gene* 73:237-244 (1988); Higgins, et al., (1989) *CABIOS* 5:151-153; Corpet, et al., (1988) *Nucleic Acids Res.* 16:10881-90; Huang, et al., (1992) *CABIOS* 8:155-65 and Pearson, et al., (1994) *Meth. Mol. Biol.* 24:307-331. The ALIGN program is based on the algorithm of Myers and Miller, (1988) supra. A PAM120 weight residue table, a gap length penalty of 12, and a gap penalty of 4 can be used with the ALIGN program when comparing amino acid sequences. The BLAST programs of Altschul, et al., (1990) *J. Mol. Biol.* 215:403 are based on the algorithm of Karlin and Altschul, (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul, et al., (1997) *Nucleic Acids Res.* 25:3389. Alternatively, PSI-BLAST (in BLAST 2.0) can be used to perform an iterated search that detects distant relationships between molecules. See, Altschul, et al., (1997) supra. When utilizing BLAST, Gapped BLAST, PSI-BLAST, the default parameters of the respective programs (e.g., BLASTN for nucleotide sequences, BLASTX for proteins) can be used. See, www.ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3 and the nwsgapdna.cmp scoring matrix; % identity and % similarity for an amino acid sequence using GAP Weight of 8 and Length Weight of 2, and the BLOSUM62 scoring matrix.

GAP uses the algorithm of Needleman and Wunsch, (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see, Henikoff and Henikoff, (1989) *Proc. Natl. Acad. Sci. USA* 89:10915).

(c) As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The invention further provides plants having altered levels and/or activities of the IPT polypeptides of the invention. In some embodiments, the plants of the invention have stably incorporated into their genome the IPT sequences of the invention. In other embodiments, plants that are genetically modified at a genomic locus encoding an IPT polypeptide of the invention are provided. By "native genomic locus" is intended a naturally occurring genomic sequence. The genomic locus may be modified to reduce or eliminate the activity of the IPT polypeptide. The term "genetically modified" as used herein refers to a plant or plant part that is modified in its genetic information by the introduction of one or more foreign polynucleotides and the insertion of the foreign polynucleotide leads to a phenotypic change in the plant. By "phenotypic change" is intended a measurable change in one or more cell functions. For example, plants having a genetic modification at the genomic locus encoding the IPT polypeptide can show reduced or eliminated expression or activity of the IPT polypeptide. Various methods to generate such a genetically modified genomic locus are described elsewhere herein, as are the variety of phenotypes that can result from the modulation of the level/activity of the IPT sequences of the invention.

As used herein, the term plant includes reference to whole plants, plant parts or organs (e.g., leaves, stems, roots), plant cells, and seeds and progeny of same. Plant cell, as used herein, includes, without limitation, cells obtained from or found in seeds, suspension cultures, embryos, meristematic regions, callus tissue, leaves, roots, shoots, gametophytes, sporophytes, pollen and microspores, as well as plant protoplasts and plant cell tissue cultures, plant calli, plant clumps and plant cells that are intact in plants or parts of plants such as embryos, pollen, ovules, seeds, leaves, flowers, branches, fruit, kernels, ears, cobs, husks, stalks, roots, root tips, anthers, grain and the like. As used herein, "grain" refers to the mature seed produced by commercial growers for purposes other than growing or reproducing the species. Progeny, variants and mutants of the regenerated plants are also included within the scope of the invention, provided that these parts comprise the introduced nucleic acid sequences.

Methods

I. Providing Sequences

The sequences of the present invention can be introduced into and expressed in a host cell such as bacteria, yeast, insect, mammalian or optimally plant cells. It is expected that those of skill in the art are knowledgeable in the numerous systems available for the introduction of a polypeptide or a nucleotide sequence of the present invention into a host cell. No attempt to describe in detail the various methods known for providing proteins in prokaryotes or eukaryotes will be made.

By "host cell" is meant a cell which comprises a heterologous nucleic acid sequence of the invention. Host cells may be prokaryotic cells such as *E. coli* or eukaryotic cells such as yeast, insect, amphibian or mammalian cells. Host cells can also be monocotyledonous or dicotyledonous plant cells. In certain embodiments, the monocotyledonous host cell is a maize host cell.

The use of the term "polynucleotide" is not intended to limit the present invention to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures and the like.

The IPT polynucleotides of the invention can be provided in expression cassettes for expression in the plant of interest. The cassette will include 5' and 3' regulatory sequences operably linked to an IPT polynucleotide of the invention. "Operably linked" is intended to mean a functional linkage between two or more elements. For example, an operable linkage between a polynucleotide of interest and a regulatory sequence (i.e., a promoter) is a functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. An expression cassette may be provided with a plurality of restriction sites and/or recombination sites for insertion of the IPT polynucleotide to be under the transcriptional regulation of the regulatory regions. The expression cassette may additionally contain selectable marker genes.

In certain embodiments, the expression cassette will include in the 5'-3' direction of transcription, a transcriptional and translational initiation region (i.e., a promoter), an IPT polynucleotide of the invention, and a transcriptional and translational termination region (i.e., termination region) functional in plants. The regulatory regions (i.e., promoters, transcriptional regulatory regions, and translational termination regions) and/or the IPT polynucleotide of the invention may be native/analogous to the host cell or to each other. Alternatively, the regulatory regions and/or the IPT polynucleotide of the invention may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably-linked polynucleotide. As used herein, a chimeric gene comprises a coding sequence operably linked to a transcription initiation region that is heterologous to the coding sequence.

While heterologous promoters can be used to express the IPT sequences, the native promoter sequences or other IPT promoters may also be used. Such constructs can change expression levels of IPT sequences in the plant or plant cell. Thus, the phenotype of the plant or plant cell can be altered.

The termination region may be native with the transcriptional initiation region, may be native with the operably-linked IPT polynucleotide of interest, may be native with the plant host, or may be derived from another source (i.e., foreign or heterologous with reference to the promoter), the IPT polynucleotide of interest, the plant host, or any combination thereof. Convenient termination regions are available from the Ti-plasmid of *A. tumefaciens*, such as the octopine synthase and nopaline synthase termination regions. See also, Guerineau, et al., (1991) *Mol. Gen. Genet.* 262:141-144; Proudfoot, (1991) *Cell* 64:671-674; Sanfacon, et al., (1991) *Genes Dev.* 5:141-149; Mogen, et al., (1990) *Plant Cell* 2:1261-1272; Munroe, et al., (1990) *Gene* 91:151-158; Ballas, et al., (1989) *Nucleic Acids Res.* 17:7891-7903 and Joshi, et al., (1987) *Nucleic Acids Res.* 15:9627-9639.

Where appropriate, the polynucleotides may be optimized for increased expression in the transformed plant. That is, the polynucleotides can be synthesized using plant-preferred codons for improved expression. See, for example, Campbell and Gowri, (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391 and Murray, et al., (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein, et al., (1989) *Proc. Natl. Acad. Sci. USA* 86:6126-6130); potyvirus leaders, for example, TEV leader (Tobacco Etch Virus) (Gallie, et al., (1995) *Gene* 165(2):233-238), MDMV leader (Maize Dwarf Mosaic Virus) (*Virology* 154:9-20) and human immunoglobulin heavy-chain binding protein (BiP) (Macejak, et al., (1991) *Nature* 353:90-94); untranslated leader from the coat protein mRNA of alfalfa mosaic virus (AMV RNA 4) (Jobling, et al., (1987) *Nature* 325:622-625); tobacco mosaic virus leader (TMV) (Gallie, et al., (1989) in *Molecular Biology of RNA*, ed. Cech (Liss, New York), pp. 237-256) and maize chlorotic mottle virus leader (MCMV) (Lommel, et al., (1991) *Virology* 81:382-385). See also, Della-Cioppa, et al., (1987) *Plant Physiol.* 84:965-968. Other methods known to enhance translation can also be utilized.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones and 2,4-dichlorophenoxyacetate (2,4-D). Additional selectable markers include phenotypic markers such as β-galactosidase and fluorescent proteins such as green fluorescent protein (GFP) (Su, et al., (2004) *Biotechnol Bioeng* 85:610-9 and Fetter, et al., (2004) *Plant Cell* 16:215-28), cyan fluorescent protein (CYP) (Bolte, et al., (2004) *J. Cell Science* 117:943-54 and Kato, et al., (2002) *Plant Physiol* 129:913-42), and yellow fluorescent protein (PhiYFP™ from Evrogen, see, Bolte, et al., (2004) *J. Cell Science* 117:943-54). For additional selectable markers, see generally, Yarranton, (1992) *Curr. Opin. Biotech.* 3:506-511; Christopherson, et al., (1992) *Proc. Natl. Acad. Sci. USA* 89:6314-6318; Yao, et al., (1992) *Cell* 71:63-72; Reznikoff (1992) *Mol. Microbiol.* 6:2419-2422; Barkley, et al., (1980) in *The Operon*, pp. 177-220; Hu, et al., (1987) *Cell* 48:555-566; Brown, et al., (1987) *Cell* 49:603-612; Figge, et al., (1988) *Cell* 52:713-722; Deuschle, et al., (1989) *Proc. Natl. Acad. Aci. USA* 86:5400-5404; Fuerst, et al., (1989) *Proc. Natl. Acad. Sci. USA* 86:2549-2553; Deuschle, et al., (1990) *Science* 248:480-483; Gossen, (1993) Ph.D. Thesis, University of Heidelberg; Reines, et al., (1993) *Proc. Natl. Acad. Sci. USA* 90:1917-1921; Labow, et al., (1990) *Mol. Cell. Biol.* 10:3343-3356; Zambretti, et al., (1992) *Proc. Natl. Acad. Sci. USA* 89:3952-3956; Baim, et al., (1991) *Proc. Natl. Acad. Sci. USA* 88:5072-5076; Wyborski, et al., (1991) *Nucleic Acids Res.* 19:4647-4653; Hillenand-Wissman, (1989) *Topics Mol. Struc. Biol.* 10:143-162; Degenkolb, et al., (1991) *Antimicrob. Agents Chemother.* 35:1591-1595; Kleinschnidt, et al., (1988) *Biochemistry* 27:1094-1104; Bonin, (1993) Ph.D. Thesis, University of Heidelberg; Gossen, et al., (1992) *Proc. Natl. Acad. Sci. USA* 89:5547-5551; Oliva, et al., (1992) *Antimicrob. Agents Chemother.* 36:913-919; Hlavka, et al., (1985) *Handbook of Experimental Pharmacology*, Vol. 78 (Springer-Verlag, Berlin); Gill, et al., (1988) *Nature* 334:721-724. Such disclosures are herein incorporated by reference. The above list of selectable marker genes is not meant to be limiting. Any selectable marker gene can be used in the present invention.

A number of promoters can be used in the practice of the invention, including the native promoter of the polynucleotide sequence of interest. The promoters can be selected based on the desired outcome. The nucleic acids can be combined with constitutive, inducible, tissue-preferred, or other promoters for expression in plants.

Such constitutive promoters include, for example, the core promoter of the Rsyn7 promoter and other constitutive promoters disclosed in WO 99/43838 and U.S. Pat. No. 6,072,050; the core CaMV 35S promoter (Odell, et al., (1985) *Nature* 313:810-812); rice actin (McElroy, et al., (1990) *Plant*

Cell 2:163-171); ubiquitin (Christensen, et al., (1989) *Plant Mol. Biol.* 12:619-632 and Christensen, et al., (1992) *Plant Mol. Biol.* 18:675-689); pEMU (Last, et al., (1991) *Theor. Appl. Genet.* 81:581-588); MAS (Velten, et al., (1984) *EMBO J.* 3:2723-2730); ALS promoter (U.S. Pat. No. 5,659,026) and the like. Other constitutive promoters include, for example, U.S. Pat. Nos. 5,608,149; 5,608,144; 5,604,121; 5,569,597; 5,466,785; 5,399,680; 5,268,463; 5,608,142 and 6,177,611.

Tissue-preferred promoters can be utilized to target enhanced IPT expression within a particular plant tissue. Tissue-preferred promoters include Yamamoto, et al., (1997) *Plant J.* 12(2):255-265; Kawamata, et al., (1997) *Plant Cell Physiol.* 38(7):792-803; Hansen, et al., (1997) *Mol. Gen. Genet.* 254(3):337-343; Russell, et al., (1997) *Transgenic Res.* 6(2):157-168; Rinehart, et al., (1996) *Plant Physiol.* 112(3):1331-1341; Van Camp, et al., (1996) *Plant Physiol.* 112(2):525-535; Canevascini, et al., (1996) *Plant Physiol.* 112(2):513-524; Yamamoto, et al., (1994) *Plant Cell Physiol.* 35(5):773-778; Lam, (1994) *Results Probl. Cell Differ.* 20:181-196; Orozco, et al., (1993) *Plant Mol. Biol.* 23(6): 1129-1138; Matsuoka, et al., (1993) *Proc Natl. Acad. Sci. USA* 90(20):9586-9590 and Guevara-Garcia, et al., (1993) *Plant J.* 4(3):495-505. Such promoters can be modified, if necessary, for weak expression. See, also, US Patent Application Publication Number 2003/0074698, herein incorporated by reference.

Leaf-preferred promoters are known in the art. See, for example, Yamamoto, et al., (1997) *Plant J.* 12(2):255-265; Kwon, et al., (1994) *Plant Physiol.* 105:357-67; Yamamoto, et al., (1994) *Plant Cell Physiol.* 35(5):773-778; Gotor, et al., (1993) *Plant J.* 3:509-18; Orozco, et al., (1993) *Plant Mol. Biol.* 23(6):1129-1138; Baszczynski, et al., (1988) *Nucl. Acid Res.* 16:4732; Mitra, et al., (1994) *Plant Molecular Biology* 26:35-93; Kayaya, et al., (1995) *Molecular and General Genetics* 248:668-674 and Matsuoka, et al., (1993) *Proc. Natl. Acad. Sci. USA* 90(20):9586-9590. Senecence regulated promoters are also of use, such as, SAM22 (Crowell, et al., (1992) *Plant Mol. Biol.* 18:459-466). See, also, U.S. Pat. No. 5,589,052 herein incorporated by reference.

Root-preferred promoters are known and can be selected from the many available from the literature or isolated de novo from various compatible species. See, for example, Hire, et al., (1992) *Plant Mol. Biol.* 20(2):207-218 (soybean root-specific glutamine synthetase gene); Keller and Baumgartner, (1991) *Plant Cell* 3(10):1051-1061 (root-specific control element in the GRP 1.8 gene of French bean); Sanger, et al., (1990) *Plant Mol. Biol.* 14(3):433-443 (root-specific promoter of the mannopine synthase (MAS) gene of *Agrobacterium tumefaciens*); and Miao, et al., (1991) *Plant Cell* 3(1):11-22 (full-length cDNA clone encoding cytosolic glutamine synthetase (GS), which is expressed in roots and root nodules of soybean). See also, Bogusz, et al., (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi, (1991) describe their analysis of the promoters of the highly expressed rolC and rolD root-inducing genes of *Agrobacterium rhizogenes* (see, *Plant Science* (Limerick) 79(1):69-76). They concluded that enhancer and tissue-preferred DNA determinants are dissociated in those promoters. Teeri, et al., (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see, *EMBO J.* 8(2):343-350). The TR1' gene, fused to nptII (neomycin phosphotransferase 11) showed similar characteristics. Additional root-preferred promoters include the VfENOD-GRP3 gene promoter (Kuster, et al., (1995) *Plant Mol. Biol.* 29(4):759-772); rolB promoter (Capana, et al., (1994) *Plant Mol. Biol.* 25(4):681-691; and the CRWAQ81 root-preferred promoter with the ADH first intron (US Patent Application Publication Number 2005/0097633). See also, U.S. Pat. Nos. 5,837,876; 5,750,386; 5,633,363; 5,459,252; 5,401,836; 5,110,732 and 5,023,179.

"Seed-preferred" promoters refers to those promoters active during seed development and may include expression in seed initials or related maternal tissue. Such seed-preferred promoters include, but are not limited to, Cim1 (cytokinin-induced message); cZ19B1 (maize 19 kDa zein); milps (myo-inositol-1-phosphate synthase) (see, WO 00/11177 and U.S. Pat. No. 6,225,529; herein incorporated by reference). Gamma-zein is an endosperm-specific promoter. Globulin-1 (Glob-1) is a representative embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, gamma-zein, waxy, shrunken 1, shrunken 2, globulin 1, etc. See also, WO 00/12733, where seed-preferred promoters from end1 and end2 genes are disclosed; herein incorporated by reference. Additional embryo specific promoters are disclosed in Sato, et al., (1996) *Proc. Natl. Acad. Sci.* 93:8117-8122; Nakase, et al., (1997) *Plant J* 12:235-46; and Postma-Haarsma, et al., (1999) *Plant Mol. Biol.* 39:257-71. Additional endosperm specific promoters are disclosed in Albani, et al., (1984) *EMBO* 3:1405-15; Albani, et al., (1999) *Theor. Appl. Gen.* 98:1253-62; Albani, et al., (1993) *Plant J.* 4:343-55; Mena, et al., (1998) *The Plant Journal* 116:53-62 and Wu, et al., (1998) *Plant Cell Physiology* 39:885-889.

Also of interest are promoters active in meristem regions, such as developing inflorescence tissues, and promoters which drive expression at or about the time of anthesis or early kernel development. This may include, for example, the maize Zag promoters, including Zag1 and Zag2 (see, Schmidt, et al., (1993) *The Plant Cell* 5:729-37; GenBank X80206; Theissen, et al., (1995) *Gene* 156:155-166 and U.S. patent application Ser. No. 10/817,483); maize Zap promoter (also known as ZmMADS; U.S. patent application Ser. No. 10/387,937; WO 03/078590); maize ckx1-2 promoter (US Patent Application Publication Number 2002/0152500 A1; WO 02/0078438); maize eep1 promoter (U.S. patent application Ser. No. 10/817,483); maize end2 promoter (U.S. Pat. No. 6,528,704 and U.S. patent application Ser. No. 10/310, 191); maize lec1 promoter (U.S. patent application Ser. No. 09/718,754); maize F3.7 promoter (Baszczynski, et al., (1997) *Maydica* 42:189-201); maize tb1 promoter (Hubbarda, et al., (2002) *Genetics* 162:1927-1935 and Wang, et al., (1999) *Nature* 398:236-239); maize eep2 promoter (U.S. patent application Ser. No. 10/817,483); maize thioredoxinH promoter (U.S. Provisional Patent Application Ser. No. 60/514,123); maize Zm40 promoter (U.S. Pat. No. 6,403,862 and WO 01/2178); maize mLIP15 promoter (U.S. Pat. No. 6,479,734); maize ESR promoter (U.S. patent application Ser. No. 10/786,679); maize PCNA2 promoter (U.S. patent application Ser. No. 10/388,359); maize cytokinin oxidase promoters (U.S. patent application Ser. No. 11/094,917); promoters disclosed in Weigal, et al., (1992) *Cell* 69:843-859; Accession Number AJ131822; Accession Number Z71981; Accession Number AF049870 and shoot-preferred promoters disclosed in McAvoy, et al., (2003) *Acta Hort.* (*ISHS*) 625:379-385. Other dividing cell or meristematic tissue-preferred promoters that may be of interest have been disclosed in Ito, et al., (1994) *Plant Mol. Biol.* 24:863-878; Regad, et al., (1995) *Mo. Gen. Genet.* 248:703-711; Shaul, et al., (1996) *Proc. Natl. Acad. Sci.* 93:4868-4872; Ito, et al., (1997) *Plant J.* 11:983-992 and Trehin, et al., (1997) *Plant Mol. Biol.* 35:667-672, all of which are hereby incorporated by reference herein.

Inflorescence-preferred promoters include the promoter of chalcone synthase (Van der Meer, et al., (1990) *Plant Mol. Biol.* 15:95-109), LAT52 (Twell, et al., (1989) *Mol. Gen. Genet.* 217:240-245), pollen specific genes (Albani, et al., (1990) *Plant Mol. Biol.* 15:605, Zm13 (Buerrero, et al., (1993) *Mol. Gen. Genet.* 224:161-168), maize pollen-specific gene (Hamilton, et al., (1992) *Plant Mol. Biol.* 18:211-218), sunflower pollen expressed gene (Baltz, et al., (1992) *The Plant Journal* 2:713-721) and *B. napus* pollen specific genes (Arnoldo, et al., (1992) *J. Cell. Biochem*, Abstract Number Y101204).

Stress-inducible promoters include salt/water stress-inducible promoters such as P5CS (Zang, et al., (1997) *Plant Sciences* 129:81-89); cold-inducible promoters, such as, cor15a (Hajela, et al., (1990) *Plant Physiol.* 93:1246-1252), cor15b (Wlihelm, et al., (1993) *Plant Mol Biol* 23:1073-1077), wsc120 (Ouellet, et al., (1998) *FEBS Lett.* 423-324-328), ci7 (Kirch, et al., (1997) *Plant Mol. Biol.* 33:897-909), ci21A (Schneider, et al., (1997) *Plant Physiol.* 113:335-45); drought-inducible promoters, such as, Trg-31 (Chaudhary, et al., (1996) *Plant Mol. Biol.* 30:1247-57); osmotic inducible promoters, such as, Rab17 (Vilardell, et al., (1991) *Plant Mol. Biol.* 17:985-93) and osmotin (Raghothama, et al., (1993) *Plant Mol Biol* 23:1117-28) and heat inducible promoters, such as, heat shock proteins (Barros, et al. (1992) *Plant Mol.* 19:665-75; Marrs, et al., (1993) *Dev. Genet.* 14:27-41), and smHSP (Waters, et al., (1996) *J. Experimental Botany* 47:325-338). Other stress-inducible promoters include rip2 (U.S. Pat. No. 5,332,808 and US Patent Application Publication Number 2003/0217393) and rd29a (Yamaguchi-Shinozaki, et al., (1993) *Mol. Gen. Genetics* 236:331-340).

Stress-insensitive promoters can also be used in the methods of the invention. This class of promoters, as well as representative examples, are further described elsewhere herein.

Nitrogen-responsive promoters can also be used in the methods of the invention. Such promoters include, but are not limited to, the 22 kDa Zein promoter (Spena, et al., (1982) *EMBO J.* 1:1589-1594 and Muller, et al., (1995) *J. Plant Physiol* 145:606-613); the 19 kDa zein promoter (Pedersen, et al., (1982) *Cell* 29:1019-1025); the 14 kDa zein promoter (Pedersen, et al., (1986) *J. Biol. Chem.* 261:6279-6284), the b-32 promoter (Lohmer, et al., (1991) *EMBO J.* 10:617-624) and the nitrite reductase (NiR) promoter (Rastogi, et al., (1997) *Plant Mol. Biol.* 34(3):465-76 and Sander, et al., (1995) *Plant Mol. Biol.* 27(1):165-77). For a review of consensus sequences found in nitrogen-induced promoters, see for example, Muller, et al., (1997) *The Plant Journal* 12:281-291.

Chemically-regulated promoters can be used to modulate the expression of a gene in a plant through the application of an exogenous chemical regulator. Depending upon the objective, the promoter may be a chemically-inducible promoter, where application of the chemical induces gene expression, or a chemical-repressible promoter, where application of the chemical represses gene expression. Chemically-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena, et al., (1991) *Proc. Natl. Acad. Sci. USA* 88:10421-10425 and McNellis, et al., (1998) *Plant J.* 14(2):247-257) and tetracycline-inducible and tetracycline-repressible promoters (see, for example, Gatz, et al., (1991) *Mol. Gen. Genet.* 227:229-237 and U.S. Pat. Nos. 5,814,618 and 5,789,156), herein incorporated by reference.

A promoter induced by cytokinin, such as the ZmCkx1-2 promoter (U.S. Pat. No. 6,921,815 and pending U.S. patent application Ser. No. 11/074,144), may also be used in the methods and compositions of the invention. Such a construct would amplify biosynthesis of cytokinin occurring in developmental stages and/or tissues of interest. Other cytokinin-inducible promoters are described in pending U.S. patent application Ser. Nos. 11/094,917 and 11/273,537, all hereby incorporated by reference.

Additional inducible promoters include heat shock promoters, such as Gmhsp17.5-E (soybean) (Czarnecka, et al., (1989) *Mol Cell Biol.* 9(8):3457-3463); APX1 gene promoter (Arabidopsis) (Storozhenko, et al., (1998) *Plant Physiol.* 118 (3):1005-1014): Ha hspI7.7 G4 (*Helianthus annuus*) (Almoguera, et al., (2002) *Plant Physiol.* 129(1):333-341 and Maize Hsp70 (Rochester, et al., (1986) *EMBO J.* 5: 451-8.

The methods of the invention involve introducing a polypeptide or polynucleotide into a plant. "Introducing" is intended to mean presenting to the plant the polynucleotide or polypeptide in such a manner that the sequence gains access to the interior of a cell of the plant. The methods of the invention do not depend on a particular method for introducing a sequence into a plant, only that the polynucleotide or polypeptides gains access to the interior of at least one cell of the plant. Methods for introducing polynucleotides or polypeptides into plants are known in the art and include, but are not limited to, stable transformation methods, transient transformation methods and virus-mediated methods.

"Stable transformation" is intended to mean that the nucleotide construct of interest introduced into a plant integrates into the genome of the plant and is capable of being inherited by the progeny thereof. "Transient transformation" is intended to mean that a sequence is introduced into the plant and is only temporarily expressed or present in the plant.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway, et al., (1986) *Biotechniques* 4:320-334), electroporation (Riggs, et al., (1986) *Proc. Natl. Acad. Sci. USA* 83:5602-5606), *Agrobacterium*-mediated transformation (U.S. Pat. No. 5,563,055 and U.S. Pat. No. 5,981,840), direct gene transfer (Paszkowski, et al., (1984) *EMBO J.* 3:2717-2722) and ballistic particle acceleration (see, for example, U.S. Pat. No. 4,945,050; U.S. Pat. No. 5,879,918; U.S. Pat. Nos. 5,886,244 and 5,932,782; Tomes, et al., (1995) in *Plant Cell, Tissue, and Organ Culture: Fundamental Methods*, ed. Gamborg and Phillips, (Springer-Verlag, Berlin); McCabe, et al., (1988) Biotechnology 6:923-926) and Lec1 transformation (WO 00/28058). Also see, Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); McCabe, et al., (1988) *Bio/Technology* 6:923-926 (soybean); Finer and McMullen, (1991) *In Vitro Cell Dev. Biol.* 27P:175-182 (soybean); Singh, et al., (1998) *Theor. Appl. Genet.* 96:319-324 (soybean); Datta, et al., (1990) *Biotechnology* 8:736-740 (rice); Hoque, et al., (2005) *Plant Cell Tissue & Organ Culture* 82(1):45-55 (rice); Sreekala, et al., (2005) *Plant Cell Reports* 24(2):86-94 (rice); Klein, et al., (1988) *Proc. Natl. Acad. Sci. USA* 85:4305-4309 (maize); Klein, et al., (1988) *Biotechnology* 6:559-563 (maize); U.S. Pat. Nos. 5,240,855; 5,322,783 and 5,324,646; Klein, et al., (1988) *Plant Physiol.* 91:440-444 (maize); Fromm, et al., (1990) *Biotechnology* 8:833-839 (maize); Hooykaas-Van Slogteren, et al., (1984) *Nature* (London) 311:763-764; U.S. Pat. No. 5,736,369 (cereals); Bytebier, et al., (1987) *Proc. Natl. Acad. Sci. USA* 84:5345-5349 (Liliaceae); De Wet, et al., (1985) in *The Experimental Manipulation of Ovule Tissues*, ed. Chapman, et al., (Longman, New York), pp. 197-209 (pollen); Kaeppler, et al., (1990) *Plant Cell Reports* 9:415-418 and Kaeppler, et al., (1992) *Theor. Appl. Genet.* 84:560-566 (whisker-mediated transformation); D'Halluin, et al., (1992) *Plant Cell* 4:1495-1505 (electroporation); Li, et al., (1993) *Plant Cell Reports* 12:250-255 and Christou and Ford, (1995) *Annals of Botany* 75:407-413 (rice); Osjoda, et al., (1996) *Nature Biotechnology* 14:745-750 (maize via *Agrobacterium tumefaciens*); all of which are herein incorporated by reference.

In specific embodiments, the IPT sequences of the invention can be provided to a plant using a variety of transient transformation methods. Such transient transformation methods include, but are not limited to, the introduction of the IPT protein or variants and fragments thereof directly into the plant or the introduction of an IPT transcript into the plant. Such methods include, for example, microinjection or particle bombardment. See, for example, Crossway, et al., (1986) *Mol. Gen. Genet.* 202:179-185; Nomura, et al., (1986) *Plant Sci.* 44:53-58; Hepler, et al., (1994) *Proc. Natl. Acad. Sci.* 91:2176-2180 and Hush, et al., (1994) *The Journal of Cell Science* 107:775-784, all of which are herein incorporated by reference. Alternatively, the IPT polynucleotide can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which it is released to become integrated into the genome is greatly reduced. Such methods include the use of particles coated with polyethyenlimine (PEI; Sigma #P3143).

In other embodiments, the polynucleotide of the invention may be introduced into plants by contacting plants with a virus or viral nucleic acids. Generally, such methods involve incorporating a nucleotide construct of the invention within a viral DNA or RNA molecule. It is recognized that an IPT polynucleotide of the invention may be initially synthesized as part of a viral polyprotein, which later may be processed by proteolysis in vivo or in vitro to produce the desired recombinant protein. Further, it is recognized that promoters useful for the invention also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931 and Porta, et al., (1996) *Molecular Biotechnology* 5:209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, and U.S. Pat. Nos. 6,187,994; 6,552,248; 6,624,297; 6,331,661; 6,262,341; 6,541,231; 6,664,108; 6,300,545; 6,528,700 and 6,911,575, all of which are herein incorporated by reference. Briefly, the polynucleotide of the invention can be contained in a transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick, et al., (1986) *Plant Cell Reports* 5:81-84. These plants may then be grown, and pollinated with either the same transformed strain or different strains, and the resulting progeny having expression of the desired phenotypic characteristic identified. Two or more generations may be grown to ensure that expression of the desired phenotypic characteristic is stably maintained and inherited and then seeds harvested to ensure that expression of the desired phenotypic characteristic has been achieved. In this manner, the present invention provides transformed seed (also referred to as "transgenic seed") having a polynucleotide of the invention, for example, an expression cassette of the invention, stably incorporated into their genome.

Pedigree breeding starts with the crossing of two genotypes, such as an elite line of interest and one other inbred line having one or more desirable characteristics (i.e., having stably incorporated a polynucleotide of the invention, having a modulated activity and/or level of the polypeptide of the invention, etc) which complements the elite line of interest. If the two original parents do not provide all the desired characteristics, other sources can be included in the breeding population. In the pedigree method, superior plants are selfed and selected in successive filial generations. In the succeeding filial generations the heterozygous condition gives way to homogeneous lines as a result of self-pollination and selection. Typically in the pedigree method of breeding, five or more successive filial generations of selfing and selection are practiced: F1→F2; F2→F3; F3→F4; F4→F$_5$, etc. After a sufficient amount of inbreeding, successive filial generations will serve to increase seed of the developed inbred. In specific embodiments, the inbred line comprises homozygous alleles at about 95% or more of its loci.

In addition to being used to create a backcross conversion, backcrossing can also be used in combination with pedigree breeding to modify an elite line of interest and a hybrid that is made using the modified elite line. Backcrossing can be used to transfer one or more specifically desirable traits from one line, the donor parent, to an inbred called the recurrent parent, which has overall good agronomic characteristics yet lacks that desirable trait or traits. However, the same procedure can be used to move the progeny toward the genotype of the recurrent parent but at the same time retain many components of the non-recurrent parent by stopping the backcrossing at an early stage and proceeding with selfing and selection. For example, an F1, such as a commercial hybrid, is created. This commercial hybrid may be backcrossed to one of its parent lines to create a BC1 or BC2. Progeny are selfed and selected so that the newly developed inbred has many of the attributes of the recurrent parent and yet several of the desired attributes of the non-recurrent parent. This approach leverages the value and strengths of the recurrent parent for use in new hybrids and breeding.

Therefore, an embodiment of this invention is a method of making a backcross conversion of a maize inbred line of interest, comprising the steps of crossing a plant of a maize inbred line of interest with a donor plant comprising a mutant gene or transgene conferring a desired trait (i.e., a modulation in the level of cytokinin (an increase or a decrease) or any plant phenotype resulting from the modulated cytokinin level (such plant phenotypes are discussed elsewhere herein)), selecting an F1 progeny plant comprising the mutant gene or transgene conferring the desired trait, and backcrossing the selected F1 progeny plant to a plant of the maize inbred line of interest. This method may further comprise the step of obtaining a molecular marker profile of the maize inbred line of interest and using the molecular marker profile to select for a progeny plant with the desired trait and the molecular marker profile of the inbred line of interest. In the same manner, this method may be used to produce F1 hybrid seed by adding a final step of crossing the desired trait conversion of the maize inbred line of interest with a different maize plant to make F1 hybrid maize seed comprising a mutant gene or transgene conferring the desired trait.

Recurrent selection is a method used in a plant breeding program to improve a population of plants. The method entails individual plants cross pollinating with each other to form progeny. The progeny are grown and the superior progeny selected by any number of selection methods, which include individual plant, half-sib progeny, full-sib progeny, selfed progeny and topcrossing. The selected progeny are cross-pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain inbred lines to be used in hybrids or used as parents for a synthetic cultivar. A synthetic cultivar is the resultant progeny formed by the intercrossing of several selected inbreds.

Mass selection is a useful technique when used in conjunction with molecular marker enhanced selection. In mass selection seeds from individuals are selected based on phenotype and/or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Instead of self pollination, directed pollination could be used as part of the breeding program.

Mutation breeding is one of many methods that could be used to introduce new traits into an elite line. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation such as X-rays, Gamma rays (e.g., cobalt 60 or cesium 137), neutrons, (product of nuclear fission by uranium 235 in an atomic reactor), Beta radiation (emitted from radioisotopes such as phosphorus 32 or carbon 14) or ultraviolet radiation (preferably from 2500 to 2900 nm) or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid or acridines. Once a desired trait is observed through mutagenesis the trait may then be incorporated into existing germplasm by traditional breeding techniques, such as backcrossing. Details of mutation breeding can be found in "Principals of Cultivar Development," Fehr, 1993 Macmillan Publishing Company, the disclosure of which is incorporated herein by reference. In addition, mutations created in other lines may be used to produce a backcross conversion of elite lines that comprises such mutations.

The present invention may be used for transformation of any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*) and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*) and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*) and cedars such as Western red cedar (*Thuja plicata*) and Alaska yellow-cedar (*Chamaecyparis nootkatensis*). In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean plants are optimal, and in yet other embodiments corn plants are optimal.

Other plants of interest include grain plants that provide seeds of interest, oil-seed plants and leguminous plants. Seeds of interest include grain seeds, such as maize, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

Typically, an intermediate host cell will be used in the practice of this invention to increase the copy number of the cloning vector. With an increased copy number, the vector containing the nucleic acid of interest can be isolated in significant quantities for introduction into the desired plant cells. In one embodiment, plant promoters that do not cause expression of the polypeptide in bacteria are employed.

Prokaryotes most frequently are represented by various strains of *E. coli*; however, other microbial strains may also be used. Commonly used prokaryotic control sequences which are defined herein to include promoters for transcription initiation, optionally with an operator, along with ribosome binding sequences, include such commonly used promoters as the beta lactamase (penicillinase) and lactose (lac) promoter systems (Chang, et al., (1977) *Nature* 198:1056), the tryptophan (trp) promoter system (Goeddel, et al., (1980) *Nucleic Acids Res.* 8:4057) and the lambda derived P L promoter and N-gene ribosome binding site (Shimatake, et al., (1981) *Nature* 292:128). The inclusion of selection markers in DNA vectors transfected in *E. coli*. is also useful. Examples of such markers include genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus* sp. and *Salmonella* (Palva, et al., (1983) *Gene* 22:229-235); Mosbach, et al., (1983) *Nature* 302:543-545).

A variety of eukaryotic expression systems such as yeast, insect cell lines, plant and mammalian cells, are known to those of skill in the art. As explained briefly below, a polynucleotide of the present invention can be expressed in these eukaryotic systems. In some embodiments, transformed/transfected plant cells, as discussed infra, are employed as expression systems for production of the proteins of the instant invention.

Synthesis of heterologous polynucleotides in yeast is well known (Sherman, et al., (1982) *Methods in Yeast Genetics*, Cold Spring Harbor Laboratory). Two widely utilized yeasts for production of eukaryotic proteins are *Saccharomyces cerevisiae* and *Pichia pastoris*. Vectors, strains and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired. A protein of the present invention, once expressed, can be isolated from yeast by lysing the cells and applying standard protein isolation techniques to the lists. The monitoring of the purification process can be accomplished by using Western blot techniques or radioimmunoassay or other standard immunoassay techniques.

The sequences of the present invention can also be ligated to various expression vectors for use in transfecting cell cultures of, for instance, mammalian, insect or plant origin. Illustrative cell cultures useful for the production of the peptides are mammalian cells. A number of suitable host cell lines capable of expressing intact proteins have been developed in the art, and include the HEK293, BHK21 and CHO cell lines. Expression vectors for these cells can include expression control sequences, such as an origin of replication, a promoter (e.g., the CMV promoter, a HSV tk promoter or pgk (phosphoglycerate kinase) promoter), an enhancer (Queen, et al., (1986) *Immunol. Rev.* 89:49) and necessary processing information sites, such as ribosome binding sites, RNA splice sites, polyadenylation sites (e.g., an SV40 large T Ag poly A addition site) and transcriptional terminator sequences. Other animal cells useful for production of proteins of the present invention are available, for instance, from the American Type Culture Collection.

Appropriate vectors for expressing proteins of the present invention in insect cells are usually derived from the SF9 baculovirus. Suitable insect cell lines include mosquito larvae, silkworm, armyworm, moth and *Drosophila* cell lines such as a Schneider cell line (see, Schneider (1987) *J. Embryol. Exp. Morphol.* 27:353-365).

As with yeast, when higher animal or plant host cells are employed, polyadenylation or transcription terminator sequences are typically incorporated into the vector. An example of a terminator sequence is the polyadenylation sequence from the bovine growth hormone gene. Sequences for accurate splicing of the transcript may also be included. An example of a splicing sequence is the VP1 intron from SV40 (Sprague, et al., (1983) *J. Virol.* 45:773-781). Additionally, gene sequences to control replication in the host cell may be incorporated into the vector such as those found in bovine papilloma virus type-vectors (Saveria-Campo (1985) *DNA Cloning Vol. II a Practical Approach*, Glover, Ed., IRL Press, Arlington, Va., pp. 213-238).

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextrin, electroporation, biolistics and micro-injection of the DNA directly into the cells. The transfected cells are cultured by means well known in the art (Kuchler, (1997) *Biochemical Methods in Cell Culture and Virology*, Dowden, Hutchinson and Ross, Inc.).

II. Modulating the Concentration and/or Activity of an Isopentenyl Transferase Polypeptide A method for modulating the concentration and/or activity of the polypeptide of the present invention in a plant is provided. In general, concentration and/or activity of the IPT polypeptide is increased or reduced by at least 1%, 5%, 10%, 20%, 30%, 40%, 50%, 60%, 70%, 80% or 90% or more, relative to a native control plant, plant part or cell which does not comprise the introduced sequence. Modulation of the concentration and/or activity may occur at one or more stages of development. In specific embodiments, the polypeptides of the present invention are modulated in monocots, such as maize.

The expression level of the IPT polypeptide may be measured directly, for example, by assaying for the level of the IPT polypeptide in the plant, or indirectly, for example, by measuring the cytokinin synthesis activity in the plant. Methods for assaying for cytokinin synthesis activity are described elsewhere herein.

In specific embodiments, the polypeptide or the polynucleotide of the invention is introduced into the plant cell. Subsequently, a plant cell having the introduced sequence of the invention is selected using methods known to those of skill in the art such as, but not limited to, Southern blot analysis, DNA sequencing, PCR analysis or phenotypic analysis. A plant or plant part altered or modified by the foregoing embodiments is grown under plant forming conditions for a time sufficient to modulate the concentration and/or activity of polypeptides of the present invention in the plant. Plant forming conditions are well known in the art and discussed briefly elsewhere herein.

It is also recognized that the level and/or activity of the polypeptide may be modulated by employing a polynucleotide that is not capable of directing, in a transformed plant, the expression of a protein or RNA. For example, the polynucleotides of the invention may be used to design polynucleotide constructs that can be employed in methods for altering or mutating a genomic nucleotide sequence in an organism. Such polynucleotide constructs include, but are not limited to, RNA:DNA vectors, RNA:DNA mutational vectors, RNA:DNA repair vectors, mixed-duplex oligonucleotides, self-complementary RNA:DNA oligonucleotides, and recombinogenic oligonucleobases. Such nucleotide constructs and methods of use are known in the art. See, U.S. Pat. Nos. 5,565,350; 5,731,181; 5,756,325; 5,760,012; 5,795,972 and 5,871,984; all of which are herein incorporated by reference. See also, WO 98/49350, WO 99/07865, WO 99/25821 and Beetham, et al., (1999) Proc. Natl. Acad. Sci. USA 96:8774-8778; herein incorporated by reference.

It is therefore recognized that methods of the present invention do not depend on the incorporation of the entire polynucleotide into the genome, only that the plant or cell thereof is altered as a result of the introduction of the polynucleotide into a cell. In one embodiment of the invention, the genome may be altered following the introduction of a polynucleotide into a cell. For example, the polynucleotide, or any part thereof, may incorporate into the genome of the plant. Alterations to the genome include, but are not limited to, additions, deletions, and substitutions of nucleotides into the genome. While the methods of the present invention do not depend on additions, deletions and substitutions of any particular number of nucleotides, it is recognized that such additions, deletions or substitutions comprise at least one nucleotide.

It is further recognized that modulating the level and/or activity of the IPT sequence can be performed to elicit the effects of the sequence only during certain developmental stages and to switch the effect off in other stages where expression is no longer desirable. Control of the IPT expression can be obtained via the use of inducible or tissue-preferred promoters. Alternatively, the gene could be inverted or deleted using site-specific recombinases, transposons or recombination systems, which would also turn on or off expression of the IPT sequence.

A "subject plant or plant cell" is one in which genetic alteration, such as transformation, has been effected as to a gene of interest, or is a plant or plant cell which is descended from a plant or cell so altered and which comprises the alteration. A "control" or "control plant" or "control plant cell" provides a reference point for measuring changes in phenotype of the subject plant or plant cell.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e. with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest or (e) the subject plant or plant cell itself, under conditions in which the gene of interest is not expressed.

In the present case, for example, changes in cytokinin levels, including changes in absolute amounts of cytokinin, cytokinin ratios, cytokinin activity, or cytokinin distribution or changes in plant or plant cell phenotype, such as flowering time, seed set, branching, senescence, stress tolerance or root mass, could be measured by comparing a subject plant or plant cell to a control plant or plant cell.

In certain embodiments the nucleic acid constructs of the present invention can be used in combination ("stacked") with other polynucleotide sequences of interest in order to create plants with a desired phenotype. The polynucleotides of the present invention may be stacked with any gene or combination of genes, and the combinations generated can include multiple copies of any one or more of the polynucleotides of interest. The desired combination may affect one or more traits; that is, certain combinations may be created for modulation of gene expression affecting cytokinin activity. For example, up-regulation of cytokinin synthesis may be combined with down-regulation of cytokinin degradation. Other combinations may be designed to produce plants with a variety of desired traits, such as those previously described.

A. Increasing the Activity and/or Concentration of an Isopentenyl Transferase Polypeptide Methods are provided to increase the activity and/or concentration of the IPT polypeptide of the invention. An increase in the concentration and/or activity of the IPT polypeptide of the invention can be achieved by providing to the plant an IPT polypeptide. As discussed elsewhere herein, many methods are known in the art for providing a polypeptide to a plant including, but not limited to, direct introduction of the polypeptide into the plant, and introducing into the plant (transiently or stably) a polynucleotide construct encoding a polypeptide having cytokinin synthesis activity. It is also recognized that the methods of the invention may employ a polynucleotide that is not capable of directing, in the transformed plant, the expression of a protein or RNA. Thus, the level and/or activity of an IPT polypeptide may be increased by altering the gene encoding the IPT polypeptide or its promoter. See, e.g., Kmiec, U.S. Pat. No. 5,565,350; Zarling, et al., PCT/US93/03868. Therefore mutagenized plants that carry mutations in IPT genes, where the mutations increase expression of the IPT gene or increase the cytokinin synthesis activity of the encoded IPT polypeptide are provided. As described elsewhere herein, methods to assay for an increase in protein concentration or an increase in cytokinin synthesis activity are known.

B. Reducing the Activity and/or Concentration of an Isopentenyl Transferase Polypeptide Methods are provided to reduce or eliminate the activity and/or concentration of the IPT polypeptide by transforming a plant cell with an expression cassette that expresses a polynucleotide that inhibits the expression of the IPT polypeptide. The polynucleotide may inhibit the expression of an IPT polypeptide directly, by preventing translation of the IPT polypeptide messenger RNA, or indirectly, by encoding a molecule that inhibits the transcription or translation of an IPT polypeptide gene encoding an IPT polypeptide. Methods for inhibiting or eliminating the expression of a gene in a plant are well known in the art, and any such method may be used in the present invention to inhibit the expression of the IPT polypeptides.

In accordance with the present invention, the expression of an IPT polypeptide is inhibited if the level of the IPT polypeptide is statistically lower than the level of the same IPT polypeptide in a plant that has not been genetically modified or mutagenized to inhibit the expression of that IPT polypeptide. In particular embodiments of the invention, the protein level of the IPT polypeptide in a modified plant according to the invention is less than 95%, less than 90%, less than 80%, less than 70%, less than 60%, less than 50%, less than 40%, less than 30%, less than 20%, less than 10% or less than 5% of the protein level of the same IPT polypeptide in a plant that is not a mutant or that has not been genetically modified to inhibit the expression of that IPT polypeptide. The expression level of the IPT polypeptide may be measured directly, for example, by assaying for the level of the IPT polypeptide expressed in the cell or plant, or indirectly, for example, by measuring the cytokinin synthesis activity in the cell or plant. Methods for determining the cytokinin synthesis activity of the IPT polypeptide are described elsewhere herein.

In other embodiments of the invention, the activity of one or more IPT polypeptides is reduced or eliminated by transforming a plant cell with an expression cassette comprising a polynucleotide encoding a polypeptide that inhibits the activity of one or more IPT polypeptides. The cytokinin synthesis activity of an IPT polypeptide is inhibited according to the present invention if the cytokinin synthesis activity of the IPT polypeptide is statistically lower than the cytokinin synthesis activity of the same IPT polypeptide in a plant that has not been genetically modified to inhibit the cytokinin synthesis activity of that IPT polypeptide. In particular embodiments of the invention, the cytokinin synthesis activity of the IPT polypeptide in a modified plant according to the invention is less than 95%, less than 90%, less than 80%, less than 70%, less than 60%, less than 50%, less than 40%, less than 30%, less than 20%, less than 10% or less than 5% of the cytokinin synthesis activity of the same IPT polypeptide in a plant that that has not been genetically modified to inhibit the expression of that IPT polypeptide. The cytokinin synthesis activity of an IPT polypeptide is "eliminated" according to the invention when it is not detectable by the assay methods described elsewhere herein. Methods of determining the cytokinin synthesis activity of an IPT polypeptide are described elsewhere herein.

In other embodiments, the activity of an IPT polypeptide may be reduced or eliminated by disrupting the gene encoding the IPT polypeptide. The invention encompasses mutagenized plants that carry mutations in IPT genes, where the mutations reduce expression of the IPT gene or inhibit the cytokinin synthesis activity of the encoded IPT polypeptide.

Thus, many methods may be used to reduce or eliminate the activity of an IPT polypeptide. More than one method may be used to reduce the activity of a single IPT polypeptide. In addition, combinations of methods may be employed to reduce or eliminate the activity of two or more different IPT polypeptides.

Non-limiting examples of methods of reducing or eliminating the expression of an IPT polypeptide are given below.

1. Polynucleotide-Based Methods

In some embodiments of the present invention, a plant cell is transformed with an expression cassette that is capable of expressing a polynucleotide that inhibits the expression of an IPT sequence. The term "expression" as used herein refers to the biosynthesis of a gene product, including the transcription and/or translation of said gene product. For example, for the purposes of the present invention, an expression cassette capable of expressing a polynucleotide that inhibits the expression of at least one IPT sequence is an expression cassette capable of producing an RNA molecule that inhibits the transcription and/or translation of at least one IPT polypeptide. The "expression" or "production" of a protein or polypeptide from a DNA molecule refers to the transcription and translation of the coding sequence to produce the protein or polypeptide, while the "expression" or "production" of a protein or polypeptide from an RNA molecule refers to the translation of the RNA coding sequence to produce the protein or polypeptide.

Examples of polynucleotides that inhibit the expression of an IPT sequence are given below.

i. Sense Suppression/Cosuppression

In some embodiments of the invention, inhibition of the expression of an IPT polypeptide may be obtained by sense suppression or cosuppression. For cosuppression, an expression cassette is designed to express an RNA molecule corresponding to all or part of a messenger RNA encoding an IPT polypeptide in the "sense" orientation. Over expression of the RNA molecule can result in reduced expression of the native gene. Accordingly, multiple plant lines transformed with the cosuppression expression cassette are screened to identify those that show the greatest inhibition of IPT polypeptide expression.

The polynucleotide used for cosuppression may correspond to all or part of the sequence encoding the IPT polypeptide, all or part of the 5' and/or 3' untranslated region of an IPT polypeptide transcript or all or part of both the coding sequence and the untranslated regions of a transcript encoding an IPT polypeptide. In some embodiments where the polynucleotide comprises all or part of the coding region for the IPT polypeptide, the expression cassette is designed to eliminate the start codon of the polynucleotide so that no protein product will be transcribed.

Cosuppression may be used to inhibit the expression of plant genes to produce plants having undetectable protein levels for the proteins encoded by these genes. See, for example, Broin, et al., (2002) *Plant Cell* 14:1417-1432. Cosuppression may also be used to inhibit the expression of multiple proteins in the same plant. See, for example, U.S. Pat. No. 5,942,657. Methods for using cosuppression to inhibit the expression of endogenous genes in plants are described in Flavell, et al., (1994) *Proc. Natl. Acad. Sci. USA* 91:3490-3496; Jorgensen, et al., (1996) *Plant Mol. Biol.* 31:957-973; Johansen and Carrington, (2001) *Plant Physiol.* 126:930-938; Broin, et al., (2002) *Plant Cell* 14:1417-1432; Stoutjesdijk, et al., (2002) *Plant Physiol.* 129:1723-1731; Yu, et al., (2003) *Phytochemistry* 63:753-763 and U.S. Pat. Nos. 5,034,323, 5,283,184 and 5,942,657; each of which is herein incorporated by reference. The efficiency of cosuppression may be increased by including a poly-dT region in the expression cassette at a position 3' to the sense sequence and 5' of the polyadenylation signal. See, US Patent Application Publication Number 2002/0048814, herein incorporated by reference. Typically, such a nucleotide sequence has substantial sequence identity to the sequence of the transcript of the endogenous gene, optimally greater than about 65% sequence identity, more optimally greater than about 85% sequence identity, most optimally greater than about 95% sequence identity. See, U.S. Pat. Nos. 5,283,184 and 5,034, 323, herein incorporated by reference.

ii. Antisense Suppression

In some embodiments of the invention, inhibition of the expression of the IPT polypeptide may be obtained by antisense suppression. For antisense suppression, the expression cassette is designed to express an RNA molecule complementary to all or part of a messenger RNA encoding the IPT polypeptide. Over expression of the antisense RNA molecule can result in reduced expression of the native gene. Accordingly, multiple plant lines transformed with the antisense suppression expression cassette are screened to identify those that show the greatest inhibition of IPT polypeptide expression.

The polynucleotide for use in antisense suppression may correspond to all or part of the complement of the sequence encoding the IPT polypeptide, all or part of the complement of the 5' and/or 3' untranslated region of the IPT polypeptide transcript, or all or part of the complement of both the coding sequence and the untranslated regions of a transcript encoding the IPT polypeptide. In addition, the antisense polynucleotide may be fully complementary (i.e., 100% identical to the complement of the target sequence) or partially complementary (i.e., less than 100% identical to the complement of the target sequence) to the target sequence. Antisense suppression may be used to inhibit the expression of multiple proteins in the same plant. See, for example, U.S. Pat. No. 5,942,657. Furthermore, portions of the antisense nucleotides may be used to disrupt the expression of the target gene. Generally, sequences of at least 50 nucleotides, 100 nucleotides, 200 nucleotides, 300, 400, 450, 500, 550 or greater may be used. Methods for using antisense suppression to inhibit the expression of endogenous genes in plants are described, for example, in Liu, et al., (2002) *Plant Physiol.* 129:1732-1743 and U.S. Pat. Nos. 5,759,829 and 5,942,657, each of which is herein incorporated by reference. Efficiency of antisense suppression may be increased by including a poly-dT region in the expression cassette at a position 3' to the antisense sequence and 5' of the polyadenylation signal. See, US Patent Application Publication Number 2002/0048814, herein incorporated by reference.

iii. Double-Stranded RNA Interference

In some embodiments of the invention, inhibition of the expression of an IPT polypeptide may be obtained by double-stranded RNA (dsRNA) interference. For dsRNA interference, a sense RNA molecule like that described above for cosuppression and an antisense RNA molecule that is fully or partially complementary to the sense RNA molecule are expressed in the same cell, resulting in inhibition of the expression of the corresponding endogenous messenger RNA.

Expression of the sense and antisense molecules can be accomplished by designing the expression cassette to comprise both a sense sequence and an antisense sequence. Alternatively, separate expression cassettes may be used for the sense and antisense sequences. Multiple plant lines transformed with the dsRNA interference expression cassette or expression cassettes are then screened to identify plant lines that show the greatest inhibition of IPT polypeptide expression. Methods for using dsRNA interference to inhibit the expression of endogenous plant genes are described in Waterhouse, et al., (1998) *Proc. Natl. Acad. Sci. USA* 95:13959-13964, Liu, et al., (2002) *Plant Physiol.* 129:1732-1743 and WO 99/49029, WO 99/53050, WO 99/61631 and WO 00/49035, each of which is herein incorporated by reference.

iv. Hairpin RNA Interference and Intron-Containing Hairpin RNA Interference

In some embodiments of the invention, inhibition of the expression of one or more IPT polypeptides may be obtained by hairpin RNA (hpRNA) interference or intron-containing hairpin RNA (ihpRNA) interference. These methods are highly efficient at inhibiting the expression of endogenous genes. See, Waterhouse and Helliwell, (2003) *Nat. Rev. Genet.* 4:29-38 and the references cited therein.

For hpRNA interference, the expression cassette is designed to express an RNA molecule that hybridizes with itself to form a hairpin structure that comprises a single-stranded loop region and a base-paired stem. The base-paired stem region comprises a sense sequence corresponding to all or part of the endogenous messenger RNA encoding the gene whose expression is to be inhibited, and an antisense sequence that is fully or partially complementary to the sense sequence. Thus, the base-paired stem region of the molecule generally determines the specificity of the RNA interference. hpRNA molecules are highly efficient at inhibiting the expression of endogenous genes, and the RNA interference they induce is inherited by subsequent generations of plants. See, for example, Chuang and Meyerowitz, (2000) *Proc. Natl. Acad. Sci. USA* 97:4985-4990; Stoutjesdijk, et al., (2002) *Plant Physiol.* 129:1723-1731 and Waterhouse and Helliwell, (2003) *Nat. Rev. Genet.* 4:29-38. Methods for using hpRNA interference to inhibit or silence the expression of genes are described, for example, in Chuang and Meyerowitz, (2000) *Proc. Natl. Acad. Sci. USA* 97:4985-4990; Stoutjesdijk, et al., (2002) *Plant Physiol.* 129:1723-1731; Waterhouse and Helliwell, (2003) *Nat. Rev. Genet.* 4:29-38; Pandolfini, et al., *BMC Biotechnology* 3:7 and US Patent Application Publication Number 2003/0175965; each of which is herein incorporated by reference. A transient assay for the efficiency of hpRNA constructs to silence gene expression in vivo has been described by Panstruga, et al., (2003) *Mol. Biol. Rep.* 30:135-140, herein incorporated by reference.

Alternatively, the base-paired stem region may correspond to a portion of a promoter sequence controlling expression of the gene to be inhibited. Transcriptional gene silencing (TGS) may be accomplished through use of hpRNA constructs wherein the inverted repeat of the hairpin shares sequence identity with the promoter region driving expression of a gene to be silenced. See, for example, U.S. patent application Ser. No. 11/014,071, filed 16 Dec. 2004. Processing of the hpRNA into short RNAs which can interact with the homologous promoter region may trigger degradation or methylation to result in silencing (Aufsatz, et al., (2002) *PNAS* 99 (Suppl. 4):16499-16506; Mette, et al., (2000) *EMBO J.* 19(19):5194-5201).

For ihpRNA, the interfering molecules have the same general structure as for hpRNA, but the RNA molecule additionally comprises an intron that is capable of being spliced in the cell in which the ihpRNA is expressed. The use of an intron minimizes the size of the loop in the hairpin RNA molecule following splicing, and this increases the efficiency of interference. See, for example, Smith, et al., (2000) *Nature* 407: 319-320. In fact, Smith, et al., show 100% suppression of endogenous gene expression using ihpRNA-mediated interference. Methods for using ihpRNA interference to inhibit the expression of endogenous plant genes are described, for example, in Smith, et al., (2000) *Nature* 407:319-320; Wesley, et al., (2001) *Plant J.* 27:581-590; Wang and Waterhouse, (2001) *Curr. Opin. Plant Biol.* 5:146-150; Waterhouse and Helliwell, (2003) *Nat. Rev. Genet.* 4:29-38; Helliwell and Waterhouse, (2003) *Methods* 30:289-295 and US Patent Application Publication Number 2003/0180945, each of which is herein incorporated by reference.

The expression cassette for hpRNA interference may also be designed such that the sense sequence and the antisense sequence do not correspond to an endogenous RNA. In this embodiment, the sense and antisense sequence flank a loop sequence that comprises a nucleotide sequence corresponding to all or part of the endogenous messenger RNA of the target gene. Thus, it is the loop region that determines the specificity of the RNA interference. See, for example, WO 02/00904, herein incorporated by reference.

v. Amplicon-Mediated Interference

Amplicon expression cassettes comprise a plant virus-derived sequence that contains all or part of the target gene but generally not all of the genes of the native virus. The viral sequences present in the transcription product of the expression cassette allow the transcription product to direct its own replication. The transcripts produced by the amplicon may be either sense or antisense relative to the target sequence (i.e., the messenger RNA for an IPT polypeptide). Methods of using amplicons to inhibit the expression of endogenous plant genes are described, for example, in Angell and Baulcombe, (1997) *EMBO J.* 16:3675-3684, Angell and Baulcombe, (1999) *Plant J.* 20:357-362 and U.S. Pat. No. 6,646,805, each of which is herein incorporated by reference.

vi. Ribozymes

In some embodiments, the polynucleotide expressed by the expression cassette of the invention is catalytic RNA or has ribozyme activity specific for the messenger RNA of an IPT polypeptide. Thus, the polynucleotide causes the degradation of the endogenous messenger RNA, resulting in reduced expression of the IPT polypeptide. This method is described, for example, in U.S. Pat. No. 4,987,071, herein incorporated by reference.

vii. Small Interfering RNA or Micro RNA

In some embodiments of the invention, inhibition of the expression of one or more IPT polypeptides may be obtained by RNA interference by expression of a gene encoding a micro RNA (miRNA). miRNAs are regulatory agents consisting of about 22 ribonucleotides. miRNA are highly efficient at inhibiting the expression of endogenous genes. See, for example, Javier, et al., (2003) *Nature* 425:257-263, herein incorporated by reference.

For miRNA interference, the expression cassette is designed to express an RNA molecule that is modeled on an endogenous miRNA gene. The miRNA gene encodes an RNA that forms a hairpin structure containing a 22-nucleotide sequence that is complementary to another endogenous gene (target sequence). For suppression of IPT polypeptide expression, the 22-nucleotide sequence is selected from an IPT polypeptide transcript sequence and contains 22 nucleotides encoding said IPT polypeptide sequence in sense orientation and 21 nucleotides of a corresponding antisense sequence that is complementary to the sense sequence. miRNA molecules are highly efficient at inhibiting the expression of endogenous genes and the RNA interference they induce is inherited by subsequent generations of plants.

2. Polypeptide-Based Inhibition of Gene Expression

In one embodiment, the polynucleotide encodes a zinc finger protein that binds to a gene encoding an IPT polypeptide, resulting in reduced expression of the gene. In particular embodiments, the zinc finger protein binds to a regulatory region of an IPT polypeptide gene. In other embodiments, the zinc finger protein binds to a messenger RNA encoding an IPT polypeptide and prevents its translation. Methods of selecting sites for targeting by zinc finger proteins have been described, for example, in U.S. Pat. No. 6,453,242, and methods for using zinc finger proteins to inhibit the expression of genes in plants are described, for example, in US Patent Application Publication Number 2003/0037355; each of which is herein incorporated by reference.

3. Polypeptide-Based Inhibition of Protein Activity

In some embodiments of the invention, the polynucleotide encodes an antibody that binds to at least one IPT polypeptide, and reduces the cytokinin synthesis activity of the IPT polypeptide. In another embodiment, the binding of the antibody results in increased turnover of the antibody-IPT polypeptide complex by cellular quality control mechanisms. The expression of antibodies in plant cells and the inhibition of molecular pathways by expression and binding of antibodies to proteins in plant cells are well known in the art. See, for example, Conrad and Sonnewald, (2003) *Nature Biotech.* 21:35-36, incorporated herein by reference.

4. Gene Disruption

In some embodiments of the present invention, the activity of an IPT polypeptide is reduced or eliminated by disrupting the gene encoding the IPT polypeptide. The gene encoding the IPT polypeptide may be disrupted by any method known in the art. For example, in one embodiment, the gene is disrupted by transposon tagging. In another embodiment, the gene is disrupted by mutagenizing plants using random or targeted mutagenesis, and selecting for plants that have reduced IPT activity.

i. Transposon Tagging

In one embodiment of the invention, transposon tagging is used to reduce or eliminate the cytokinin synthesis activity of one or more IPT polypeptides. Transposon tagging comprises inserting a transposon within an endogenous IPT gene to reduce or eliminate expression of the IPT polypeptide. "IPT gene" is intended to mean the gene that encodes an IPT polypeptide according to the invention.

In this embodiment, the expression of one or more IPT polypeptides is reduced or eliminated by inserting a transposon within a regulatory region or coding region of the gene encoding the IPT polypeptide. A transposon that is within an exon, intron, 5' or 3' untranslated sequence, a promoter, or any other regulatory sequence of an IPT polypeptide gene may be used to reduce or eliminate the expression and/or activity of the encoded IPT polypeptide.

Methods for the transposon tagging of specific genes in plants are well known in the art. See, for example, Maes, et al., (1999) *Trends Plant Sci.* 4:90-96; Dharmapuri and Sonti, (1999) *FEMS Microbiol. Lett.* 179:53-59; Meissner, et al., (2000) *Plant J.* 22:265-274; Phogat, et al., (2000) *J. Biosci.* 25:57-63; Walbot, (2000) *Curr. Opin. Plant Biol.* 2:103-107; Gai, et al., (2000) *Nucleic Acids Res.* 28:94-96; Fitzmaurice, et al., (1999) *Genetics* 153:1919-1928). In addition, the TUSC process for selecting Mu insertions in selected genes has been described in Bensen, et al., (1995) *Plant Cell* 7:75-84; Mena, et al., (1996) *Science* 274:1537-1540 and U.S. Pat. No. 5,962,764; each of which is herein incorporated by reference.

ii. Mutant Plants with Reduced Activity

Additional methods for decreasing or eliminating the expression of endogenous genes in plants are also known in the art and can be similarly applied to the instant invention. These methods include other forms of mutagenesis, such as ethyl methanesulfonate-induced mutagenesis, deletion mutagenesis, and fast neutron deletion mutagenesis used in a reverse genetics sense (with PCR) to identify plant lines in which the endogenous gene has been deleted. For examples of these methods see Ohshima, et al., (1998) *Virology* 243:472-481; Okubara, et al., (1994) *Genetics* 137:867-874 and Quesada, et al., (2000) *Genetics* 154:421-436; each of which is herein incorporated by reference. In addition, a fast and automatable method for screening for chemically induced mutations, TILLING (Targeting Induced Local Lesions In Genomes), using denaturing HPLC or selective endonuclease digestion of selected PCR products is also applicable to the instant invention. See, McCallum, et al., (2000) *Nat. Biotechnol.* 18:455-457, herein incorporated by reference.

Mutations that impact gene expression or that interfere with the function (IPT activity) of the encoded protein are well known in the art. Insertional mutations in gene exons usually result in null-mutants. Mutations in conserved residues are particularly effective in inhibiting the cytokinin synthesis activity of the encoded protein. Conserved residues of plant IPT polypeptides suitable for mutagenesis with the goal to eliminate IPT activity have been described. See, for example, FIG. 1. Such mutants can be isolated according to well-known procedures, and mutations in different IPT loci can be stacked by genetic crossing. See, for example, Gruis, et al., (2002) *Plant Cell* 14:2863-2882.

In another embodiment of this invention, dominant mutants can be used to trigger RNA silencing due to gene inversion and recombination of a duplicated gene locus. See, for example, Kusaba, et al., (2003) *Plant Cell* 15:1455-1467.

The invention encompasses additional methods for reducing or eliminating the activity of one or more IPT polypeptides. Examples of other methods for altering or mutating a genomic nucleotide sequence in a plant are known in the art and include, but are not limited to, the use of RNA:DNA vectors, RNA:DNA mutational vectors, RNA:DNA repair vectors, mixed-duplex oligonucleotides, self-complementary RNA:DNA oligonucleotides, and recombinogenic oligonucleobases. Such vectors and methods of use are known in the art. See, for example, U.S. Pat. Nos. 5,565,350; 5,731,181; 5,756,325; 5,760,012; 5,795,972 and 5,871,984; each of which are herein incorporated by reference. See also, WO 98/49350, WO 99/07865, WO 99/25821 and Beetham, et al., (1999) *Proc. Natl. Acad. Sci. USA* 96:8774-8778; each of which is herein incorporated by reference.

III. Modulating Cytokinin Level and/or Activity

As used herein, "cytokinin" refers to a class, or member of the class, of plant-specific hormones that play a central role during the cell cycle and influence numerous developmental programs. Cytokinins comprise an $N^6$-substituted purine derivative. Representative cytokinins include isopentenyladenine ($N^6$-($\Delta^2$-isopentenyl)adenine (hereinafter, iP), zeatin (6-(4-hydroxy-3-methylbut-trans-2-enylamino) purine) (hereinafter, Z), and dihydrozeatin (DZ). The free bases and their ribosides (iPR, ZR, and DZR) are believed to be the active compounds. Additional cytokinins are known. See, for example, U.S. Pat. No. 5,211,738 and Keiber, et al., (2002) *Cytokinins, The Arabidopsis Book*, American Society of Plant Biologists, both of which are herein incorporated by reference.

"Modulating the cytokinin level" includes any statistically significant decrease or increase in cytokinin level and/or activity in the plant when compared to a control plant. For example, modulating the level and/or activity can comprise either an increase or a decrease in overall cytokinin content of about 0.1%, 0.5%, 1%, 3% 5%, 10%, 15%, 20%, 25%, 30%, 35%, 40%, 45%, 50%, 55%, 60%, 65%, 70%, 75%, 80%, 85%, 90%, 95% or greater when compared to a control plant or plant part. Alternatively, the modulated level and/or activity of the cytokinin can include about a 0.2 fold, 0.5 fold, 2 fold, 4 fold, 8 fold, 16 fold, 32 fold or greater overall increase or decrease in cytokinin level/activity in the plant or a plant part when compared to a control plant or plant part.

It is further recognized that the modulation of the cytokinin level/activity need not be an overall increase/decrease in cytokinin level and/or activity, but also includes a change in tissue distribution of the cytokinin. Moreover, the modulation of the cytokinin level/activity need not be an overall increase/decrease in cytokinins, but also includes a change in the ratio of various cytokinin derivatives. For example, the ratio of various cytokinin derivatives such as isopentenyladenine-type, zeatin-type or dihydrozeatin-type cytokinins, and the like, could be altered and thereby modulate the level/activity of the cytokinin of the plant or plant part when compared to a control plant.

Methods for assaying a modulation in cytokinin level and/or activity are known in the art. For example, representative methods for cytokinin extraction, immunopurification, HPLC separation, and quantification by ELISA methods can be found, for example, in Faiss, et al., (1997) *Plant J.* 12:401-415. See, also, Werner, et al., (2001) *PNAS* 98:10487-10492) and Dewitte, et al., (1999) *Plant Physiol.* 119:111-121. Each of these references is herein incorporated by reference. As discussed elsewhere herein, modulation in cytokinin level and/or activity can further be detected by monitoring for particular plant phenotypes. Such phenotypes are described elsewhere herein.

In specific methods, the level and/or activity of a cytokinin in a plant is increased by increasing the level or activity of the IPT polypeptide in the plant. Methods for increasing the level and/or activity of IPT polypeptides in a plant are discussed elsewhere herein. Briefly, such methods comprise providing an IPT polypeptide of the invention to a plant and thereby increasing the level and/or activity of the IPT polypeptide. In other embodiments, an IPT nucleotide sequence encoding an IPT polypeptide can be provided by introducing into the plant a polynucleotide comprising an IPT nucleotide sequence of the invention, expressing the IPT sequence, and thereby increasing the level and/or activity of a cytokinin in the plant or plant part when compared to a control plant. In some embodiments, the IPT nucleotide construct introduced into the plant is stably incorporated into the genome of the plant.

In other methods, the level and/or activity of cytokinin in a plant is decreased by decreasing the level and/or activity of one or more of the IPT polypeptides in the plant. Such methods are disclosed in detail elsewhere herein. In one such method, an IPT nucleotide sequence is introduced into the plant and expression of the IPT nucleotide sequence decreases the activity of the IPT polypeptide, and thereby decreases the level and/or activity of a cytokinin in the plant or plant part when compared to a control plant or plant part. In other embodiments, the IPT nucleotide construct introduced into the plant is stably incorporated into the genome of the plant.

As discussed above, one of skill will recognize the appropriate promoter to use to modulate the level/activity of a cytokinin in the plant. Exemplary promoters for this embodiment have been disclosed elsewhere herein.

Accordingly, the present invention further provides plants having a modulated level/activity of a cytokinin when compared to the cytokinin level/activity of a control plant. In one embodiment, the plant of the invention has an increased level/activity of the IPT polypeptide of the invention, and thus has an increased level/activity of cytokinin. In other embodiments, the plant of the invention has a reduced or eliminated level of the IPT polypeptide of the invention, and thus has a decreased level/activity of a cytokinin. In certain embodiments, such plants have stably incorporated into their genome a nucleic acid molecule comprising an IPT nucleotide sequence of the invention operably linked to a promoter that drives expression in the plant cell.

IV. Modulating Root Development

Methods for modulating root development in a plant are provided. By "modulating root development" is intended any alteration in the development of the plant root when compared to a control plant. Such alterations in root development include, but are not limited to, alterations in the growth rate of the primary root, the fresh root weight, the extent of lateral and adventitious root formation, the vasculature system, meristem development, or radial expansion.

Methods for modulating root development in a plant are provided. The methods comprise modulating the level and/or activity of the IPT polypeptide in the plant. In one method, an IPT sequence of the invention is provided to the plant. In another method, the IPT nucleotide sequence is provided by introducing into the plant a polynucleotide comprising an IPT nucleotide sequence of the invention (which may be a fragment of a full-length IPT sequence provided), expressing said IPT sequence, and thereby modifying root development. In still other methods, the IPT nucleotide construct introduced into the plant is stably incorporated into the genome of the plant.

In other methods, root development is modulated by decreasing the level or activity of the IPT polypeptide in the plant. Such methods can comprise introducing an IPT nucleotide sequence into the plant and decreasing the activity of the IPT polypeptide. In some methods, the IPT nucleotide construct introduced into the plant is stably incorporated into the genome of the plant. A decrease in cytokinin synthesis activity can result in at least one or more of the following alterations to root development, including, but not limited to, larger root meristems, increased root growth, enhanced radial expansion, an enhanced vasculature system, increased root branching, more adventitious roots and/or an increase in fresh root weight when compared to a control plant.

As used herein, "root growth" encompasses all aspects of growth of the different parts that make up the root system at different stages of its development in both monocotyledonous and dicotyledonous plants. It is to be understood that enhanced root growth can result from enhanced growth of one or more of its parts including the primary root, lateral roots, adventitious roots, etc. Methods of measuring such developmental alterations in the root system are known in the art. See, for example, US Patent Application Publication Number 2003/0074698 and Werner, et al., (2001) PNAS 18:10487-10492, both of which are herein incorporated by reference.

As discussed above, one of skill will recognize the appropriate promoter to use to modulate root development in the plant. Exemplary promoters for this embodiment include constitutive promoters and root-preferred promoters. Exemplary root-preferred promoters have been disclosed elsewhere herein.

Stimulating root growth and increasing root mass by decreasing the activity and/or level of the IPT polypeptide also finds use in improving the standability of a plant. The term "resistance to lodging" or "standability" refers to the ability of a plant to fix itself to the soil. For plants with an erect or semi-erect growth habit, this term also refers to the ability to maintain an upright position under adverse environmental conditions. This trait relates to the size, depth and morphology of the root system. In addition, stimulating root growth and increasing root mass by decreasing the level and/or activity of the IPT polypeptide at appropriate developmental stages also finds use in promoting in vitro propagation of explants.

Increased root biomass and/or altered root architecture may also find use in improving nitrogen-use efficiency of the plant. Such improved efficiency may lead to, for example, an increase in plant biomass and/or seed yield at an existing level of available nitrogen, or maintenance of plant biomass and/or seed yield when available nitrogen is limited. Thus, agronomic and/or environmental benefits may ensue.

Furthermore, higher root biomass production due to a decreased level and/or activity of an IPT polypeptide has an indirect effect on production of compounds produced by root cells or transgenic root cells or cell cultures of said transgenic root cells. One example of an interesting compound produced in root cultures is shikonin, the yield of which can be advantageously enhanced by said methods.

Accordingly, the present invention further provides plants having modulated root development when compared to the root development of a control plant. In some embodiments, the plant of the invention has a decreased level/activity of an IPT polypeptide of the invention and has enhanced root growth and/or root biomass. In certain embodiments, such plants have stably incorporated into their genome a nucleic acid molecule comprising an IPT nucleotide sequence of the invention operably linked to a promoter that drives expression in the plant cell.

V. Modulating Shoot and Leaf Development

Methods are also provided for modulating vegetative tissue growth in plants. In one embodiment, shoot and leaf development in a plant is modulated. By "modulating shoot and/or leaf development" is intended any alteration in the development of the plant shoot and/or leaf when compared to a control plant or plant part. Such alterations in shoot and/or leaf development include, but are not limited to, alterations in shoot meristem development, in leaf number, leaf size, leaf and stem vasculature, internode length and leaf senescence. As used herein, "leaf development" and "shoot development" encompasses all aspects of growth of the different parts that make up the leaf system and the shoot system, respectively, at different stages of their development, both in monocotyledonous and dicotyledonous plants. Methods for measuring such developmental alterations in the shoot and leaf system are known in the art. See, for example, Werner, et al., (2001) PNAS 98:10487-10492 and US Patent Application Publication Number 2003/0074698, each of which is herein incorporated by reference.

The method for modulating shoot and/or leaf development in a plant comprises modulating the activity and/or level of an IPT polypeptide of the invention. In one embodiment, an IPT sequence of the invention is provided. In other embodiments, the IPT nucleotide sequence can be provided by introducing into the plant a polynucleotide comprising an IPT nucleotide sequence of the invention, expressing the IPT sequence, and thereby modifying shoot and/or leaf development. In other embodiments, the IPT nucleotide construct introduced into the plant is stably incorporated into the genome of the plant.

In specific embodiments, shoot or leaf development is modulated by decreasing the level and/or activity of the IPT polypeptide in the plant. A decrease in IPT activity can result in one or more alterations in shoot and/or leaf development, including, but not limited to, smaller apical meristems, reduced leaf number, reduced leaf surface, reduced vascular tissues, shorter internodes and stunted growth, and accelerated leaf senescence, when compared to a control plant.

As discussed above, one of skill will recognize the appropriate promoter to use to modulate shoot and leaf development of the plant. Exemplary promoters for this embodiment include constitutive promoters, shoot-preferred promoters, shoot meristem-preferred promoters, senescence-activated promoters, stress-induced promoters, root-preferred promoters, nitrogen-induced promoters and leaf-preferred promoters. Exemplary promoters have been disclosed elsewhere herein.

Decreasing cytokinin synthesis activity in a plant generally results in shorter internodes and stunted growth. Thus, the methods of the invention find use in producing dwarf plants.

In addition, as discussed above, modulation of cytokinin synthesis activity in the plant modulates both root and shoot growth. Thus, the present invention further provides methods for altering the root/shoot ratio.

Shoot or leaf development can further be modulated by increasing the level and/or activity of the IPT polypeptide in the plant. An increase in IPT activity can result in one or more alterations in shoot and/or leaf development including, but not limited to, increased leaf number, increased leaf surface, increased vascular tissue, increased shoot formation, longer internodes, improved growth, improved plant yield and vigor and retarded leaf senescence when compared to a control plant.

In one embodiment, the tolerance of a plant to flooding is improved. Flooding is a serious environmental stress that affects plant growth and productivity. Flooding causes premature senescence which results in leaf chlorosis, necrosis, defoliation, cessation of growth and reduced yield. Cytokinins can regulate senescence, and by increasing the level/activity of the IPT polypeptide in the plant, the present invention improves the tolerance of the plant to a variety of environmental stresses, including flooding. Delayed senescence may also advantageously expand the maturity adaptation of crops, improve the shelf-life of potted plants, and extend the vase-life of cut flowers.

In still other embodiments, methods for modulating shoot regeneration in a callus are provided. In this method, increasing the level and/or activity of the IPT polypeptide will increase the level of cytokinins in the plant. Accordingly, lower concentrations of exogenous growth regulators (i.e., cytokinins) or no exogenous cytokinins in the culture medium will be needed to enhance shoot regeneration in callus. Thus, in one embodiment of the invention, the increased level and/or activity of the IPT sequence can be used to overcome the poor shooting potential of certain species that has limited the success and speed of transgene technology for those species. Moreover, multiple shoot induction can be induced for crops where it is economically desirable to produce as many shoots as possible. Accordingly, methods are provided to increase the rate of regeneration for transformation. In specific embodiments, the IPT sequence will be under the control of an inducible promoter (e.g., heat shock promoter, chemically inducible promoter). Additional inducible promtors are known in the art and are discussed elsewhere herein.

Methods for establishing callus from explants are known. For example, roots, stems, buds and aseptically germinated seedlings are just a few of the sources of tissue that can be used to induce callus formation. Generally, young and actively growing tissues (i.e., young leaves, roots, meristems or other tissues) are used, but are not required. Callus formation is controlled by growth regulating substances present in the medium (auxins and cytokinins). The specific concentrations of plant regulators needed to induce callus formation vary from species to species and can even depend on the source of explant. In some instances, it is advised to use different growth substances (e.g., 2, 4-D or NAA) or a combination of them during tests, since some species may not respond to a specific growth regulator. In addition, culture conditions (i.e., light, temperature, etc.) can also influence the establishment of callus. Once established, callus cultures can be used to initiate shoot regeneration. See, for example, Gurel, et al., (2001) *Turk J. Bot.* 25:25-33; Dodds, et al., (1995). Experiments in Plant Tissue Culture, Cambridge University Press; Gamborg (1995) *Plant Cell, Tissue and Organ Culture*, eds. Phillips and US Patent Application Publciation Number 2003/0180952, all of which are herein incorporated by reference.

It is further recognized that increasing seed size and/or weight can be accompanied by an increase in the rate of growth of seedlings or an increase in vigor. In addition, modulating the plant's tolerance to stress, as discussed elsewhere herein, along with modulation of root, shoot and leaf development, can increase plant yield and vigor. As used herein, the term "vigor" refers to the relative health, productivity and rate of growth of the plant and/or of certain plant parts, and may be reflected in various developmental attributes, including, but not limited to, concentration of chlorophyll, photosynthetic rate, total biomass, root biomass, grain quality and/or grain yield. In *Zea mays* in particular, vigor may also be reflected in ear growth rate, ear size and/or expansiveness of silk exsertion. Vigor may relate to the ability of a plant to grow rapidly during early development and to the successful establishment, after germination, of a well-developed root system and a well-developed photosynthetic apparatus. Vigor may be determined with reference to different genotypes under similar environmental conditions, or with reference to the same or different genotypes under different environmental conditions.

Accordingly, the present invention further provides plants having modulated shoot and/or leaf development when compared to a control plant. In some embodiments, the plant of the invention has an increased level/activity of the IPT polypeptide of the invention. In other embodiments, the plant of the invention has a decreased level/activity of the IPT polypeptide of the invention.

VI. Modulating Reproductive Tissue Development

Abortion of flowers and pods is a common occurrence in soybeans and is believed to limit yield (Abernethy, et al., (1997) *Can J Plant Sci* 57:713-716; Dybing, et al., (1986) *Plant Physiol* 81:1069-1074). Cytokinins have been shown to play an important role during flower and pod development. Exogenous application of benzyladenine (a cytokinin) to the raceme decreases abortion of flowers and/or pods (Dyer, et al., (1988) In: Pharis and Rood, eds. *Plant growth substances*. New York: Springer-Verlag, 457-467; Peterson, et al., (1990) *Botanical Gazette* 151:322-330; Mosjidis, et al., (1993) *Annals of Botany* 71:193-199; Reese, et al., (1995) *J Exptl Botany* 46(289):957-964) and a strong body of evidence supports a role for cytokinins in the regulation of flowering and seed setting in soybean (Huff and Dybing, (1980) *J Exptl Botany* 31:51-762; Ghiasi, et al., (1987) *Plant Physiol* 81:1069-1074; Peterson, et al., (1990) *Botanical Gazette* 151:322-330; Wiebold, (1990) *Agron J* 82:85-88; Mosjidis, et al., (1993), supra; Reese, et al., (1995), supra; Nagel, et al., (2001) *Annals of Botany* 88:27-31). Increased number of pods and seed yields in response to cytokinin treatments support the hypothesis that increasing cytokinin concentration in developing flowers and pods using appropriate promoters would result in increased total seed production of soybean plants.

Methods for modulating reproductive tissue development are provided. In one embodiment, methods are provided to modulate floral development in a plant. By "modulating floral development" is intended any alteration in a structure of a plant's reproductive tissue as compared to a control plant or plant part. "Modulating floral development" further includes any alteration in the timing of the development of a plant's reproductive tissue (i.e., delayed or accelerated floral development) when compared to a control plant or plant part. Macroscopic alterations may include changes in size, shape, number or location of reproductive organs, the developmental time period during which these structures form, or the ability to maintain or proceed through the flowering process in times of environmental stress. Microscopic alterations may include changes to the types or shapes of cells that make up the reproductive organs.

The method for modulating floral development in a plant comprises modulating (either increasing or decreasing) the level and/or activity of the IPT polypeptide in a plant. In one method, an IPT sequence of the invention is provided. An IPT nucleotide sequence can be provided by introducing into the plant a polynucleotide comprising an IPT nucleotide sequence of the invention, expressing the IPT sequence, and thereby modifying floral development. In some embodiments, the IPT nucleotide construct introduced into the plant is stably incorporated into the genome of the plant.

As discussed above, one of skill will recognize the appropriate promoter to use to modulate floral development in the plant. Exemplary promoters for this embodiment include constitutive promoters, inducible promoters, shoot-preferred promoters and inflorescence-preferred promoters (including developing-female-inflorescence-preferred promoters), including those listed elsewhere herein.

In specific methods, floral development is modulated by increasing the level and/or activity of the IPT sequence of the invention. Such methods can comprise introducing an IPT nucleotide sequence into the plant and increasing the activity of the IPT polypeptide. In some methods, the IPT nucleotide construct introduced into the plant is stably incorporated into the genome of the plant. An increase in the level and/or activity of the IPT sequences can result in one or more alterations in floral development including, but not limited to, accelerated flowering, increased number of flowers, and improved seed set when compared to a control plant. In addition, an increase in the level or activity of the IPT sequences can result in the prevention of flower senescence and an alteration in embryo number per kernel. See, Young, et al., (2004) *Plant J.* 38:910-22. Methods for measuring such developmental alterations in floral development are known in the art. See, for example, Mouradov, et al., (2002) *The Plant Cell* S111-S130, herein incorporated by reference.

In other methods, floral development is modulated by decreasing the level and/or activity of the IPT sequence of the invention. A decrease in the level and/or activity of the IPT sequence can result in kernel abortion and infertile female inflorescence. Inducing delayed flowering or inhibiting flowering can be used to enhance yield in forage crops such as alfalfa.

Accordingly, the present invention further provides plants having modulated floral development when compared to the floral development of a control plant. Compositions include plants having a decreased level/activity of the IPT polypeptide of the invention and having an altered floral development. Compositions also include plants having an increased level/activity of the IPT polypeptide of the invention wherein the plant maintains or proceeds through the flowering process in times of stress.

VII. Modulating the Stress Tolerance of a Plant

Methods are provided for the use of the IPT sequences of the invention to modify the tolerance of a plant to abiotic stress. Increased growth of seedlings or early vigor is often associated with an increase in stress tolerance. For example, faster development of seedlings, including the root system of seedlings upon germination, is critical for survival, particularly under adverse conditions such as drought. Promoters that can be used in this method are described elsewhere herein, including low-level constitutive, inducible, or root-preferred promoters, such as root-preferred promoters derived from ZmIPT4 and ZmIPT5 regulatory sequences. Accordingly, in one method of the invention, a plant's tolerance to stress is increased or maintained when compared to a control plant by decreasing the level of IPT activity in the germinating seedling. In other methods, an IPT nucleotide sequence is provided by introducing into the plant a polynucleotide comprising a IPT nucleotide sequence of the invention, expressing the IPT sequence, and thereby increasing the plant's tolerance to stress. In other embodiments, the IPT nucleotide construct introduced into the plant is stably incorporated into the genome of the plant.

Methods are also provided to increase or maintain seed set during abiotic stress episodes. During periods of stress (i.e., drought, salt, heavy metals, temperature, etc.) embryo development is often aborted. In maize, halted embryo development results in aborted kernels on the ear (Cheikh and Jones, (1994) *Plant Physiol.* 106:45-51; Dietrich, et al., (1995) *Plant Physiol Biochem* 33:327-336). In soy, abortion of pods prior to seed maturation can reduce seed yield and is observed during both optimal and stress conditions. Preventing this seed loss will maintain yield. Accordingly, methods are provided to increase the stress resistance in a plant (e.g., during flowering and seed development). Increasing expression of the IPT sequence of the invention can also modulate floral development during periods of stress, and thus methods are provided to maintain or improve the flowering process in plants under stress. The method comprises increasing the level and/or activity of the IPT sequence of the invention. In one method, an IPT nucleotide sequence is introduced into the plant and the level and/or activity of the IPT polypeptide is increased, thereby maintaining or improving the tolerance of the plant under stress conditions. In other methods, the IPT nucleotide construct introduced into the plant is stably incorporated into the genome of the plant. See, for example, WO 00/63401.

Significant yield instability can occur as a result of unfavorable environments during the lag phase of seed development. During this period, seeds undergo dramatic changes in ultra structure, biochemistry, and sensitivity to environmental perturbation, yet demonstrate little change in dry mass accumulation. Two important events that occur during the lag phase are initiation and division of endosperm cells and amyloplasts (which are the sites for starch deposition). It has been demonstrated that during the lag phase (around 10-12 days after pollination (DAP) in maize) a dramatic increase in cytokinin concentration immediately precedes maximum rates of endosperm cell division and amyloplast formation, indicating that this hormone plays a central role in these processes and in what is called the 'sink strength' of the developing seed. Cytokinins have been demonstrated to play an important role in establishing seed size, decreasing seed abortion, and increasing seed set during unfavorable environmental conditions. For example, elevated temperatures affect seed formation. Elevated temperatures can inhibit the accumulation of cytokinin, decrease endosperm cell division and amyloplast number, and as a consequence, increase kernel abortion.

In crop species such as maize, kernel sink capacity is principally a function of the number of endosperm cells and starch granules established during the first 6 to 12 DAP. The final number of endosperm cells and amyloplasts formed is highly correlated with final kernel weight. (Capitanio, et al., (1983); Reddy and Daynard, (1983); Jones, et al., (1985) (1996); Engelen-Eigles, et al., (2000)). Hormones, especially cytokinins, have been shown to stimulate cell division, plastid initiation and other processes important in the establishment of kernel sink capacity (Davies, (1987)). Cytokinin levels could for example be manipulated in soybean using the GmIPT2 promoter to drive the expression of the *Agrobacterium* IPT gene. Similarly, endosperm- and/or pedicel-preferred promoters could be used to increase the level and/or duration of expression of GmIPT2, which would result in an increase of cytokinin levels which would in turn increase flowers/pods retention, increasing sink strength and yield. Methods are therefore provided to increase the activity and/or level of IPT polypeptides in the developing inflorescence, thereby elevating cytokinin levels and allowing developing seed to achieve their full genetic potential for size, minimize pod and/or seed abortion, and buffer seed set during unfavorable environments. The methods further allow the plant to maintain and/or improve the flowering process during unfavorable environments.

In this embodiment, a variety of promoters could be used to direct the expression of a sequence capable of increasing the level and/or activity of the IPT polypeptide, including but not limited to, constitutive promoters, seed-preferred promoters, developing-seed promoters, meristem-preferred promoters, stress-induced promoters and inflorescence-preferred (such as developing female inflorescence promoters). In one method, a promoter that is stress insensitive and is expressed in a tissue of the developing seed during the lag phase of development is used. By "insensitive to stress" is intended that the expression level of a sequence operably linked to the promoter is not altered or only minimally altered under stress conditions. By "lag phase" promoter is intended a promoter that is active in the lag phase of seed development. A description of this developmental phase is found elsewhere herein. By "developing-seed-preferred" is intended a promoter that allows for enhanced IPT expression within a developing seed. Such promoters that are stress insensitive and are expressed in a tissue of the developing seed during the lag phase of development are known in the art and include Zag2.1 (Theissen, et al., (1995) Gene 156:155-166, Genbank Accession Number X80206) and mzE40 (Zm40) (U.S. Pat. No. 6,403,862 and WO01/2178).

An expression construct may further comprise nucleotide sequences encoding peptide signal sequences in order to effect changes in cytokinin level and/or activity in the mitochondria or chloroplasts. See, for example, Neupert, (1997) *Annual Rev. Biochem.* 66:863-917; Glaser, et al., (1998) *Plant Molecular Biology* 38:311-338; Duby, et al., (2001) *The Plant J* 27(6):539-549.

Methods to assay for an increase in seed set during abiotic stress are known in the art. For example, plants having the increased IPT activity can be monitored under various stress conditions and compared to control plants. For instance, the plant having the increased cytokinin synthesis activity can be subjected to various degrees of stress during flowering and seed set. Under identical conditions, the genetically modified plant having the increased cytokinin synthesis activity will have a higher number of developing pods and/or seeds than a control plant.

Accordingly, the present invention further provides plants having increased yield or a maintained yield and/or an increased or maintained flowering process during periods of abiotic stress (drought, salt, heavy metals, temperature extremes, etc.). In some embodiments, the plants having an increased or maintained yield during abiotic stress have an increased level/activity of the IPT polypeptide of the invention. In some embodiments, the plant comprises an IPT nucleotide sequence of the invention operably linked to a promoter that drives expression in the plant cell. In some embodiments, such plants have stably incorporated into their genome a nucleic acid molecule comprising an IPT nucleotide sequence of the invention operably linked to a promoter that drives expression in the plant cell.

VIII. Antibody Creation and Use

Antibodies can be raised to a protein of the present invention, including variants and fragments thereof, in both their naturally-occurring and recombinant forms. Many methods of making antibodies are known to persons of skill. A variety of analytic methods are available to generate a hydrophilicity profile of a protein of the present invention. Such methods can be used to guide the artisan in the selection of peptides of the present invention for use in the generation or selection of antibodies which are specifically reactive, under immunogenic conditions, to a protein of the present invention. See, e.g., Janin, (1979) *Nature* 277:491-492; Wolfenden, et al., (1981) *Biochemistry* 208:49-855; Kyte and Doolite, (1982) *J. Mol. Biol.* 157:105-132; Rose, et al., (1985) *Science* 229:834-838. The antibodies can be used to screen expression libraries for particular expression products such as normal or abnormal protein, or altered levels of the same, which may be useful for detecting or diagnosing various conditions related to the presence of the respective antigens. Assays indicating high levels of an IPT protein of the invention, for example, could be useful in detecting plants, or specific plant parts, with elevated cytokinin levels. Usually the antibodies in such a procedure are labeled with a moiety which allows easy detection of presence of antigen/antibody binding.

The following discussion is presented as a general overview of the techniques available; however, one of skill will recognize that many variations upon the following methods are known.

A number of immunogens are used to produce antibodies specifically reactive with a protein of the present invention. Polypeptides encoded by isolated recombinant, synthetic, or native polynucleotides of the present invention are the preferred antigens for the production of monoclonal or polyclonal antibodies. Polypeptides of the present invention are optionally denatured, and optionally reduced, prior to injection into an animal capable of producing antibodies. Either monoclonal or polyclonal antibodies can be generated for subsequent use in immunoassays to measure the presence and quantity of the protein of the present invention. Methods of producing polyclonal antibodies are known to those of skill in the art. In brief, an antigen, preferably a purified protein, a protein coupled to an appropriate carrier (e.g., GST, keyhole limpet hemanocyanin, etc.), or a protein incorporated into an immunization vector such as a recombinant vaccinia virus (see, U.S. Pat. No. 4,722,848) is mixed with an adjuvant and animals are immunized with the mixture. The animal's immune response to the immunogen preparation is monitored by taking test bleeds and determining the titer of reactivity to the protein of interest. When appropriately high titers of antibody to the immunogen are obtained, blood is collected from the animal and antisera are prepared. Specific monoclonal and polyclonal antibodies will usually have an antibody binding site with an affinity constant for its cognate monovalent antigen at least between $10^6$-$10^7$, usually at least $10^8$, $10^9$, $10^{10}$ and up to about $10^{11}$ liters/mole. Further fractionation of the antisera to enrich for antibodies reactive to the protein is performed where desired (See, e.g., Coligan, (1991) *Current Protocols in Immunology*, Wiley/Greene, NY; and Harlow and Lane, (1989) *Antibodies: A Laboratory Manual*, Cold Spring Harbor Press, NY).

Antibodies, including binding fragments and single chain recombinant versions thereof, against predetermined fragments of a protein of the present invention are raised by immunizing animals, e.g., with conjugates of the fragments with carrier proteins as described above. Typically, the immunogen of interest is a protein of at least about 5 amino acids, more typically the protein is 10 amino acids in length, often 15 to 20 amino acids in length and may be longer. The peptides are typically coupled to a carrier protein (e.g., as a fusion protein), or are recombinantly expressed in an immunization vector. Antigenic determinants on peptides to which antibodies bind are typically 3 to 10 amino acids in length.

Monoclonal antibodies are prepared from hybrid cells secreting the desired antibody. Monoclonal antibodies are screened for binding to a protein from which the antigen was derived. Description of techniques for preparing such monoclonal antibodies are found in, e.g., *Basic and Clinical Immunology*, 4th ed., Stites, et al., Eds., Lange Medical Publications, Los Altos, Calif., and references cited therein; Harlow and Lane, Supra; Goding, (1986) *Monoclonal Antibodies: Principles and Practice*, 2nd ed., Academic Press, New York, N.Y. and Kohler and Milstein, (1975) *Nature* 256:495-497. Summarized briefly, this method proceeds by injecting an animal with an antigen comprising a protein of the present invention. The animal is then sacrificed and cells taken from its spleen, which are fused with myeloma cells. The result is a hybrid cell or "hybridoma" that is capable of reproducing in vitro. The population of hybridomas is then screened to isolate individual clones, each of which secretes a single antibody species to the antigen. In this manner, the individual antibody species obtained are the products of immortalized and cloned single B cells generated by the animal in response to a specific site recognized on the antigenic substance.

Other suitable techniques involve selection of libraries of recombinant antibodies in phage or similar vectors (see, e.g., Huse, et al., (1989) *Science* 246:1275-1281 and Ward, et al., (1989) *Nature* 341:544-546 and Vaughan, et al., (1996) *Nature Biotechnology*, 14:309-314). Also, recombinant immunoglobulins may be produced. See, Cabilly, U.S. Pat. No. 4,816,567 and Queen, et al. (1989), *Proc. Natl. Acad. Sci.* 86:10029-10033.

Antibodies to the polypeptides of the invention are also used for affinity chromatography in isolating proteins of the present invention. Columns are prepared, e.g., with the antibodies linked to a solid support, e.g., particles, such as agarose, SEPHADEX, or the like, where a cell lysate is passed through the column, washed and treated with increasing concentrations of a mild denaturant, whereby purified proteins are released.

Frequently, the proteins and antibodies of the present invention will be labeled by joining, either covalently or non-covalently, a substance which provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles and the like.

Protein Immunoassays

Means of detecting the proteins of the present invention are not critical aspects of the present invention. In certain examples, the proteins are detected and/or quantified using any of a number of well-recognized immunological binding assays (see, e.g., U.S. Pat. Nos. 4,366,241; 4,376,110; 4,517,288 and 4,837,168). For a general review of immunoassays, see also, Methods in Cell Biology, Vol. 37: *Antibodies in Cell Biology*, Asai, Ed., Academic Press, Inc. New York (1993); *Basic and Clinical Immunology* 7th Edition, Stites & Terr, Eds. (1991). Moreover, the immunoassays of the present invention can be performed in any of several configurations, e.g., those reviewed in *Enzyme Immunoassay*, Maggio, Ed., CRC Press, Boca Raton, Fla. (1980); Tijan, Practice and Theory of Enzyme Immunoassays, *Laboratory Techniques in Biochemistry and Molecular Biology*, Elsevier Science Publishers B.V., Amsterdam (1985); Harlow and Lane, supra; *Immunoassay: A Practical Guide*, Chan, Ed., Academic Press, Orlando, Fla. (1987); *Principles and Practice of Immunoassaysm*, Price and Newman Eds., Stockton Press, NY (1991) and *Non-isotopic Immunoassays*, Ngo, Ed., Plenum Press, NY (1988).

Immunological binding assays (or immunoassays) typically utilize a "capture agent" to specifically bind to and often immobilize the analyte (in this case, a protein of the present invention). The capture agent is a moiety that specifically binds to the analyte. In certain embodiments, the capture agent is an antibody that specifically binds a protein of the present invention. The antibody may be produced by any of a number of means known to those of skill in the art as described herein.

Immunoassays also often utilize a labeling agent to specifically bind to and label the binding complex formed by the capture agent and the analyte. The labeling agent may itself be one of the moieties comprising the antibody/analyte complex. Thus, the labeling agent may be a labeled protein of the present invention or a labeled antibody specifically reactive to a protein of the present invention. Alternatively, the labeling agent may be a third moiety, such as another antibody, that specifically binds to the antibody/protein complex.

Throughout the assays, incubation and/or washing steps may be required after each combination of reagents. Incubation steps can vary from about 5 seconds to several hours, often from about 5 minutes to about 24 hours. However, the incubation time will depend upon the assay format, analyte, volume of solution, concentrations and the like. Usually, the assays will be carried out at ambient temperature, although they can be conducted over a range of temperatures, such as 10° C. to 40° C.

While the details of the immunoassays of the present invention may vary with the particular format employed, the method of detecting a protein of the present invention in a biological sample generally comprises the steps of contacting the biological sample with an antibody which specifically reacts, under immunologically reactive conditions, to a protein of the present invention. The antibody is allowed to bind to the protein under immunologically reactive conditions, and the presence of the bound antibody is detected directly or indirectly.

A. Non-Competitive Assay Formats

Immunoassays for detecting proteins of the present invention include competitive and noncompetitive formats. Non-competitive immunoassays are assays in which the amount of captured analyte (i.e., a protein of the present invention) is directly measured. In one example, the "sandwich" assay, the capture agent (e.g., an antibody specifically reactive, under immunoreactive conditions, to a protein of the present invention) can be bound directly to a solid substrate where it is immobilized. These immobilized antibodies then capture the protein present in the test sample. The protein thus immobilized is then bound by a labeling agent, such as a second antibody bearing a label. Alternatively, the second antibody may lack a label, but it may, in turn, be bound by a labeled third antibody specific to antibodies of the species from which the second antibody is derived. The second antibody can be modified with a detectable moiety, such as biotin, to which a third labeled molecule can specifically bind, such as enzyme-labeled streptavidin.

B. Competitive Assay Formats

In competitive assays, the amount of analyte present in the sample is measured indirectly by measuring the amount of an added (exogenous) analyte (e.g., a protein of the present invention) displaced (or competed away) from a capture agent (e.g., an antibody specifically reactive, under immunoreactive conditions, to the protein) by the analyte present in the sample. In one competitive assay, a known amount of analyte is added to the sample and the sample is then contacted with a capture agent that specifically binds a protein of the present invention. The amount of protein bound to the capture agent is inversely proportional to the concentration of analyte present in the sample.

In one embodiment, the antibody is immobilized on a solid substrate. The amount of protein bound to the antibody may be determined either by measuring the amount of protein present in a protein/antibody complex, or alternatively by measuring the amount of remaining uncomplexed protein. The amount of protein may be detected by providing a labeled protein.

A hapten inhibition assay is another competitive assay. In this assay a known analyte, such as a protein of the present invention, is immobilized on a solid substrate. A known amount of antibody specifically reactive, under immunoreactive conditions, to the protein is added to the sample, and the sample is then contacted with the immobilized protein. In this case, the amount of antibody bound to the immobilized protein is inversely proportional to the amount of protein present in the sample. Again, the amount of immobilized antibody may be determined by detecting either the immobilized fraction of antibody or the fraction of the antibody that remains in solution. Detection may be direct, where the antibody is labeled, or indirect, by the subsequent addition of a labeled moiety that specifically binds to the antibody, as described above.

C. Generation of Pooled Antisera for use in Immunoassays

A protein that specifically binds to, or that is specifically immunoreactive with, an antibody generated against a defined antigen is determined in an immunoassay. The immunoassay uses a polyclonal antiserum which is raised to a polypeptide of the present invention (i.e., the antigenic polypeptide). This antiserum is selected to have low cross-reactivity against other proteins, and any such cross-reactivity is removed by immunoabsorbtion prior to use in the immunoassay (e.g., by immunosorbtion of the antisera with a protein of different substrate specificity (e.g., a different enzyme) and/or a protein with the same substrate specificity but of a different form).

In order to produce antisera for use in an immunoassay, a polypeptide of the present invention is isolated as described herein. For example, recombinant protein can be produced in a mammalian or other eukaryotic cell line. An inbred strain of mice is immunized with the protein using a standard adjuvant, such as Freund's adjuvant, and a standard mouse immunization protocol (see, Harlow and Lane, supra). Alternatively, a synthetic polypeptide derived from the sequences disclosed herein and conjugated to a carrier protein is used as an immunogen. Polyclonal sera are collected and titered against the immunogenic polypeptide in an immunoassay, for example, a solid phase immunoassay with the immunogen immobilized on a solid support. Polyclonal antisera with a titer of $10^4$ or greater are selected and tested for their cross reactivity against polypeptides of different forms or substrate specificity, using a competitive binding immunoassay such as the one described in Harlow and Lane, supra, at pages 570-573. Preferably, two or more distinct forms of polypeptides are used in this determination. These distinct types of polypeptides are used as competitors to identify antibodies which are specifically bound by the polypeptide being assayed for. The competitive polypeptides can be produced as recombinant proteins and isolated using standard molecular biology and protein chemistry techniques as described herein.

Immunoassays in the competitive binding format are used for cross-reactivity determinations. For example, the immunogenic polypeptide is immobilized to a solid support. Proteins added to the assay compete with the binding of the antisera to the immobilized antigen. The ability of the above proteins to compete with the binding of the antisera to the immobilized protein is compared to the immunogenic polypeptide. The percent cross-reactivity for the above proteins is calculated, using standard methods. Those antisera with less than 10% cross-reactivity for a distinct form of a polypeptide are selected and pooled. The cross-reacting antibodies are then removed from the pooled antisera by immunoabsorbtion with a distinct form of a polypeptide.

The immunoabsorbed and pooled antisera are then used in a competitive binding immunoassay as described herein to compare a second "target" polypeptide to the immunogenic polypeptide. In order to make this comparison, the two polypeptides are each assayed at a wide range of concentrations and the amount of each polypeptide required to inhibit 50% of the binding of the antisera to the immobilized protein is determined using standard techniques. If the amount of the target polypeptide required is less than twice the amount of the immunogenic polypeptide that is required, then the target polypeptide is said to specifically bind to an antibody generated to the immunogenic protein. As a final determination of specificity, the pooled antisera is fully immunosorbed with the immunogenic polypeptide until no binding to the polypeptide used in the immunosorbtion is detectable. The fully immunosorbed antisera is then tested for reactivity with the test polypeptide. If no reactivity is observed, then the test polypeptide is specifically bound by the antisera elicited by the immunogenic protein.

D. Other Assay Formats

In certain embodiments, Western blot (immunoblot) analysis is used to detect and quantify the presence of protein of the present invention in the sample. The technique generally comprises separating sample proteins by gel electrophoresis on the basis of molecular weight, transferring the separated proteins to a suitable solid support, (such as a nitrocellulose filter, a nylon filter or derivatized nylon filter), and incubating the sample with the antibodies that specifically bind a protein of the present invention. The antibodies specifically bind to the protein on the solid support. These antibodies may be directly labeled, or may be subsequently detected using labeled antibodies (e.g., labeled sheep anti-mouse antibodies) that specifically bind to the antibodies.

E. Quantification of Proteins.

The proteins of the present invention may be detected and quantified by any of a number of means well known to those of skill in the art. These include analytic biochemical methods such as electrophoresis, capillary electrophoresis, high performance liquid chromatography (HPLC), thin layer chromatography (TLC), hyperdiffusion chromatography and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays and the like.

F. Reduction of Non-Specific Binding

One of skill will appreciate that it is often desirable to reduce non-specific binding in immunoassays and during analyte purification. Where the assay involves an antigen, antibody, or other capture agent immobilized on a solid substrate, it is desirable to minimize the amount of non-specific binding to the substrate. Means of reducing such non-specific binding are well known to those of skill in the art. Typically, this involves coating the substrate with a proteinaceous composition. In particular, protein compositions such as bovine serum albumin (BSA), nonfat powdered milk and gelatin are widely used.

G. Immunoassay Labels

The labeling agent can be, e.g., a monoclonal antibody, a polyclonal antibody, a binding protein or complex or a polymer such as an affinity matrix, carbohydrate or lipid. Detectable labels suitable for use in the present invention include any composition detectable by spectroscopic, radioisotopic, photochemical, biochemical, immunochemical, electrical, optical or chemical means. Detection may proceed by any known method, such as immunoblotting, Western analysis, gel-mobility shift assays, fluorescent in situ hybridization analysis (FISH), tracking of radioactive or bioluminescent markers, nuclear magnetic resonance, electron paramagnetic resonance, stopped-flow spectroscopy, column chromatography, capillary electrophoresis or other methods which track a molecule based upon an alteration in size and/or charge. The particular label or detectable group used in the assay is not a critical aspect of the invention. The detectable group can be any material having a detectable physical or chemical property, including magnetic beads, fluorescent dyes, radiolabels, enzymes and colorimetric labels or colored glass or plastic beads, as discussed for nucleic acid labels, supra. The label may be coupled directly or indirectly to the desired component of the assay according to methods well known in the art. As indicated above, a wide variety of labels may be used, with the choice of label depending on the sensitivity required, ease of conjugation of the compound, stability requirements, available instrumentation and disposal provisions. Means of detecting labels are well known to those of skill in the art.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound or a chemiluminescent compound. A number of ligands and anti-ligands can be used.

The molecules can also be conjugated directly to signal-generating compounds, e.g., by conjugation with an enzyme or fluorophore. Enzymes of interest as labels will primarily be hydrolases, particularly phosphatases, esterases and glycosidases or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal-producing systems which may be used, see, U.S. Pat. No. 4,391,904, which is incorporated herein by reference.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Assays for Compounds that Modulate Enzymatic Activity or Expression

A catalytically active polypeptide of the present invention may be contacted with a compound in order to determine whether said compound binds to and/or modulates the enzymatic activity of such polypeptide. The polypeptide employed will have at least 20%, 30%, 40%, 50%, 60%, 70% or 80% of the specific activity of the native, full-length enzyme of the present invention. Generally, the polypeptide will be present in a range sufficient to determine the effect of the compound, typically about 1 nM to 10 µM. Likewise, the compound being tested will be present in a concentration of from about 1 nM to 10 µM. Those of skill will understand that such factors as enzyme concentration, ligand concentrations (i.e., substrates, products, inhibitors, activators), pH, ionic strength and temperature will be controlled so as to obtain useful kinetic data and determine the presence or absence of a compound that binds or modulates polypeptide activity. Methods of measuring enzyme kinetics are well known in the art. See, e.g., Segel, (1976) Biochemical Calculations, $2^{nd}$ ed., John Wiley and Sons, New York.

The following examples are offered by way of illustration and not by way of limitation.

EXPERIMENTAL

Example 1

Cloning and Gene Characterization of GmIPT1 and GmIPT2

Below we describe the identification and characterization of two IPT polypeptides from soybean (*Glycine max*) designated GmIPT1 and GmIPT2.

Material and methods: Sequences putatively representing IPT genes in soybean were initially identified by an in silico search of soy EST databases using known *Arabidopsis* and maize IPT coding sequences. Two candidate ESTs, pk0031 and pk086, were selected based on protein-level homology to the reference sequences and consideration of the library from which the candidate sequence originated.

Based on the candidate EST sequences, primers 100066, 100067, 100068 and 100069 (SEQ ID NOs: 10-13, respectively) were created. Primer pairs 100066/100067 and 100068/100069 were used to screen a proprietary soybean BAC library. Super-pools identified were further screened with primer pair 100066/100067 and two BAC clones, C05 and 124, were selected.

In each case, touchdown PCR was performed (GeneAmp® PCR System 9700, Applied Biosystems), using the following cycling parameters: 94° C. for 3 min (one cycle), 94° C. for 1 min, 55° C. for 1 min and 72° C. for 1 min 30 s, (35 cycles), 72° C. for 7 min and termination at 4° C. *Pfu Ultra Hotstart*™ DNA polymerase (Stratagene) was used for its very low average error rate (less than 0.5% per 500-bp fragment amplified).

Soybean insert DNA was isolated from the BAC clones and digested with EcoRI or PstI for Southern blot confirmation using the pk0031 EST clone as a probe.

An EcoRI digestion of C05 was subcloned into pBluescript® (Stratagene Inc., La Jolla, Calif.). White colonies were grown in LB medium and transferred onto a membrane using a dot-blot procedure. After denaturation the membrane was probed with the pk0031 EST clone. Positive clones were identified and sequenced.

FIG. 1 provides an amino acid alignment of the ZmIPT2, GmIPT1, GmIPT2 and GmIPT3 cytokinin biosynthetic enzymes. Asterisks indicate amino acids conserved in many cytokinin biosynthetic enzymes. As shown in FIG. 1, the deduced protein sequence of the GmIPT genes contains the exact consensus sequence GxTxxGK[ST]xxxxx[VLI] xxxxxxx[VLI][VLI]xxDxxQx{57,60}[VLI][VLI]xGG[ST] (SEQ ID NO: 9) (where x denotes any amino acid residue, [ ] any one of the amino acids shown in [ ], and x{m,n} m to n amino acid residues in number) that was used by Takei, et al., (2001) *J. Biol. Chem.* 276:26405-26410 to isolate the *Arabidopsis* ipt genes.

GAP-derived percentage sequence identity and sequence similarity values for GmIPT 1, 2, and 3, relative to each other and to ZmIPT2 and *Arabidopsis* IPT1-9, are shown in FIG. 2. Identity to other plant IPT proteins was found to be no higher than 52%.

Example 2

Expression of GmIPT Genes

In order to study the level of expression of the GmIPT genes in various plant tissues, MPSS™ analysis (Solexa, Inc., Hayward, Calif.) was performed using 17-mer tags as shown in SEQ ID NOS: 14-16. In general, expression was found to be very low in most organs, but higher in reproductive tissues such as flowers (GmIPT1 and 2) and seed (GmIPT3). Tissue types, number of library hits and average ppm for each are presented in Table 1.

TABLE 1

| Gene | Tissue type | Average ppm | # of libraries |
|------|-------------|-------------|----------------|
| GmIPT1 | Flower | 32.1 | 1 |
| GmIPT1 | Leaf | 3.5 | 2 |
| GmIPT1 | Stem | 14.0 | 1 |
| GmIPT1 | Root | 8.0 | 1 |
| GmIPT2 | Flower | 68.5 | 6 |
| GmIPT2 | Leaf | 25.0 | 2 |
| GmIPT2 | Root | 15.5 | 2 |
| GmIPT2 | Seed | 13.2 | 5 |
| GmIPT3 | Leaf | 3.0 | 1 |
| GmIPT3 | Root | 5.5 | 4 |
| GmIPT3 | Seed | 13.3 | 12 |

Northern blots of GmIPT1 and GmIPT2 confirmed these findings. The expression pattern of GmIPT1 and GmIPT2 was further studied using Northern blot with RNA samples extracted from different soybean tissues (flowers, pods at different developmental stages, leaf, stem and root). GmIPT1 (AY550884) is expressed in stem and to a lesser extent in root, whereas GmIPT2 is highly expressed in roots and to a lesser extent in small pods and stem. During pod development, GmIPT2 was found to be expressed at higher levels in small pods and level of gene expression decreased as pod size and maturity increased. This suggests a more important role of GmIPT2 in early stages of pod development.

Northern analysis of GmIPT3 expression is planned.

DNA and RNA extraction: Genomic DNA was extracted from plant samples according to Dellaporta, et al., (1983) *Plant Mol Biol* 1:19-21 and stored at −20° C. Total RNA was prepared using a hot phenol extraction procedure according to Verwoerd, et al., (1989) *Nucleic Acid Res* 17:2362 and stored at −80° C. Samples were purified using *RNEASY Mini Protocol for RNA Cleanup* (QIAgen) and eluted in 50 µl DEPC water. Optical Density (DO) at 260 and 280 nm was used to assess the purity of RNA preps and measure RNA and DNA concentrations.

Southern blots Northern blots and hybridization: For Southern blots, digested genomic or BAC clones DNA were run on 0.8% agarose gel at 110V, stained after migration in a 1:10000 (v/v) ethidium bromide solution in TAE buffer, and transferred as indicated below. For Northern blots, ethidium bromide was added to denatured RNA samples and run at 80 V on 1.5% denaturing agarose gel (Brugiere, et al., (2003) *Plant Physiol.* 132:1228-1240). Blotting was performed using Turbo-blotter (Schleicher and Schuell) according to the manufacturer guidelines. After transfer, nylon membranes (Nytran plus, Schleicher and Schuell) were cross-linked with a Stratalinker (Stratagene) and baked at 80° C. for 30 min. Probes were labeled with [α-$^{32}$P]-dCTP using random priming (*Rediprime II RandomPrime Labelling System*, Amersham Biosciences) and purified with *Quick Spin Columns* (Roche). Hybridizations were carried out at 65° C. for 16 h using ExpressHyb hybridization solution (BD Biosciences) and membranes were washed under stringent conditions (0.1×SSC, 0.1% SDS) as previously described (Brugière, et al., (2003) *Plant Physiol.* 132:1228-1240). Relative transcript abundance was quantified using a phosphor imager (MD860, Molecular Dynamic) with imaging software (ImageQuant, Molecular Dynamics).

BAC subcloning: BAC clones were digested and subcloned in pBluescript SK+. This plasmid includes a multiple cloning site between the lacZ gene and its promoter. The lacZ gene is often used as a reporter gene because it encodes a β-galactosidase, which produces a dark blue precipitate on X-gal enzymatic hydrolysis. The bacteria containing a plasmid in which the BAC fragment is inserted in the multiple cloning site and therefore do not synthesize this enzyme will appear white. This allows the selection of colonies containing BAC subclones that can be further screened by PCR or Southern blot.

Example 4

Maintaining or Increasing Seed Set During Stress

Targeted overexpression of the IPT sequences of the invention to the developing female inflorescence of angiosperms, for example maize, soy, rice or wheat, will elevate cytokinin levels and allow developing seed to achieve their full genetic potential for size, minimize seed and/or pod abortion and buffer seed set during unfavorable environments. Abiotic stress that occurs during seed development in maize has been shown to cause reduction in cytokinin levels. Under stress conditions, it is likely that cytokinin biosynthesis activity is decreased and cytokinin degradation is increased (Brugière, et al., (2003) *Plant Physiol.* 132(3):1228-40). Consequently, in one non-limiting method, to maintain cytokinin levels in lag-phase seeds, IPT genes could be ligated to control elements that: 1) are stress insensitive; 2) direct expression of structural genes predominantly to the developing seeds and 3) preferentially drive expression of structural genes during the lag phase of seed development. Promoters which target expression to related maternal tissues at or around anthesis may also be employed. Alternatively, a constitutive promoter could be employed.

Example 5

Maize Transformation

For example, immature maize embryos from greenhouse donor plants are bombarded with a plasmid containing a sequence, for example GmIPt2, operably linked to the Zag2.1 promoter (Schmidt, et al., (1993) *Plant Cell* 5:729-737) and containing the selectable marker gene BAR (Wohlleben, et al., (1988) *Gene* 70:25-37), which confers resistance to the herbicide Bialaphos. Alternatively, the selectable marker gene is provided on a separate plasmid. Transformation is performed as follows. Media recipes follow below.

The ears are husked and surface-sterilized in 30% CLO-ROX bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5 cm target zone in preparation for bombardment.

A plasmid vector comprising the IPT sequence operably linked to a Zag2.1 promoter is made. This plasmid DNA plus plasmid DNA containing a BAR selectable marker is precipitated onto 1.1 μm (average diameter) tungsten pellets using a $CaCl_2$ precipitation procedure as follows: 100 μl prepared tungsten particles in water; 10 μl (1 μg) DNA in Tris EDTA buffer (1 μg total DNA); 100 μl 2.5 M $CaCl_2$; and, 10 μl 0.1 M spermidine.

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

The sample plates are bombarded at level #4 in particle gun #HE34-1 or #HE34-2. All samples receive a single shot at 650 PSI, with a total of ten aliquots taken from each tube of prepared particles/DNA.

Following bombardment, the embryos are kept on 560Y medium for 2 days, then transferred to 560R selection medium containing 3 mg/liter Bialaphos and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for the maintenance or increase of seed set during an abiotic stress episode. In addition, transformants under stress will be monitored for cytokinin levels (as described in Example 5c) and maintenance of kernel growth.

Bombardment medium (560Y) comprises 4.0 g/l N6 basal salts (SIGMA C-1416), 1.0 ml/l Eriksson's Vitamin Mix (1000×SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l GELRITE (added after bringing to volume with D-I $H_2O$) and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000×SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l GELRITE (added after bringing to volume with D-I $H_2O$) and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog, (1962) Physiol. Plant. 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l GELRITE (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6); and 6 g/l BACTO-agar (added after bringing to volume with polished D-I $H_2O$), sterilized and cooled to 60° C.

Example 6

Soybean Embryo Transformation

Soybean embryos are bombarded with a plasmid containing the IPT sequence operably linked to a ubiquitin promoter as follows. To induce somatic embryos, cotyledons, 3-5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can be maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein, et al., (1987) Nature (London) 327:70-73, U.S. Pat. No. 4,945,050). A Du Pont Biolistic PDS1000/HE instrument (helium retrofit) can be used for these transformations.

A selectable marker gene that can be used to facilitate soybean transformation is a transgene composed of the $^{35}S$ promoter from Cauliflower Mosaic Virus (Odell, et al., (1985) Nature 313:810-812), the hygromycin phosphotransferase gene from plasmid pJR225 (from E. coli; Gritz, et al., (1983) Gene 25:179-188) and the 3' region of the nopaline synthase gene from the T-DNA of the Ti plasmid of Agrobacterium tumefaciens. The expression cassette comprising the IPT sequence operably linked to the ubiquitin can be isolated as a restriction fragment. This fragment can then be inserted into a unique restriction site of the vector carrying the marker gene.

To 50 μl of a 60 mg/ml 1 μm gold particle suspension is added (in order): 5 μl DNA (1 μg/μl), 20 μl spermidine (0.1 M), and 50 μl $CaCl_2$ (2.5 M). The particle preparation is then agitated for three minutes, spun in a microfuge for 10 seconds and the supernatant removed. The DNA-coated particles are then washed once in 400 μl 70% ethanol and resuspended in 40 μl of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7

Sunflower Meristem Tissue Transformation

Sunflower meristem tissues are transformed with an expression cassette containing the IPT sequence operably linked to a ubiquitin promoter as follows (see also, EP Patent Number EP 0 486233, herein incorporated by reference, and Malone-Schoneberg, et al., (1994) *Plant Science* 103:199-207). Mature sunflower seed (*Helianthus annuus* L.) are dehulled using a single wheat-head thresher. Seeds are surface sterilized for 30 minutes in a 20% CLOROX bleach solution with the addition of two drops of TWEEN 20 per 50 ml of solution. The seeds are rinsed twice with sterile distilled water.

Split embryonic axis explants are prepared by a modification of procedures described by Schrammeijer, et al., (Schrammeijer, et al., (1990) *Plant Cell Rep.* 9:55-60). Seeds are imbibed in distilled water for 60 minutes following the surface sterilization procedure. The cotyledons of each seed are then broken off, producing a clean fracture at the plane of the embryonic axis. Following excision of the root tip, the explants are bisected longitudinally between the primordial leaves. The two halves are placed, cut surface up, on GBA medium consisting of Murashige and Skoog mineral elements (Murashige, et al., (1962) *Physiol. Plant.* 15:473-497), Shepard's vitamin additions (Shepard, (1980) in *Emergent Techniques for the Genetic Improvement of Crops* (University of Minnesota Press, St. Paul, Minn.), 40 mg/l adenine sulfate, 30 g/l sucrose, 0.5 mg/l 6-benzyl-aminopurine (BAP), 0.25 mg/l indole-3-acetic acid (IAA), 0.1 mg/l gibberellic acid ($GA_3$), pH 5.6, and 8 g/l Phytagar.

The explants are subjected to microprojectile bombardment prior to *Agrobacterium* treatment (Bidney, et al., (1992) *Plant Mol. Biol.* 18:301-313). Thirty to forty explants are placed in a circle at the center of a 60×20 mm plate for this treatment. Approximately 4.7 mg of 1.8 mm tungsten microprojectiles are resuspended in 25 ml of sterile TE buffer (10 mM Tris HCl, 1 mM EDTA, pH 8.0) and 1.5 ml aliquots are used per bombardment. Each plate is bombarded twice through a 150 mm nytex screen placed 2 cm above the samples in a PDS1000® particle acceleration device.

Disarmed *Agrobacterium tumefaciens* strain EHA105 is used in all transformation experiments. A binary plasmid vector comprising the expression cassette that contains the IPT gene operably linked to the ubiquitin promoter is introduced into *Agrobacterium* strain EHA105 via freeze-thawing as described by Holsters, et al., (1978) *Mol. Gen. Genet.* 163:181-187. This plasmid further comprises a kanamycin selectable marker gene (i.e., nptII). Bacteria for plant transformation experiments are grown overnight (28° C. and 100 RPM continuous agitation) in liquid YEP medium (10 gm/l yeast extract, 10 gm/l Bactopeptone, and 5 gm/l NaCl, pH 7.0) with the appropriate antibiotics required for bacterial strain and binary plasmid maintenance. The suspension is used when it reaches an $OD_{600}$ of about 0.4 to 0.8. The *Agrobacterium* cells are pelleted and resuspended at a final $OD_{600}$ of 0.5 in an inoculation medium comprised of 12.5 mM MES pH 5.7, 1 gm/l $NH_4Cl$, and 0.3 gm/l $MgSO_4$.

Freshly bombarded explants are placed in an *Agrobacterium* suspension, mixed and left undisturbed for 30 minutes. The explants are then transferred to GBA medium and co-cultivated, cut surface down, at 26° C. and 18-hour days. After three days of co-cultivation, the explants are transferred to 374B (GBA medium lacking growth regulators and a reduced sucrose level of 1%) supplemented with 250 mg/l cefotaxime and 50 mg/l kanamycin sulfate. The explants are cultured for two to five weeks on selection and then transferred to fresh 374B medium lacking kanamycin for one to two weeks of continued development. Explants with differentiating, antibiotic-resistant areas of growth that have not produced shoots suitable for excision are transferred to GBA medium containing 250 mg/l cefotaxime for a second 3-day phytohormone treatment. Leaf samples from green, kanamycin-resistant shoots are assayed for the presence of NPTII by ELISA and for the presence of transgene expression by assaying for cytokinin synthesis activity. Such assays are described elsewhere herein.

NPTII-positive shoots are grafted to Pioneer® hybrid 6440 in vitro-grown sunflower seedling rootstock. Surface sterilized seeds are germinated in 48-0 medium (half-strength Murashige and Skoog salts, 0.5% sucrose, 0.3% GELRITE, pH 5.6) and grown under conditions described for explant culture. The upper portion of the seedling is removed, a 1 cm vertical slice is made in the hypocotyl, and the transformed shoot inserted into the cut. The entire area is wrapped with parafilm to secure the shoot. Grafted plants can be transferred to soil following one week of in vitro culture. Grafts in soil are maintained under high humidity conditions followed by a slow acclimatization to the greenhouse environment. Transformed sectors of $T_0$ plants (parental generation) maturing in the greenhouse are identified by NPTII ELISA and/or by cytokinin synthesis activity analysis of leaf extracts while transgenic seeds harvested from NPTII-positive $T_0$ plants are identified by cytokinin synthesis activity analysis of small portions of dry seed cotyledon.

Example 8

Rice Transformation

One method for transforming DNA into cells of higher plants that is available to those skilled in the art is high-velocity ballistic bombardment using metal particles coated with the nucleic acid constructs of interest (see, Klein, et al., (1987) *Nature* (London) 327:70-73 and see, U.S. Pat. No. 4,945,050). A Biolistic PDS-1000/He (BioRAD Laboratories, Hercules, Calif.) is used for these complementation experiments.

The bacterial hygromycin B phosphotransferase (Hpt II) gene from *Streptomyces hygroscopicus* that confers resistance to the antibiotic may be used as the selectable marker for rice transformation. In the vector, the Hpt II gene may be engineered with the 35S promoter from Cauliflower Mosaic Virus and the termination and polyadenylation signals from the octopine synthase gene of *Agrobacterium tumefaciens*.

For example, see the description of vector pML18 in WO 97/47731, published on Dec. 18, 1997, the disclosure of which is hereby incorporated by reference.

Embryogenic callus cultures derived from the scutellum of germinating rice seeds serve as source material for transformation experiments. This material is generated by germinating sterile rice seeds on a callus initiation media (MS salts, Nitsch and Nitsch vitamins, 1.0 mg/l 2,4-D and 10 µM AgNO$_3$) in the dark at 27-28° C. Embryogenic callus proliferating from the scutellum of the embryos is transferred to CM media (N6 salts, Nitsch and Nitsch vitamins, 1 mg/l 2,4-D, Chu, et al., (1985) *Sci. Sinica* 18:659-668). Callus cultures are maintained on CM by routine sub-culture at two-week intervals and used for transformation within 10 weeks of initiation.

Callus is prepared for transformation by subculturing 0.5-1.0 mm pieces approximately 1 mm apart, arranged in a circular area of about 4 cm in diameter, in the center of a circle of Whatman #541 paper placed on CM media. The plates with callus are incubated in the dark at 27-28° C. for 3-5 days. Prior to bombardment, the filters with callus are transferred to CM supplemented with 0.25 M mannitol and 0.25 M sorbitol for 3 hr in the dark. The petri dish lids are then left ajar for 20-45 minutes in a sterile hood to allow moisture on tissue to dissipate.

Each genomic DNA fragment is co-precipitated with pML18 (containing the selectable marker for rice transformation) onto the surface of gold particles. To accomplish this, a total of 10 µg of DNA at a 2:1 ratio of trait:selectable marker DNAs are added to 50 µl aliquot of gold particles that have been resuspended at a concentration of 60 mg ml-1. Calcium chloride (50 µl of a 2.5 M solution) and spermidine (20 µl of a 0.1 M solution) are then added to the gold-DNA suspension as the tube is vortexing for 3 min. The gold particles are centrifuged in a microfuge for 1 sec and the supernatant removed. The gold particles are washed twice with 1 ml of absolute ethanol and then resuspended in 50 µl of absolute ethanol and sonicated (bath sonicator) for one second to disperse the gold particles. The gold suspension is incubated at −70° C. for five minutes and sonicated (bath sonicator) if needed to disperse the particles. Six µl of the DNA-coated gold particles are then loaded onto mylar macrocarrier disks and the ethanol is allowed to evaporate.

At the end of the drying period, a petri dish containing the tissue is placed in the chamber of the PDS-1000/He. The air in the chamber is then evacuated to a vacuum of 28-29 inches Hg. The macrocarrier is accelerated with a helium shock wave using a rupture membrane that bursts when the He pressure in the shock tube reaches 1080-1100 psi. The tissue is placed approximately 8 cm from the stopping screen and the callus is bombarded two times. Two to four plates of tissue are bombarded in this way with the DNA-coated gold particles. Following bombardment, the callus tissue is transferred to CM media without supplemental sorbitol or mannitol.

Within 3-5 days after bombardment the callus tissue is transferred to SM media (CM medium containing 50 mg/l hygromycin). To accomplish this, callus tissue is transferred from plates to sterile 50 ml conical tubes and weighed. Molten top-agar at 40° C. is added using 2.5 ml of top agar/100 mg of callus. Callus clumps are broken into fragments of less than 2 mm diameter by repeated dispensing through a 10 ml pipet. Three ml aliquots of the callus suspension are plated onto fresh SM media and the plates are incubated in the dark for 4 weeks at 27-28° C. After 4 weeks, transgenic callus events are identified, transferred to fresh SM plates and grown for an additional 2 weeks in the dark at 27-28° C.

Growing callus is transferred to RM1 media (MS salts, Nitsch and Nitsch vitamins, 2% sucrose, 3% sorbitol, 0.4% GELRITE+50 ppm hyg B) for 2 weeks in the dark at 25° C. After 2 weeks the callus is transferred to RM2 media (MS salts, Nitsch and Nitsch vitamins, 3% sucrose, 0.4% GELRITE+50 ppm hyg B) and placed under cool white light (~40 µm-2s$^{-1}$) with a 12 hr photoperiod at 25° C. and 30-40% humidity. After 2-4 weeks in the light, callus begin to organize, and form shoots. Shoots are removed from surrounding callus/media and gently transferred to RM3 media (½×MS salts, Nitsch and Nitsch vitamins, 1% sucrose+50 ppm hygromycin B) in phytatrays (Sigma Chemical Co., St. Louis, Mo.) and incubation is continued using the same conditions as described in the previous step.

Plants are transferred from RM3 to 4" pots containing Metro mix 350 after 2-3 weeks, when sufficient root and shoot growth have occurred.

Example 9

Modulating Root Development

For *Agrobacterium*-mediated transformation of soybean with a plasmid designed to achieve post-transcriptional gene silencing (PTGS) with an appropriate promoter, the method of Zhao may be employed (U.S. Pat. No. 5,981,840, and PCT Patent Publication Number WO98/32326, the contents of which are hereby incorporated by reference). Briefly, immature embryos are isolated and contacted with a suspension of *Agrobacterium* capable of transferring a DNA construct. Said construct may comprise the CRWAQ81 root-preferred promoter::ADH intron promoter operably linked to a hairpin structure made from the coding sequence of any one of the GmIPT polynucleotides of the invention. Other useful constructs may comprise a hairpin construct targeting the promoter of any one of the GmIPT polynucleotides of the invention. (Aufsatz, et al., (2002) *PNAS* 99(4):16499-16506; Mette, et al., (2000) *EMBO J.* 19(19):5194-5201) The construct is transferred to at least one cell of at least one of the immature embryos (step 1: the infection step). In this step the immature embryos are immersed in an *Agrobacterium* suspension for the initiation of inoculation. The embryos are co-cultured for a time with the *Agrobacterium* (step 2: the co-cultivation step); this may take place on solid medium. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). Next, inoculated embryos are cultured on medium containing a selective agent; growing, transformed callus is recovered (step 4: the selection step). The callus is then regenerated into plants (step 5: the regeneration step).

Plants are monitored and scored for a modulation in root development. The modulation in root development includes monitoring for enhanced root growth of one or more root parts including the primary root, lateral roots, adventitious roots, etc. Methods of measuring such developmental alterations in the root system are known in the art. See, for example, US Patent Application Publication Number 2003/0074698 and Werner, et al., (2001) PNAS18:10487-10492, both of which are herein incorporated by reference.

Example 10

Modulating Senescence of a Plant

A DNA construct comprising the GmIPT1 or GmIPT2 polynucleotide operably linked to a constitutive promoter, a root-preferred promoter, or a senescence-activated promoter, such as SAG12 (Gan, et al., (1995) *Science* 270:5244, Genbank Accession Number U37336) is introduced into maize plants as outlined in Zhao, et al., (1998) *Maize Genetics Corporation Newsletter* 72:34-37, herein incorporated by reference.

For example, maize plants comprising an IPT sequence operably linked to the SAG12 promoter are obtained. As a control, a non-cytokinin-related construct is also introduced into maize plants using the transformation method outlined above. The phenotypes of transgenic maize plants having an elevated level of the IPT polypeptide are studied. For example, plants can be monitored for an improved vitality, shelf and vase life, and improved tolerance against infection. Plants could also be monitored for delayed senescence under various environmental stresses including, for example, flooding which normally results in leaf chlorosis, necrosis, defoliation, cessation of growth and reduction in yield.

Example 11

Variants of IPT

A. Variant Nucleotide Sequences of GmIPT1, GmIPT2, or GmIPT3 That Do Not
Alter the Encoded Amino Acid Sequence The GmIPT nucleotide sequences set forth in SEQ ID NO: 1, 3 and 6 are used to generate variant nucleotide sequences having the nucleotide sequence of the open reading frame with about 70%, 75%, 80%, 85%, 90% or 95% nucleotide sequence identity when compared to the corresponding starting unaltered ORF nucleotide sequence. These functional variants are generated using a standard codon table. While the nucleotide sequence of the variant is altered, the amino acid sequence encoded by the open reading frame does not change.

B. Variant Amino Acid Sequences of GmIPT1, GmIPT2, and GmIPT3

Variant amino acid sequences of GmIPT1, GmIPT2 and GmIPT3 are generated. In this example, one or more amino acids are altered. Specifically, the open reading frame set forth in SEQ ID NO: 2, 4 or 7 is reviewed to determine the appropriate amino acid alteration. The selection of an amino acid to change is made by consulting a protein alignment with orthologs and other gene family members from various species. See, FIG. 1 and/or FIG. 4. An amino acid is selected that is deemed not to be under high selection pressure (not highly conserved) and which is rather easily substituted by an amino acid with similar chemical characteristics (i.e., similar functional side-chain). Assays as outlined elsewhere herein may be followed to confirm functionality. Variants having about 70%, 75%, 80%, 85%, 90% or 95% nucleic acid sequence identity to each of SEQ ID NO: 2, 4 and 7 are generated using this method.

C. Additional Variant Amino Acid Sequences of GmIPT1 and GmIPT2

In this example, artificial protein sequences are created having 80%, 85%, 90% and 95% identity relative to the reference protein sequence. This latter effort requires identifying conserved and variable regions from the alignment set forth in FIG. 1 and then the judicious application of an amino acid substitutions table. These parts will be discussed in more detail below.

Largely, the determination of which amino acid sequences are altered is made based on the conserved regions among the IPT proteins or among the other IPT polypeptides. See, FIG. 1. Based on the sequence alignment, the various regions of the IPT polypeptides that can likely be altered can be determined. It is recognized that conservative substitutions can be made in the conserved regions without altering function. In addition, one of skill will understand that functional variants of the IPT sequence of the invention can have minor non-conserved amino acid alterations in the conserved domain.

Artificial protein sequences are then created that are different from the original in the intervals of 80-85%, 85-90%, 90-95% and 95-100% identity. Midpoints of these intervals are targeted, with liberal latitude of plus or minus 1%, for example. The amino acids substitutions will be effected by a custom Perl script. The substitution table is provided below in Table 2.

First, any conserved amino acids in the protein that should not be changed are identified and "marked off" for insulation from the substitution. The start methionine will of course be added to this list automatically. Next, the changes are made.

H, C and P are not changed. The changes will occur with isoleucine first, sweeping N-terminal to C-terminal. Then leucine, and so on down the list until the desired target is reached. Interim number substitutions can be made so as not to cause reversal of changes. The list is ordered 1-17, so start with as many isoleucine changes as needed before leucine, and so on down to methionine. Clearly many amino acids will in this manner not need to be changed. L, I and V will involve a 50:50 substitution of the two alternate optimal substitutions.

The variant amino acid sequences are written as output. Perl script is used to calculate the percent identities. Using this procedure, variants of GmIPT1 and GmIPT2 are generated having about 82%, 87%, 92%, and 97% amino acid identity to the starting unaltered ORF nucleotide sequence of SEQ ID NO: 2 or 4.

TABLE 2

Substitution Table

| Amino Acid | Strongly Similar and Optimal Substitution | Rank of Order to Change | Comment |
|---|---|---|---|
| I | L, V | 1 | 50:50 substitution |
| L | I, V | 2 | 50:50 substitution |
| V | I, L | 3 | 50:50 substitution |
| A | G | 4 | |
| G | A | 5 | |
| D | E | 6 | |
| E | D | 7 | |
| W | Y | 8 | |
| Y | W | 9 | |
| S | T | 10 | |
| T | S | 11 | |
| K | R | 12 | |
| R | K | 13 | |
| N | Q | 14 | |
| Q | N | 15 | |
| F | Y | 16 | |
| M | L | 17 | First methionine cannot change |
| H | | Na | No good substitutes |
| C | | Na | No good substitutes |
| P | | Na | No good substitutes |

Example 12

Amplification of Additional Isopentenyl Transferase (IPT) Genes from Soybean or other Plant Species Additional IPT genes from plant species could be identified by PCR or RT-PCR methods using degenerate primers such as the ones described below. Degenerate primers can be designed against conserved amino acid motifs found in available IPT proteins from soybean, maize, rice or *Arabidopsis*. Such motifs can be identified from an alignment of the protein sequences. Examples of sequences of such motifs and corresponding degenerate nucleotide primers are listed below:

| Amino acid motif | Sense degenerate primer | Antisense degenerate primer |
|---|---|---|
| EIINSDK(I/M)Q SEQ ID NO: 17 | GAR ATH ATH AAY WSI GAY AAR ATI CA SEQ ID NO: 18 | TG IAT YTT RTC ISW RTT DAT DAT YTC SEQ ID NO: 19 |
| GVPHHLLG SEQ ID NO: 20 | GGI GTI CCI CAY CAY YTI YTI GG SEQ ID NO: 21 | CC IAR IAR RTG RTG IGG IAC ICC SEQ ID NO: 22 |
| GVPHHLL SEQ ID NO: 23 | GGI GTI CCI CAY CAY YTI YT SEQ ID NO: 24 | IAR IAR RTG RTG IGG IAC ICC SEQ ID NO: 25 |
| AGGSN SEQ ID NO: 26 | GCI GGI GGI WSI AAY SEQ ID NO: 27 | RTT ISW ICC ICC IGC SEQ ID NO: 28 |
| (A/V)GGSNS(Y/F) SEQ ID NO: 29 | GYI GGI GGI WSI AAY WSI TWY SEQ ID NO: 30 | RWA ISW RTT ISW ICC ICC IRC SEQ ID NO: 31 |
| CCF[I/L]WVDV SEQ ID NO: 32 | TGY TGY TTY HTI TGG GTI GAY GT SEQ ID NO: 33 | AC RTC IAC CCA IAD RAA RCA RCA SEQ ID NO: 34 |

Sense/antisense primers could be used in different combinations. Similarly, several rounds of PCR could be used. The product of amplification of one pair of sense/antisense primers could be used as template for PCR with another set of internal (nested) degenerate primers therefore maximizing the chances for amplification of an appropriate sequence, i.e., containing a sequence corresponding to the corresponding amino acid motif.

| Nucleotide Symbols | | |
|---|---|---|
| A | A | Adenine |
| C | C | Cytosine |
| G | G | Guanine |
| T | T | Thymine |
| U | U | Uracil |
| I | I | Inosine |
| R | A or G | puRine |
| Y | C or T (U) | pYrimidine |
| M | A or C | aMino |
| K | G or T (U) | Keto |
| S | C or G | Strong (triple '3 H' bonds) |
| W | A or T (U) | Weak (double '2 H' bonds) |

-continued

| Nucleotide Symbols | | |
|---|---|---|
| B | C or G or T (U) | not A |
| D | A or G or T (U) | not C |
| H | A or C or T (U) | not G |
| V | A or C or G | not T (U) |
| N | A or C or G or T (U) | aNy nucleotide |

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated or recombinant polynucleotide which encodes a polypeptide which is 95% identical to the full length of SEQ ID NO: 7 and which comprises the consensus sequence of SEQ ID NO: 9.

2. An isolated or recombinant polynucleotide comprising the complete nucleotide sequence of SEQ ID NO: 6.

3. A transgenic plant or plant part comprising an isolated or recombinant polynucleotide operably linked to a promoter that drives expression in the plant or plant part, wherein said polynucleotide is the polynucleotide of claim 1.

4. The plant of claim 3, wherein said polynucleotide is operably linked to a tissue-preferred promoter, a constitutive promoter, or an inducible promoter.

5. The plant of claim 4, wherein said tissue-preferred promoter is a root-preferred promoter, a leaf-preferred promoter, a shoot-preferred promoter, or an inflorescence-preferred promoter.

6. The plant of claim 3, wherein said promoter is stress-insensitive and is expressed in a tissue of the developing seed or related maternal tissue at or about the time of anthesis.

7. The plant part of claim 3, wherein said part is a seed.

* * * * *